(12) United States Patent
Zhan

(10) Patent No.: US 8,653,025 B2
(45) Date of Patent: Feb. 18, 2014

(54) POLYHETEROCYCLIC COMPOUNDS HIGHLY POTENT AS HCV INHIBITORS

(75) Inventor: Zheng-Yun James Zhan, Shanghai (CN)

(73) Assignee: AB Pharma Ltd., Shanghai (CN)

( * ) Notice: Subject to any disclaimer, the term of this patent is extended or adjusted under 35 U.S.C. 154(b) by 255 days.

(21) Appl. No.: 13/014,993

(22) Filed: Jan. 27, 2011

(65) Prior Publication Data

US 2011/0183895 A1    Jul. 28, 2011

(30) Foreign Application Priority Data

Jan. 27, 2010   (CN) .......................... 2010 1 0101403

(51) Int. Cl.
*A61K 38/00* (2006.01)
*A01N 37/18* (2006.01)
*A61P 31/12* (2006.01)

(52) U.S. Cl.
USPC ........................................................ 514/3.7

(58) Field of Classification Search
None
See application file for complete search history.

(56) References Cited

PUBLICATIONS

Ettmayer P. et al. J. Med. Chem. (2004) 47(10), pp. 2393-2404.*

(Continued)

*Primary Examiner* — Thomas Heard
(74) *Attorney, Agent, or Firm* — Oblon, Spivak, McClelland, Maier & Neustadt, L.L.P.

(57) ABSTRACT

The present invention discloses the structure, preparation methods and uses of a series of novel polyheterocyclic based compounds (Ia-Ib and IIa-IIb) that are highly effective for inhibiting hepatitis C virus (HCV):

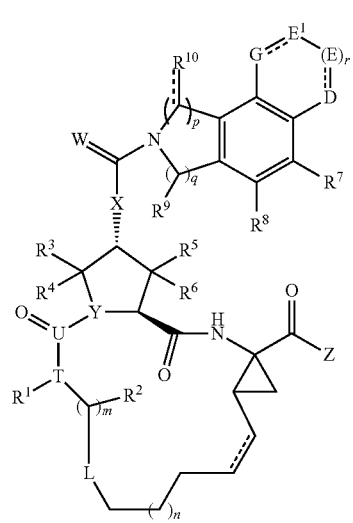

Ia

-continued

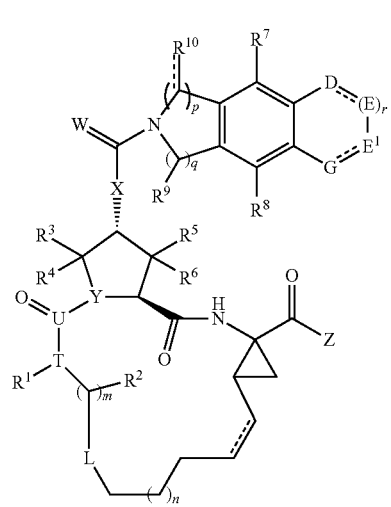

Ib

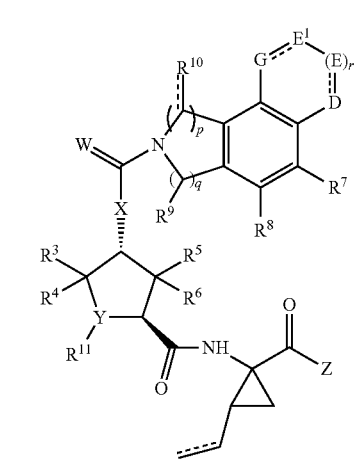

IIa

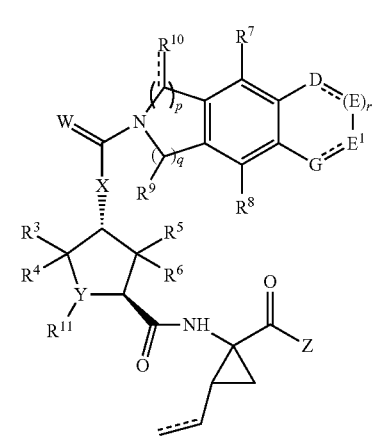

IIb where the structural variables are defined herein. The present invention is also provides a method of treating HCV infection by the polyheterocyclic based HCV inhibitory compounds, compositions and therapeutic methods.

33 Claims, No Drawings

(56) References Cited

PUBLICATIONS

Singh, Yashveer et al, "Recent Trends in Targeted Anticancer Prodrug and Conjugate," DesignCurr Med Chem. 2008; 15(18): 1802-1826.*

Muller, Christa E. "Prodrug Approaches for Enhancing the Bioavailability of Drugs with Low Solubility," Chemistry & Biodiversity, vol. 6 (2009), pp. 2071-2083.*

Beaumont, et, al "Design of Ester Prodrugs to Enhance Oral Absorption of Poorly Permeable Compounds: Challenges to the Discovery Scientist," Current Drug Metabolism, 2003, 4, 461-485.*

Han, H.-K.. AAPS Pharmsci. (2000) 2(1), Article 6, pp. 1-11.*

Testa Prodrug research: futile or fertile? Biochemical Pharmacology (2004) 2097-2106.*

* cited by examiner

POLYHETEROCYCLIC COMPOUNDS HIGHLY POTENT AS HCV INHIBITORS

FIELD OF THE INVENTION

The present invention relates to novel polyheterocyclic based compounds with both linear and macrocyclic structure, especially with tri-heterocyclic functional groups, which are highly potent and effective to inhibit the NS3 protease replication of hepatitis C virus (HCV). The invention also relates to preparation and the uses thereof as HCV inhibitors.

BACKGROUND OF THE INVENTION

Hepatitis C virus (HCV) is the major causative agent for most cases of non-A, non-B hepatitis. The virus is a single-stranded positive RNA virus in the Flaviviridae family. It includes a nucleocapsid protein (C), envelope proteins (E1 and E2), and several non-structural proteins (NS1, NS2, NS3, NS4a, NS5a, and NS5b). The NS3 protein possesses serine protease activity and is considered essential for viral replication and infectivity, and the essentiality of the NS3 protease was inferred from the fact that mutations in the yellow fever virus NS3 protease decreased viral infectivity [reference: Chamber et al, *Proc. Natl. Acad. Sci. USA* 87, 8898-8902 (1990).

So far, HCV infection is one of major human health problems since HCV infection leads to chronic liver disease such as cirrhosis and hepatocellular carcinoma. Due to the fact that the number of HCV infected individuals is estimated 2-15% of the world's population while no any effective vaccines or therapeutic agents are available to control or cure HCV [reference: WO 89/04669; Lavanchy, *J. Viral Hepatitis*, 6, 35-47 (1999); Alter, *J. Hepatology*, 31 (Suppl. 1), 88-91 (1999); and Alberti et al, *J. Hepatology*, 31 (Suppl. 1), 17-24 (1999)].

It has been demonstrated that mutations at the active site of the HCV NS3 protease completely inhibited the HCV infection in chimpanzee model [reference: Rice et al, *J. Virol.* 74 (4) 2046-51 (2000)]. Furthermore, the HCV NS3 serine protease has been found to facilitate proteolysis at the NS3/NS4a, NS4a/NS4b, NS4b/NS5a, NS5a/NS5b junctions and is thus responsible for generating four viral proteins during viral replication [reference: US 2003/0207861]. Consequently, the HCV NS3 serine protease enzyme is an attractive and effective target to develop new inhibitors for HCV infection. So far, there are different kinds of potential NS3 HCV protease inhibitors reported by global research institutes and pharmaceuticals, such as WO2010033466, WO2010075127, US20100003214, US20100022578, US20100029715, US20100041889, WO2009134624, WO2009010804, US20090269305, WO2008057209, WO2008057208, WO2007015787, WO2005037214, WO200218369, WO200009558, WO200009543, WO199964442, WO199907733, WO199907734, WO199950230, WO199846630, WO199817679, U.S. Pat. No. 5,990,276, Dunsdon et al, *Biorg. Med. Chem. Lett.* 10, 1571-1579 (2000); Llinas-Brunet et al, *Biorg. Chem. Lett.* 10, 2267-2270 (2000); and S. LaPlante et al., Biorg. Med. Chem. Lett. 10, 2271-2274 (2000).

Currently, due to lack of immunity or remission associated with HCV infection, hepatitis caused by HCV infection is more difficult to treat comparing to other forms of hepatitis. Now, the only available anti-HCV therapies are interferon-a, interferon-a/ribavirin combination, and pegylated interferon-a. However, sustained response rates for interferon-a or interferon-a/ribavirin combination were found to be <50% and patients suffer greatly from side effects of these therapeutic agents [reference: Walker, *DDT*, 4, 518-529 (1999); Weiland, *FEMS Microbial. Rev.*, 14, 279-288 (1994); and WO 02/18369]. Based on the significant importance for controlling HCV infection, the aim of the present invention is to develop more effective and better-tolerated therapeutic drugs for inhibiting HCV NS3 protease replication.

SUMMARY OF THE INVENTION

The present invention relates to two classes of novel polyheterocyclic based compounds of the following formulas Ia-Ib with macrocyclic structure and IIa-IIb with linear structure, especially with tri-heterocyclic functional groups, which has been evaluated to be highly potent and effective for inhibiting the NS3 protease replication of hepatitis C virus (HCV). This invention further relates to pharmaceutical compositions comprising one or more of new developed compounds (in a pure form or mixture of stereoisomers, solvates, hydrates, tautomers, prodrugs, or pharmaceutically acceptable salts thereof) and another agent(s) developed as therapeutic drugs for HCV treatment.

In the first aspect, the present invention provides polyheterocyclic based compounds having the following macrocyclic structure Ia and Ib:

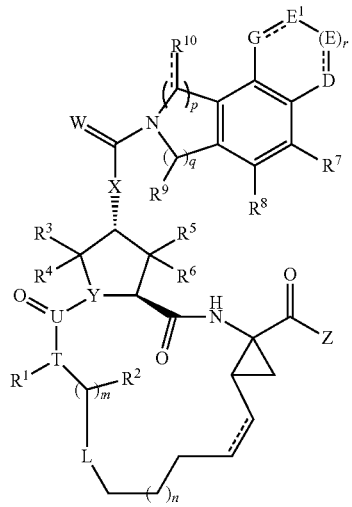

Ia

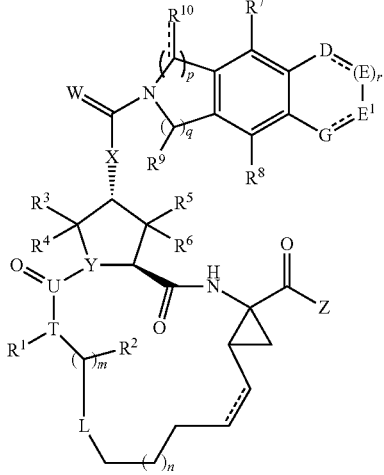

Ib and/or stereoisomers, solvates, hydrates, tautomers, esterification or amidation prodrugs, pharmaceutically acceptable salt, or mixtures thereof, wherein:

m=0, 1 or 2;
n=0, 1 or 2;
p=0, 1 or 2;
q=0, 1 or 2;
r=0, 1, 2 or 3;
each dashed line "====" is, independently, a single bond or double bond;
wherein when D and E are connected by a single bond, D and E are each, independently, selected from the group consisting of O, S, amino, and —C(Ra)(Rb)—; and $R^{10}$ is hydrogen, oxygen, halogen atom, cyano, trifluoromethyl, $C_1$-$C_{20}$ alkyl, $C_1$-$C_{20}$ alkoxy, alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;
wherein when D and E are connected by a double bond, D and E each, independently, selected from the group consisting of N or —C(Rc)-;
wherein when $E^1$ and G are connected by a single bond, $E^1$ and G are each, independently, selected from the group consisting of O, S, amino, and —C(Ra)(Rb)—; and $R^{10}$ is hydrogen, oxygen, halogen atom, cyano, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;
wherein when $E^1$ and G are connected by a double bond, $E^1$ and G are each, independently, selected from the group consisting of N or —C(Rc)-;
wherein when the dashed line connecting $R^{10}$ to the macrocycle is a double bond, $R^{10}$ is O or S;
wherein when the dashed line connecting $R^{10}$ to the macrocycle is a single bond, $R^{10}$ is hydrogen, halogen atom, cyano, trifluoromethyl, $C_1$-$C_{20}$ alkyl, $C_1$-$C_{20}$ alkoxy, alkylthio, $C_1$-$C_{20}$ alkoxycarbonyl, aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;
Ra, Rb and Rc are each, independently, selected from the group consisting of hydrogen, halogen atom, cyano, nitro, $C_1$-$C_{20}$ alkyl, $C_3$-$C_{20}$ cycloalkyl, $C_6$-$C_{20}$ aryl, $C_1$-$C_{20}$ alkoxy, $C_1$-$C_{20}$ alkylthio, alkoxycarbonyl, $C_6$-$C_{20}$ aryloxy, $C_6$-$C_{20}$ aryloxycarbonyl, $C_2$-$C_{20}$ heterocyclic alkoxycarbonyl, $C_2$-$C_{20}$ heterocyclic aryl, $C_1$-$C_{20}$ alkylamino, $C_2$-$C_{20}$ heterocyclic amino, $C_6$-$C_{20}$ aryl amino, $C_1$-$C_{20}$ aminocarbonyl, $C_1$-$C_{20}$ amido, $C_1$-$C_{20}$ amidocarbonyl, $C_1$-$C_{20}$ carbonylamino, $C_1$-$C_{20}$ alkylsulfonamido, $C_2$-$C_{20}$ heterocyclic sulfonamido, $C_6$-$C_{20}$ arylsulfonamido, and $C_1$-$C_{20}$ aminosulfonamido group;
wherein when r=0, E is nothing, and the D group is directly linked to the $E^1$ group;
L is oxygen, sulfur, —S(O)—, —S(O)$_2$—, carbonyl, —C(Rb)(Rc)-, —C(Rb)=C(Rc)-, $C_1$-$C_{20}$ alkoxy, $C_2$-$C_{20}$ heterocyclyl, $C_2$-$C_{20}$ heterocyclic alkoxy, —N(Ra)—, $C_1$-$C_{20}$ aminocarbonyl, $C_1$-$C_{20}$ alkoxycarbonyl, $C_6$-$C_{20}$ aryl, $C_6$-$C_{20}$ aryloxy, or $C_6$-$C_{20}$ aryloxycarbonyl group, wherein Ra, Rb and Rc are as defined above;
T is N, O or CH, wherein when T is O, $R^1$ is not present;
U is C, S, —S(O)—, P or phosphate;
W is O or S;
X is O, S or —NRa—, wherein Ra is defined above;
Y is N or CH;
Z is hydroxyl, $C_1$-$C_{20}$ alkyl, $C_3$-$C_{20}$ cycloalkyl, $C_1$-$C_{20}$ alkoxy, $C_3$-$C_{20}$ cycloalkoxy, $C_1$-$C_{20}$ alkylamino, $C_3$-$C_{20}$ cycloalkylamino, $C_2$-$C_{20}$ heterocyclic amino, $C_6$-$C_{20}$ aryl, $C_6$-$C_{20}$ arylamino, $C_4$-$C_{20}$ heteroarylamino, $C_1$-$C_{20}$ alkyl sulfonamido, $C_3$-$C_{20}$ cycloalkylsulfonamido, $C_6$-$C_{20}$ arylsulfonamido, $C_1$-$C_{20}$ alkoxy sulfonamido, $C_3$-$C_{20}$ cycloalkoxy sulfonamido, $C_1$-$C_{20}$ alkylamino sulfonamido, $C_3$-$C_{20}$ cycloalkylamino sulfonamido, $C_6$-$C_{20}$ arylamino sulfonamido, $C_1$-$C_{20}$ uramido, $C_1$-$C_{20}$ thioureido, $C_1$-$C_{20}$ phosphate, or $C_1$-$C_{20}$ borate;
$R^1$ and $R^2$ are each, independently, selected from the group consisting of hydrogen, hydroxyl, amino, $C_1$-$C_2$ alkyl, $C_3$-$C_{20}$ cycloalkyl, $C_1$-$C_{20}$ alkoxy, $C_3$-$C_{20}$ cycloalkoxy, $C_1$-$C_{20}$ alkoxycarbonyl, $C_1$-$C_{20}$ alkylamino, $C_3$-$C_{20}$ cycloalkylamino, $C_2$-$C_{20}$ heterocyclic amino, $C_6$-$C_{20}$ arylamino, $C_1$-$C_{20}$ alkoxycarbonylamino, $C_6$-$C_{20}$ aryloxycarbonylamino, $C_1$-$C_{20}$ alkylsulfonamido, $C_3$-$C_{20}$ cycloalkylsulfonamido, $C_2$-$C_{20}$ heterocyclic sulfonamido, $C_6$-$C_{20}$ arylsulfonamido, and $C_1$-$C_{20}$ aminosulfonamido group;
$R^3$, $R^4$, $R^5$ and $R^6$ are each, independently, selected from the group consisting of hydrogen, halogen, hydroxyl, cyano, nitro, $C_1$-$C_{20}$ alkyl, $C_3$-$C_{20}$ cycloalkyl, $C_1$-$C_{20}$ alkoxy, $C_1$-$C_{20}$ alkylamino, $C_2$-$C_{20}$ heterocyclicamino, $C_6$-$C_{20}$ aryl, $C_6$-$C_{20}$ arylamino, $C_1$-$C_{20}$ alkylsulfonamido, $C_2$-$C_{20}$ heterocyclic sulfonamido, and $C_6$-$C_{20}$ arylsulfonamido group; and
$R^7$, $R^8$ and $R^9$ are each, independently, selected from the group consisting of hydrogen, cyano, nitro, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, and $C_2$-$C_{20}$ heterocyclic group.

In the second aspect, the present invention provides a kind of novel polyheterocyclic based compounds having the following structure IIa and IIb:

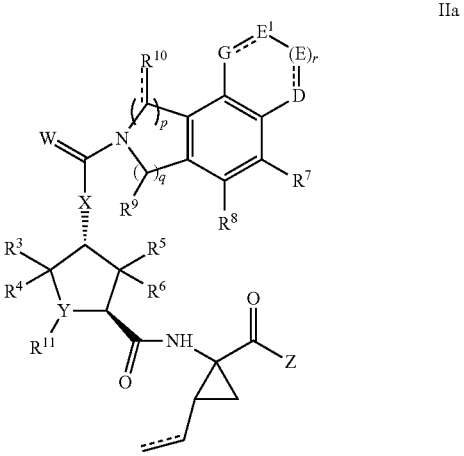

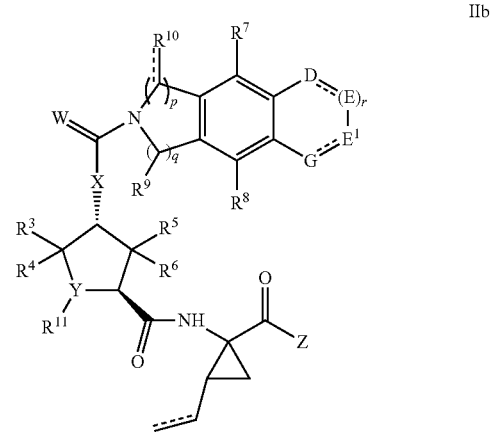

and/or its stereoisomers, solvates, hydrates, tautomers, esterification or amidation prodrugs, pharmaceutically acceptable salt, or mixtures thereof wherein:

p=0, 1 or 2;
q=0, 1 or 2;
r=0, 1, 2 or 3,
each dashed line "┅" is, independently, a single bond or double bond;
wherein when D and E are connected by a single bond, D and E are each, independently, selected from the group consisting of O, S, amino, and —C(Ra)(Rb)—; and $R^{10}$ is hydrogen, oxygen, halogen atom, cyano, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;
wherein when D and E are connected by a double bond, D and E each, independently, selected from the group consisting of N or —C(Rc)-;
wherein when $E^1$ and G are connected by a single bond, $E^1$ and G are each, independently, selected from the group consisting of O, S, amino, and —C(Ra)(Rb)—; and $R^{10}$ is hydrogen, oxygen, halogen atom, cyano, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;
wherein when $E^1$ and G are connected by a double bond, $E^1$ and G are each, independently, selected from the group consisting of N or —C(Rc)-;
wherein when the dashed line connecting $R^{10}$ to the macrocycle is a double bond, $R^{10}$ is O or S;
wherein when the dashed line connecting $R^{10}$ to the macrocycle is a single bond, $R^{10}$ is hydrogen, halogen atom, cyano, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;
Ra, Rb and Rc are each, independently, selected from the group consisting of hydrogen, halogen atom, cyano, nitro, $C_1$-$C_{20}$ alkyl, $C_3$-$C_{20}$ cycloalkyl, $C_6$-$C_{20}$ aryl, $C_1$-$C_{20}$ alkoxy, $C_1$-$C_{20}$ alkylthio, $C_1$-$C_{20}$ alkoxycarbonyl, $C_6$-$C_{20}$ aryloxy, $C_6$-$C_{20}$ aryloxycarbonyl, $C_2$-$C_{20}$ heterocyclic alkoxycarbonyl, $C_2$-$C_{20}$ heterocyclic aryl, $C_1$-$C_{20}$ alkylamino, $C_2$-$C_{20}$ heterocyclic amino, $C_6$-$C_{20}$ aryl amino, $C_1$-$C_{20}$ aminocarbonyl, $C_1$-$C_{20}$ amido, $C_1$-$C_{20}$ amidocarbonyl, $C_1$-$C_{20}$ carbonylamino, $C_1$-$C_{20}$ alkylsulfonamido, $C_2$-$C_{20}$ heterocyclic sulfonamido, $C_6$-$C_{20}$ arylsulfonamido, and $C_1$-$C_{20}$ aminosulfonamido group;
wherein when r=0, E is nothing, and the D group is directly linked to the $E^1$ group;
W is O or S;
X is O, S or —NRa—, wherein Ra is defined above;
Y is N or CH;
Z is hydroxyl, $C_1$-$C_{20}$ alkyl, $C_3$-$C_{20}$ cycloalkyl, $C_1$-$C_{20}$ alkoxy, $C_3$-$C_{20}$ cycloalkoxy, $C_1$-$C_{20}$ alkylamino, $C_3$-$C_{20}$ cycloalkylamino, $C_2$-$C_{20}$ heterocyclic amino, $C_6$-$C_{20}$ aryl, $C_6$-$C_{20}$ arylamino, $C_4$-$C_{20}$ heteroarylamino, $C_1$-$C_{20}$ alkyl sulfonamido, $C_3$-$C_{20}$ cycloalkylsulfonamido, $C_6$-$C_{20}$ arylsulfonamido, $C_1$-$C_{20}$ alkoxy sulfonamido, $C_3$-$C_{20}$ cycloalkoxy sulfonamido, $C_1$-$C_{20}$ alkylamino sulfonamido, $C_3$-$C_{20}$ cycloalkylamino sulfonamido, $C_6$-$C_{20}$ arylamino sulfonamido, $C_1$-$C_{20}$ uramido, $C_1$-$C_{20}$ thioureido, $C_1$-$C_{20}$ phosphate, or $C_1$-$C_{20}$ borate;
$R^1$ and $R^2$ are each, independently, selected from the group consisting of hydrogen, hydroxyl, amino, $C_1$-$C_2$ alkyl, $C_3$-$C_{20}$ cycloalkyl, $C_1$-$C_{20}$ alkoxy, $C_3$-$C_{20}$ cycloalkoxy, $C_1$-$C_{20}$ alkoxycarbonyl, $C_1$-$C_{20}$ alkylamino, $C_3$-$C_{20}$ cycloalkylamino, $C_2$-$C_{20}$ heterocyclic amino, $C_6$-$C_{20}$ arylamino, $C_1$-$C_{20}$ alkoxycarbonylamino, $C_6$-$C_{20}$ aryloxycarbonylamino, $C_1$-$C_{20}$ alkylsulfonamido, $C_3$-$C_{20}$ cycloalkylsulfonamido, $C_2$-$C_{20}$ heterocyclic sulfonamido, $C_6$-$C_{20}$ arylsulfonamido, and $C_1$-$C_{20}$ aminosulfonamido group;
$R^3$, $R^4$, $R^5$ and $R^6$ are each, independently, selected from the group consisting of hydrogen, halogen, hydroxyl, cyano, nitro, $C_1$-$C_{20}$ alkyl, $C_3$-$C_{20}$ cycloalkyl, $C_1$-$C_{20}$ alkoxy, $C_1$-$C_{20}$ alkylamino, $C_2$-$C_{20}$ heterocyclicamino, $C_6$-$C_{20}$ aryl, $C_6$-$C_{20}$ arylamino, $C_1$-$C_{20}$ alkylsulfonamido, $C_2$-$C_{20}$ heterocyclic sulfonamido, and $C_6$-$C_{20}$ arylsulfonamido group; and
$R^7$, $R^8$ and $R^9$ are each, independently, selected from the group consisting of hydrogen, cyano, nitro, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, and $C_2$-$C_{20}$ heterocyclic group; and
$R^{11}$ is hydrogen, $C_1$-$C_{20}$ alkyl, $C_1$-$C_{20}$ alkylcarbonyl, $C_1$-$C_{20}$ alkoxycarbonyl, $C_1$-$C_{20}$ aminocarbonyl, $C_6$-$C_{20}$ aryl, $C_6$-$C_{20}$ arylcarbonyl, $C_6$-$C_{20}$ aryloxycarbonyl, $C_1$-$C_{20}$ alkylsulfonamido, $C_6$-$C_{20}$ arylsulfonamido, $C_1$-$C_{20}$ aminosulfonamido, $C_2$-$C_{20}$ heterocyclic group.

In the third aspect, the present invention provides a kind of novel polyheterocyclic based compounds having the following structure Va and Vb:

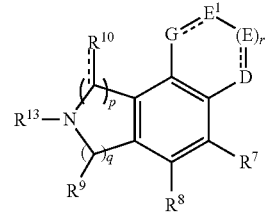

Va

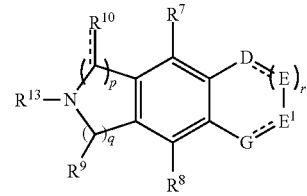

Vb wherein:
p=0, 1 or 2;
q=0, 1 or 2;
r=0, 1, 2 or 3;
each dashed line "┅" is, independently, a single bond or double bond;
wherein when D and E are connected by a single bond, D and E are each, independently, selected from the group consisting of O, S, amino, and —C(Ra)(Rb)—; and $R^{10}$ is hydrogen, oxygen, halogen atom, cyano, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;
wherein when D and E are connected by a double bond, D and E each, independently, selected from the group consisting of N or —C(Rc)-;
wherein when $E^1$ and G are connected by a single bond, $E^1$ and G are each, independently, selected from the group consisting of O, S, amino, and —C(Ra)(Rb)—; and $R^{10}$ is hydrogen, oxygen, halogen atom, cyano, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;

wherein when $E^1$ and G are connected by a double bond, $E^1$ and G are each, independently, selected from the group consisting of N or —C(Rc)-;

wherein when the dashed line connecting $R^{10}$ to the macrocycle is a double bond, $R^{10}$ is O or S;

wherein when the dashed line connecting $R^{10}$ to the macrocycle is a single bond, $R^{10}$ is hydrogen, halogen atom, cyano, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, or $C_2$-$C_{20}$ heterocyclic group;

Ra, Rb and Rc are each, independently, selected from the group consisting of hydrogen, halogen atom, cyano, nitro, $C_1$-$C_{20}$ alkyl, $C_3$-$C_{20}$ cycloalkyl, $C_6$-$C_{20}$ aryl, $C_1$-$C_{20}$ alkoxy, $C_1$-$C_{20}$ alkylthio, $C_1$-$C_{20}$ alkoxycarbonyl, $C_6$-$C_{20}$ aryloxy, $C_6$-$C_{20}$ aryloxycarbonyl, $C_2$-$C_{20}$ heterocyclic alkoxycarbonyl, $C_2$-$C_{20}$ heterocyclic aryl, $C_1$-$C_{20}$ alkylamino, $C_2$-$C_{20}$ heterocyclic amino, $C_6$-$C_{20}$ aryl amino, $C_1$-$C_{20}$ aminocarbonyl, $C_1$-$C_{20}$ amido, $C_1$-$C_{20}$ amidocarbonyl, $C_1$-$C_{20}$ carbonylamino, $C_1$-$C_{20}$ alkylsulfonamido, $C_2$-$C_{20}$ heterocyclic sulfonamido, $C_6$-$C_{20}$ arylsulfonamido, and $C_1$-$C_{20}$ aminosulfonamido group;

wherein when r=0, E is nothing, and the D group is directly linked to the $E^1$ group;

$R^7$, $R^8$ and $R^9$ are each, independently, selected from the group consisting of hydrogen, cyano, nitro, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, and $C_2$-$C_{20}$ heterocyclic group; and $R^{13}$ is hydrogen, $C_1$-$C_{20}$ alkyl, $C_1$-$C_{20}$ alkylcarbonyl, $C_1$-$C_{20}$ alkoxycarbonyl, $C_1$-$C_{20}$ cycloalkoxycarbonyl, $C_1$-$C_{20}$ aminocarbonyl, $C_6$-$C_{20}$ aryl, $C_6$-$C_{20}$ arylcarbonyl, $C_6$-$C_{20}$ aryloxycarbonyl, $C_1$-$C_{20}$ alkylsulfonyl, $C_6$-$C_{20}$ arylsulfonyl, $C_1$-$C_{20}$ aminosulfonyl, or $C_2$-$C_{20}$ heterocyclic group.

The fourth aspect of the present invention provides a pharmaceutical composition comprising one or more compounds selected from the structure Ia-Ib or IIa-IIb.

The fifth aspect of the present invention provides a pharmaceutical combination of any one or more compounds of the structure Ia-Ib or in a therapeutically effective dose and/with a second or a third medicament in a therapeutically effective dose. Thus, the present invention provides a pharmaceutical composition, comprising at least one compound described above in a therapeutically effective dose and at least one additional medicament in a therapeutically effective dose The sixth aspect of the present invention provides a pharmaceutical combination of any compound of the structure Ia-Ib or IIa-IIb and/with any HIV inhibitor including but not limited to Ritonavir. Thus, the present invention provides a A pharmaceutical composition, comprising at least one compound described above in a therapeutically effective dose and at least one HIV inhibitor in a therapeutically effective dose.

The seventh aspect of the present invention provides a pharmaceutical combination of at least one compound described above and any hepatitis B virus (HBV) inhibitor including but not limited to Heptodin, Sebivo, Hepsera, Emtriva, Baraclude, or Viread.

The eighth aspect of the present invention provides a method for inhibiting HCV by using one or more compounds of the structure Ia-Ib or IIa-IIb in a therapeutically effective dose and a second or a third medicament in a therapeutically effective dose. Thus, the present invention provides a method of inbibiting HCV, comprising administering an effect amount of a compound or composition described above to a subject in need thereof.

The ninth aspect of the present invention provides a method for inhibiting HCV by using one or more compounds of the structure Ia-Ib or IIa-IIb and in combination with any or combined one or more of (1) Immune modulators including but not limited to Interferons, pegulated-interferons, or interferon derivatives, (2) HCV protease inhibitors, (3) HCV polymerase inhibitors, (4) nucleosides and its derivatives, (5) Cyclophilin inhibitors, (6) Glucosidase I inhibitors, (7) IMPDH inhibitors, (8) Caspase inhibitors, (9) TLR agonists, (10) HIV inhibitors, (11) anti-inflammatory drugs, (12) Cancer drugs, or (13) other compounds not covered from above (1)-(12).

Overall, furthermore, all prepared new polyheterocyclic based compounds have been evaluated for their potency in vitro and in vivo, and the present invention explores the relationship between the structures of new polyheterocyclic compounds and efficacy of HCV inhibition and provides valuable clue and potential HCV inhibitors.

DETAILED DESCRIPTION OF THE INVENTION

Details of the present invention are set forth in the following description for preparation and biological activity study of new HCV inhibitors Ia-Ib and IIa-IIb. The advantages of the present invention will be significantly observed from the following detailed description.

As used herein, the term "alkyl" refers to any linear or branched chain alkyl group having a number of carbon atoms and/or "alkylene" in the specified range, wherein one or more hydrogens could be replaced by one or more halogens.

The term "alkoxy" refers to an "alkyl-O—" group.

The term "cycloalkyl" refers to any cyclic ring of an alkane or alkene having a number of carbon atoms and/or "alkylene" in the specified range, wherein one or more hydrogens could be replaced by one or more halogens.

The term "halogen" (or "halo") refers to fluorine, chlorine, bromine and iodine atoms (or referred as fluoro, chloro, bromo, and iodo).

The term "carbonyl" refers to an "—C(O)—" group.

The term "alkyl carbonyl" refers to an "alkyl-C(O)—" group.

The term "alkoxy carbonyl" refers to an "alkyl-O—C(O)—" group.

The term "alkylamino carbonyl" refers to an "alkyl-NH—C(O)—" or "dialkyl-N—C(O)—" group. The term "sulfonamido" refers to an "—S(O)$_2$NH—" or "—S(O)$_2$N(R)—" group, wherein R is alkyl or alkylcarbonyl group.

The term "alkyl sulfonamido" refers to an "alkyl—S(O)$_2$NH—" or "alkyl—S(O)$_2$N(R)—" group, wherein R is alkyl or alkylcarbonyl group.

The term "alkoxy sulfonamido" refers to an "alkyl-O—S(O)$_2$NH—" or "alkyl-O—S(O)$_2$N(R)—" group, wherein R is alkyl or alkylcarbonyl group.

The term "polyheterocyclic" refers to a tri-cyclic or tetra-cyclic functional group with 1-5 hetero atoms (e.g., O, N, S, and P) in one or more fused rings.

The term "composition" is intended to encompass a product comprising the specified ingredients, as well as any product which results, directly or indirectly, from combining the specified ingredients.

The term "pharmaceutically acceptable" means that the ingredients of the pharmaceutical composition must be compatible with each other and not deleterious to the recipient thereof.

The term "effective amount" means that amount of active compound or pharmaceutical agent that elicits the biological or medicinal response in a tissue, system, animal or human that is being sought by a researcher, veterinarian, medical doctor or other clinician. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

The present invention provides two classes of novel polyheterocyclic based compounds Ia-Ib and IIa-IIb, and pharmaceutically acceptable salts, and/or hydrates as HCV NS3 protease inhibitors with high potency. Moreover, toxicity study is determined to be non-toxic ($LD_{50} > 10,000$) for most of highly potent HCV inhibitors.

Synthesis of new polyheterocyclic based compounds with general structure Ia-Ib and IIa-IIb: Using previously published and the synthetic methods described herein, different kinds of synthetic methods have been carried out effectively to prepare different compounds with the structure Ia-Ib and IIa-IIb.

In the present invention, compounds VIa-VIf are prepared first as in the following Scheme 1:

Scheme 1:

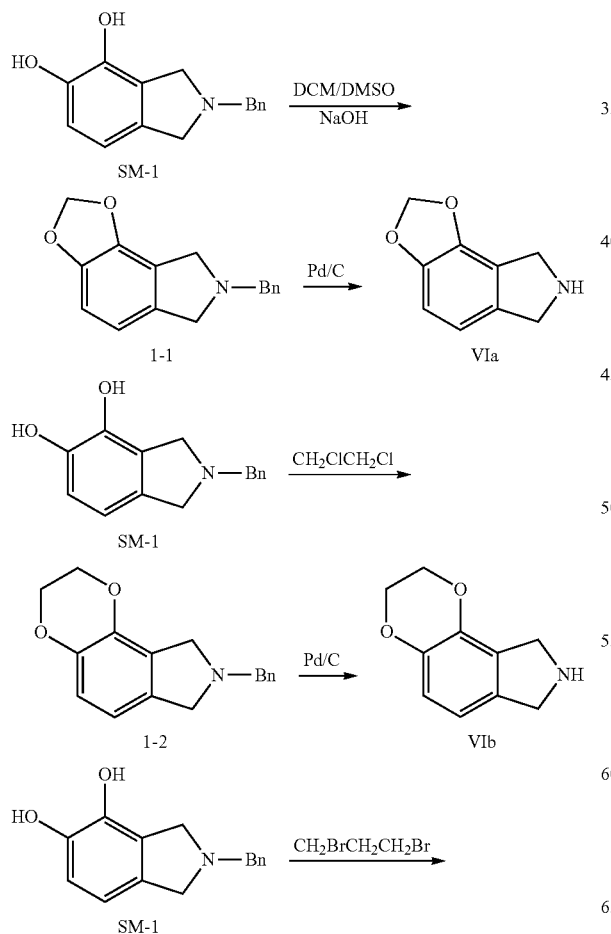

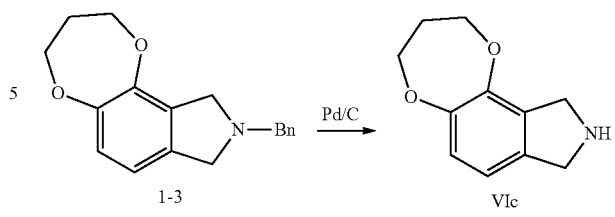

In Scheme 1, in the presence of inorganic base (e.g., sodium hydroxide, sodium methoxide, or sodium hydrogen), SM-1 was dissolved in organic solvents (methanol, THF, DMF, or DMSO) and heated to 30-120° C., then reacted with $ClCH_2Cl$, $ClCH_2CH_2Cl$, or $BrCH_2CH_2CH_2Br$, respectively, to form five, six, or seven membered polyheterocyclic compound 1-1, 1-2, or 1-3, followed by deprotection to obtain the key tri-heterocyclic compounds VIa-VIc by removing the protecting group (Bn: benzyl) with Pd/C catalyst and hydrogen in methanol or ethanol.

Scheme 2:

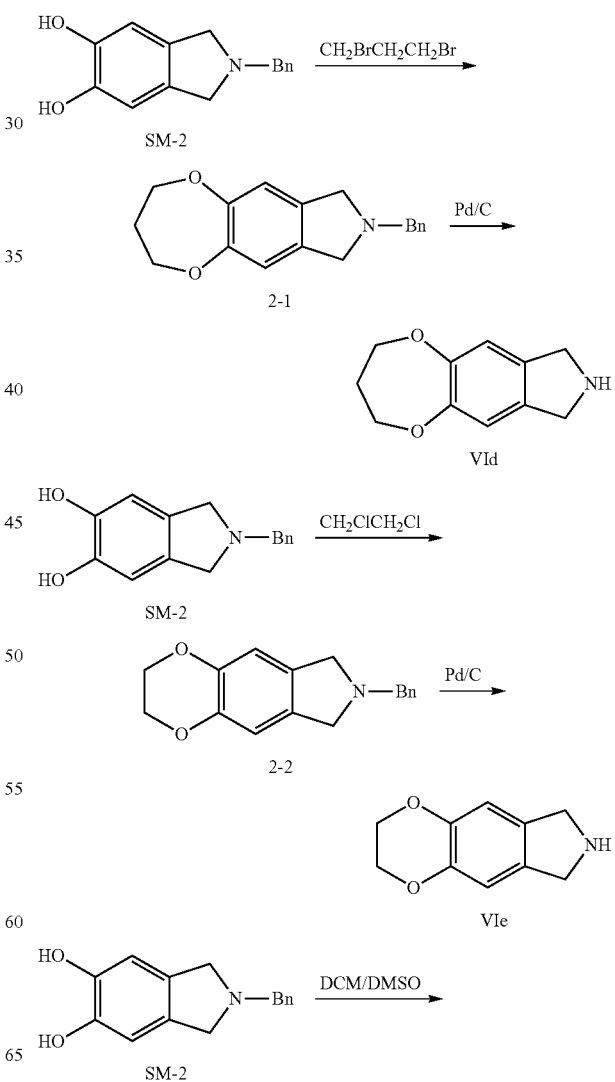

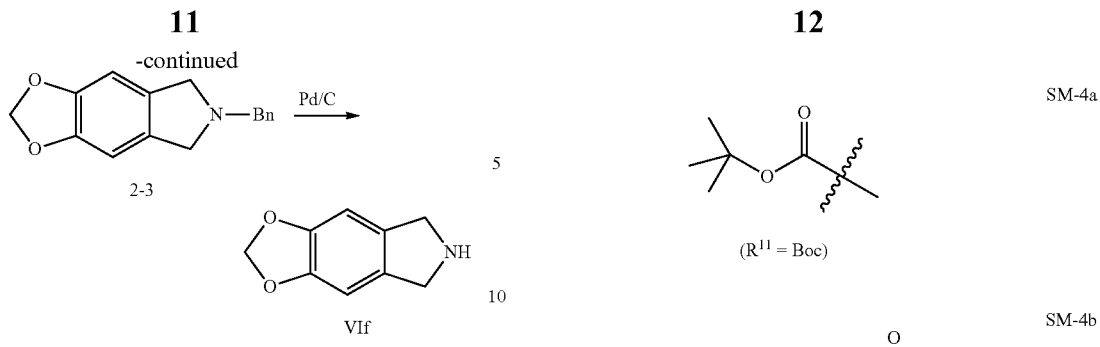

In Scheme 2, SM-2 was dissolved in organic solvents (methanol, THF, DMF, or DMSO) and heated to 30-120° C., then reacted with $BrCH_2CH_2CH_2Br$, $ClCH_2CH_2Cl$ or $ClCH_2Cl$, respectively, to form seven, six or five membered polyheterocyclic compound 2-1, 2-2, or 2-3, followed by deprotection to obtain the key tri-heterocyclic compounds VId-VIf by removing the protecting group (Bn: benzyl) with Pd/C catalyst and hydrogen in methanol or ethanol.

Preparation of the following specific compounds IIIa-IIIb has been carried out as follows in Scheme 3.

In the presence of coupling reagent CDI, starting material SM-4 (e.g., SM-4a or SM-4b) was reacted with compounds VIa-VIf, respectively to obtain polyheterocyclic compounds 4a-4h and 6a-6d (IIIa-IIIb) as shown below amidation reaction.

Scheme 3:

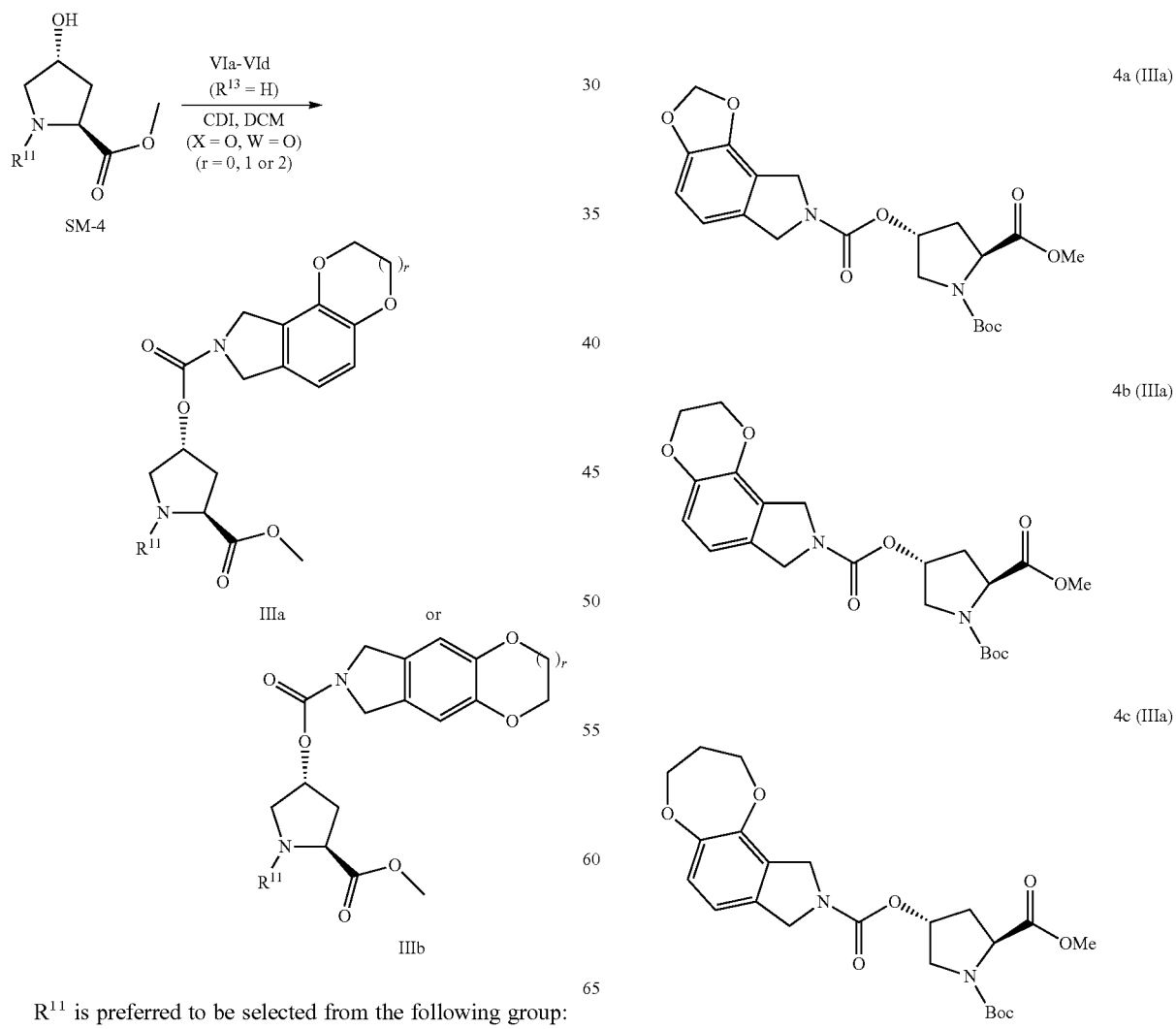

$R^{11}$ is preferred to be selected from the following group: SM-4a (Boc) or SM-4b:

13
-continued
14
-continued
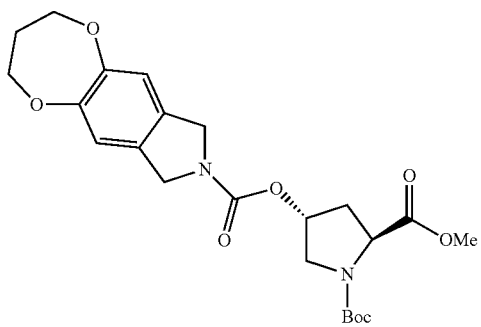
4d (IIIb)
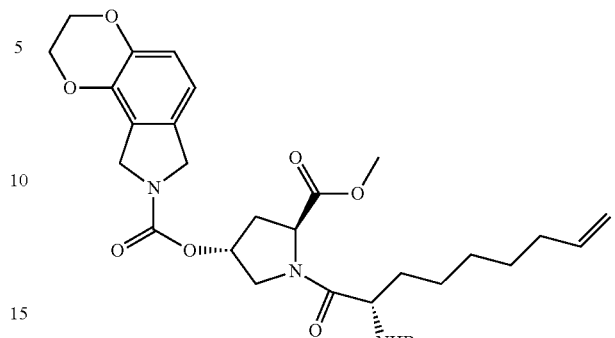
6b
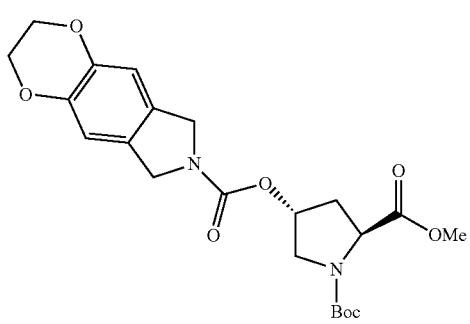
4e (IIIb)
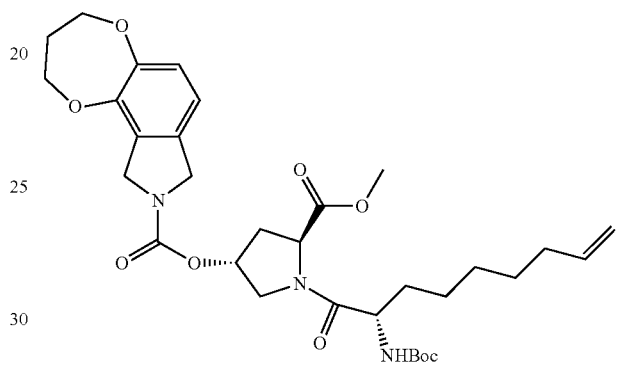
6c
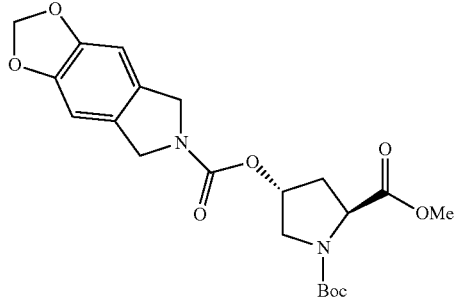
4f(IIIb)
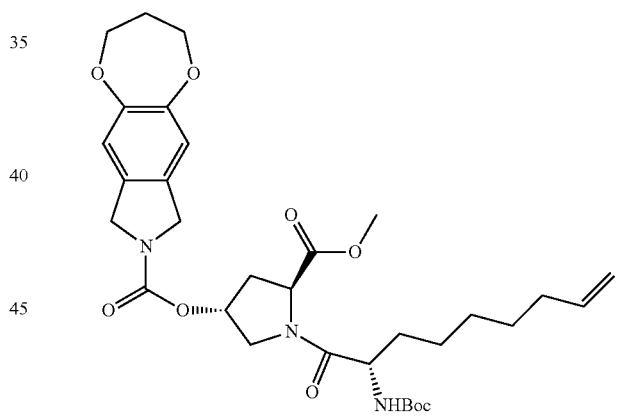
6d
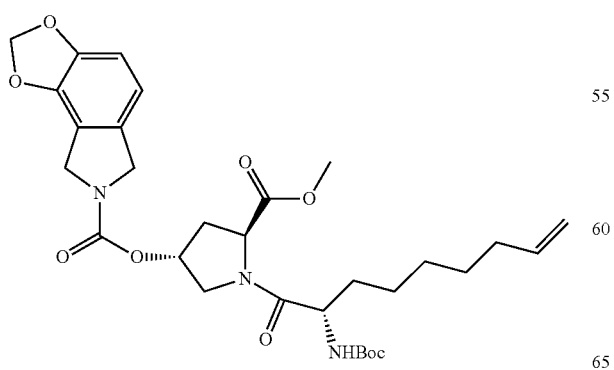
6a
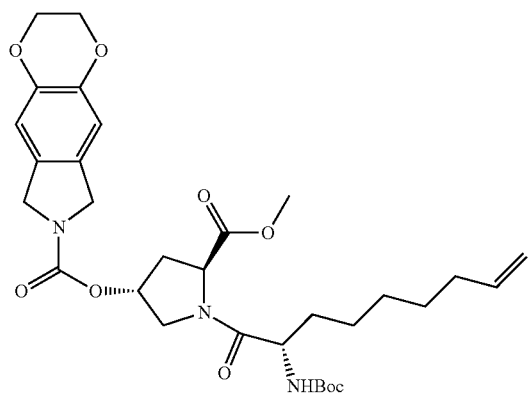
6e -continued
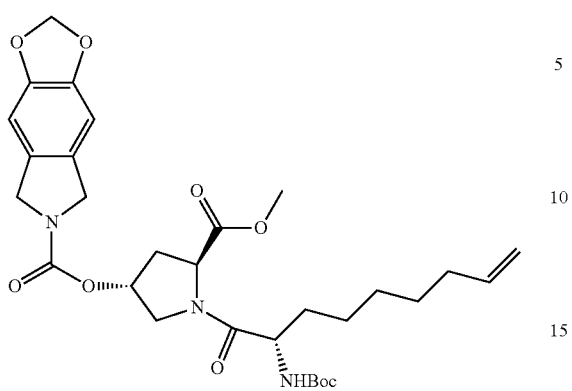
6f
After the key intermediates 4a-4f and 6a-6f were prepared, there were several synthetic methods developed as in Schemes 4-11 for preparation of different kinds of new HCV inhibitors. The detail for each reaction condition and analytical results of products is listed in the detailed examples.
Scheme 4:
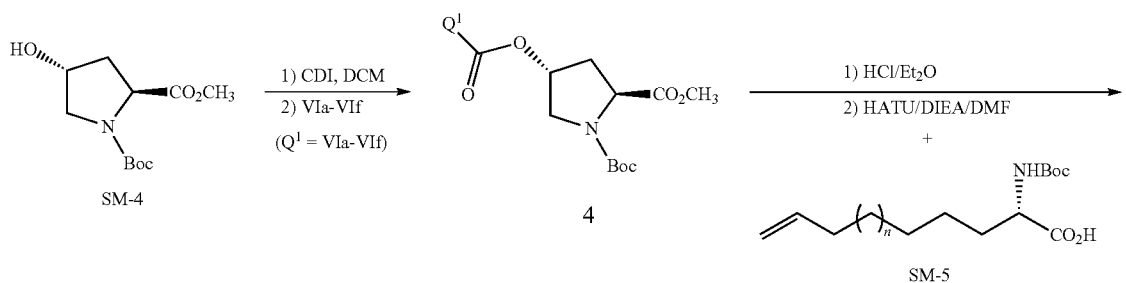
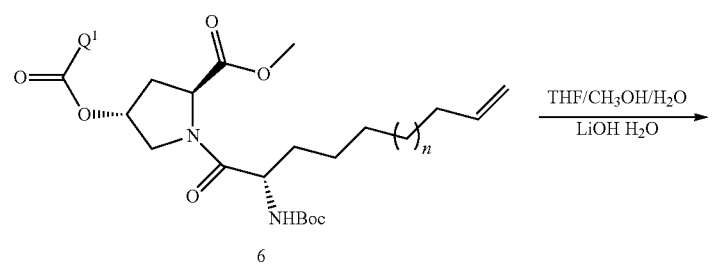
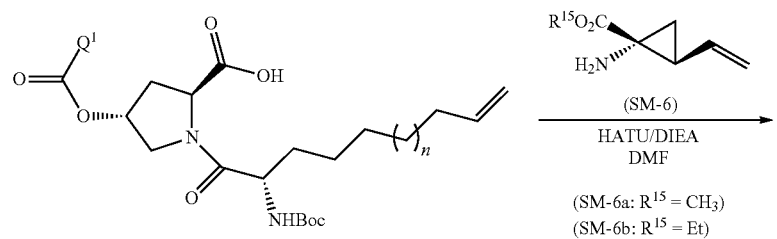

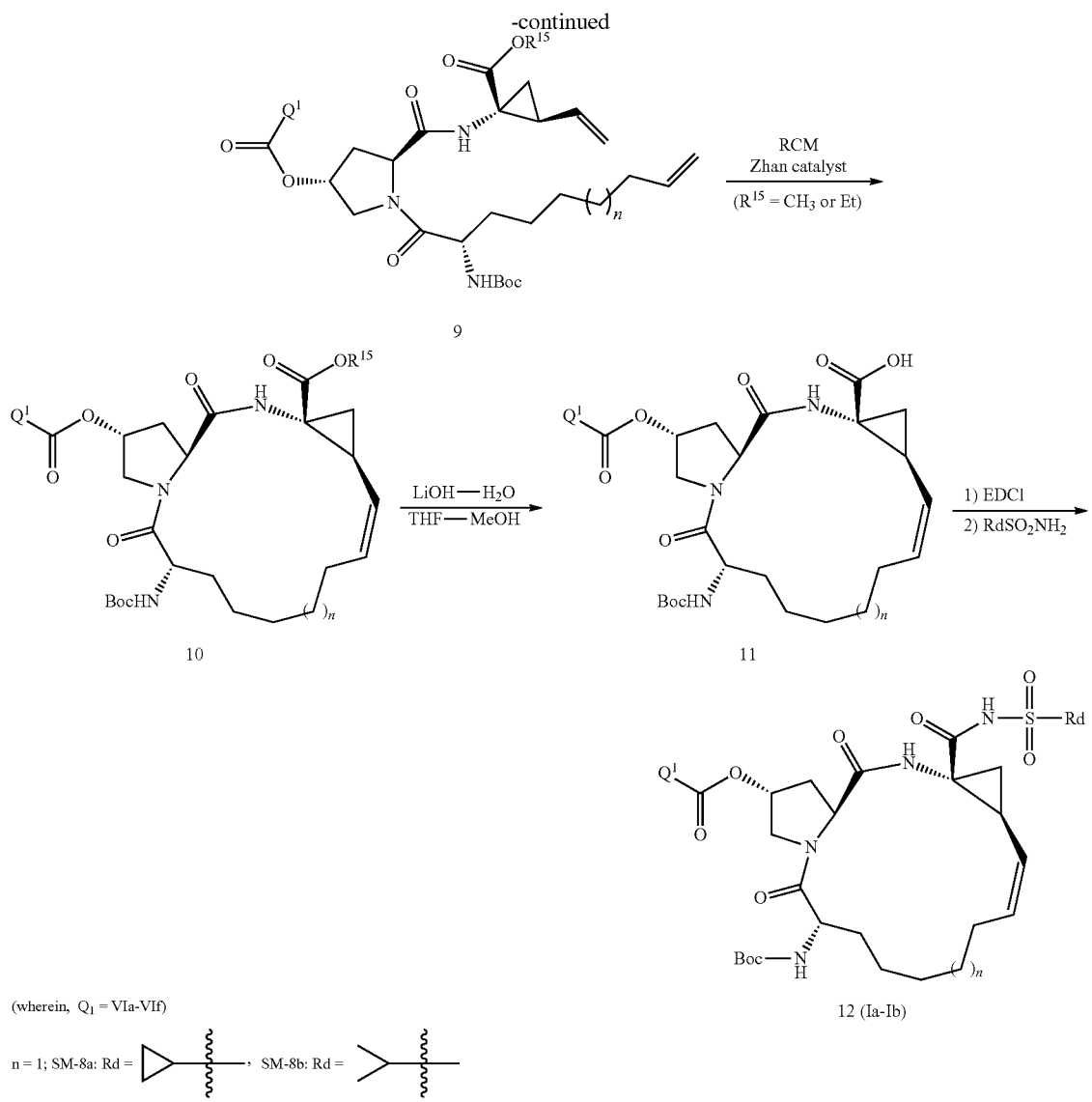

(wherein, $Q_1$ = VIa-VIf)

n = 1; SM-8a: Rd = ▷ ; SM-8b: Rd = ⊳

In Scheme 4 above, the product 4 (e.g., compounds 4a-4f and 6a-6f) prepared as shown in Scheme 3 was deprotected to obtain an intermediate carboxylic acid (5) by removing HCl group, followed by amidation with an N-Boc protected amino acid SM-5 to form compound 6 in the presence of coupling reagent HATU. After hydrolysis of compound 6 in LiOH-Water/MeOH solution, another carboxylic acid (7) was obtained, and followed by amidation with another amino acid (methyl or ethyl ester) SM-6 in the presence of coupling reagent HATU to form product 9 (e.g., compounds 9a-9f shown below). In anhydrous oxygen-free organic solvents (DCM, DCE, or toluene), Diene 9 intermediate was carried out an olefin ring-closing metathesis (RCM) reaction in the presence of metathesis catalyst (e.g., Zhan catalyst-1 or Zhan catalyst-1B used in this invention) at 20-80□ to form 14-16 membered macrocyclic olefin-linked product 10, then the methyl/ethyl ester was hydrolyzed with LiOH in water-MeOH solution to offer a new carboxylic acid 11. Finally, in the presence of a coupling reagent such as EDCI or HATU, the carboxylic acid 11 reacted with different kinds of alkyl-sulfonamide, cycloalkylsulfonamide or arylsulfonamide [RdS(O)$_2$NH$_2$], respectively, to form a series of novel poly-heterocyclic based macrocyclic compounds Ia-Ib, such as 12a-12xx shown below).

9a

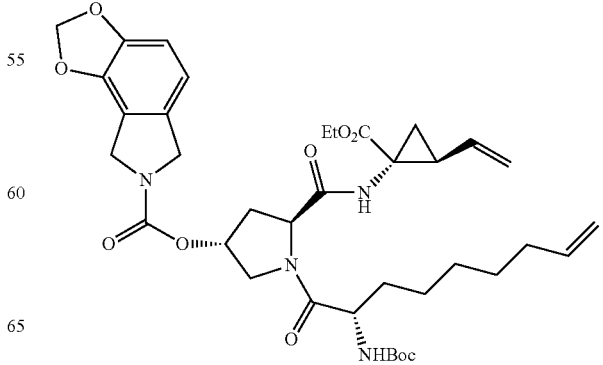

-continued
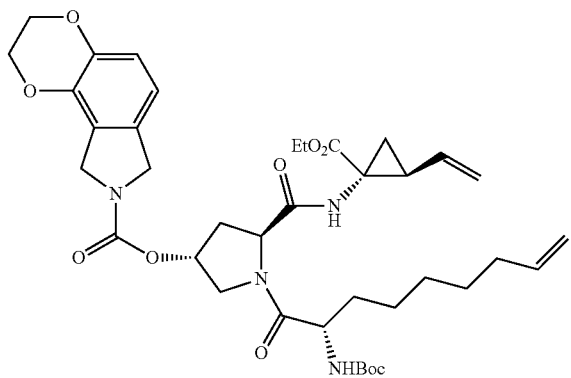
9b
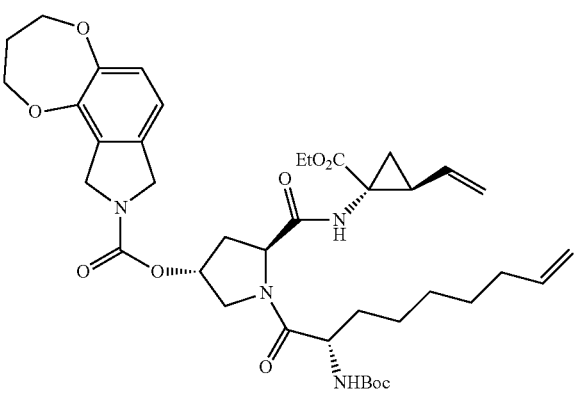
9c
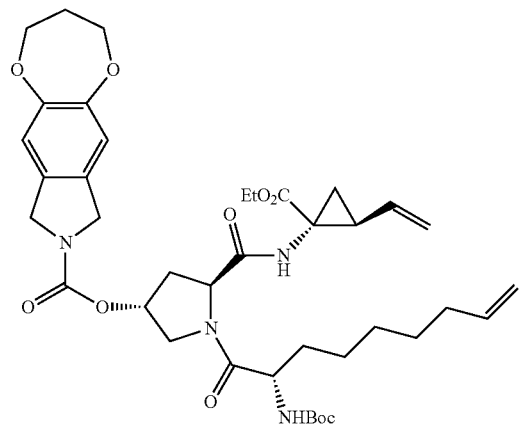
9d
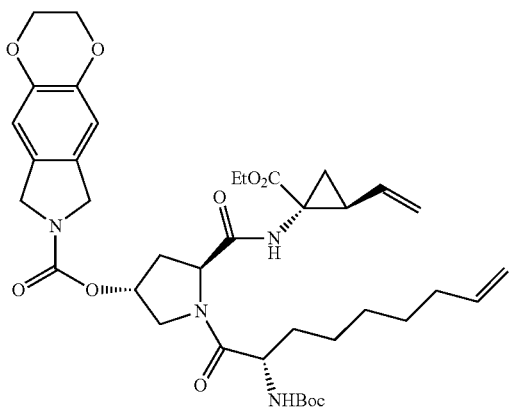
9e
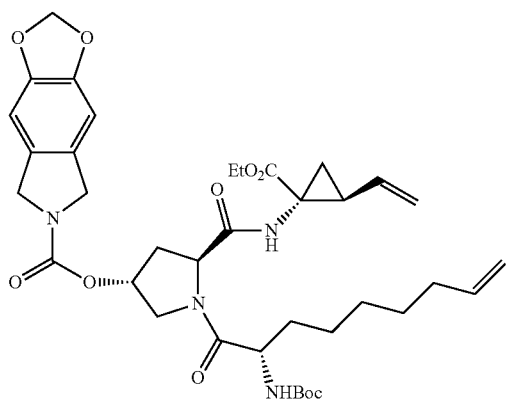
9f
The structure of Zhan catalysts (Zhan Catalyst-1 & 1B) used for RCM of diene intermediate 9 is shown below:
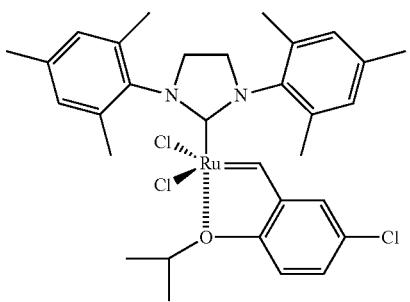
Zhan Catalyst-1
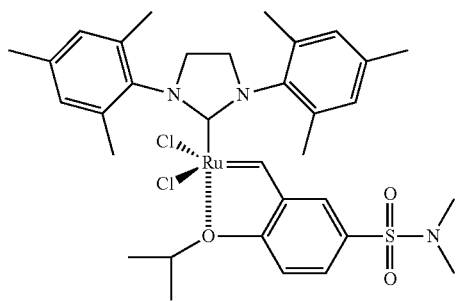
Zhan Catalyst-1B In order to obtain more compounds efficiently for potency screening, there is another alternative synthetic route developed effectively for preparation of different new macrocyclic compounds Ia-Ib in Scheme 5.

Scheme 5:

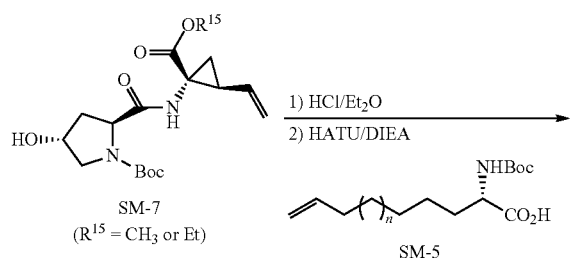

SM-7
($R^{15}$ = CH$_3$ or Et)

SM-5

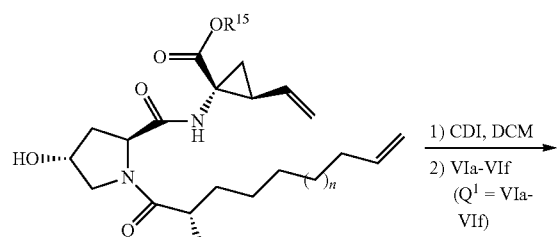

8

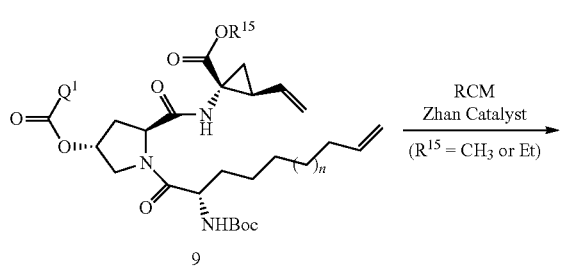

9

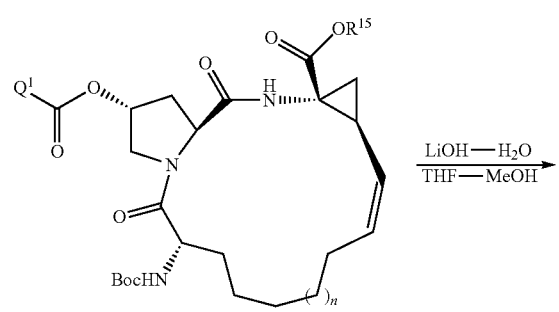

10

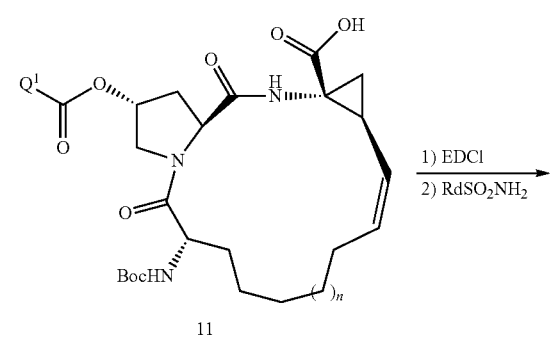

11

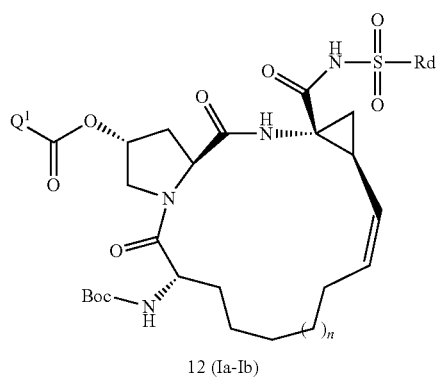

12 (Ia-Ib)

(wherein, $Q^1$ = VIa-VIf)

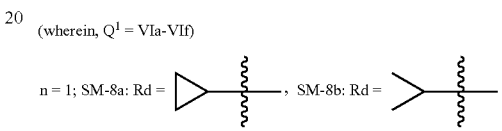

n = 1; SM-8a: Rd = , SM-8b: Rd =

In Scheme 5, first of all, the protecting group (Boc) in the starting material SM-7 was removed by HCl acid, followed by amidation with an N-Boc protected amino acid SM-5 to form compound 8 in the presence of coupling reagent HATU. In the presence of coupling reagent CDI, compound 8 was reacted with compounds VIa-VIf, respectively, to obtain polyheterocyclic compounds 9. In anhydrous oxygen-free organic solvents (DCM, DCE, or toluene), an olefin ring-closing metathesis (RCM) reaction was carried out for the diene 9 intermediate in the presence of metathesis catalyst (e.g., Zhan catalyst-1 or Zhan catalyst-1B used in this invention) at 20-80□ to form 14-16 membered macrocyclic olefin-linked product 10, then the methyl/ethyl ester was hydrolyzed with LiOH in water-MeOH solution to offer a new carboxylic acid 11 as shown below.

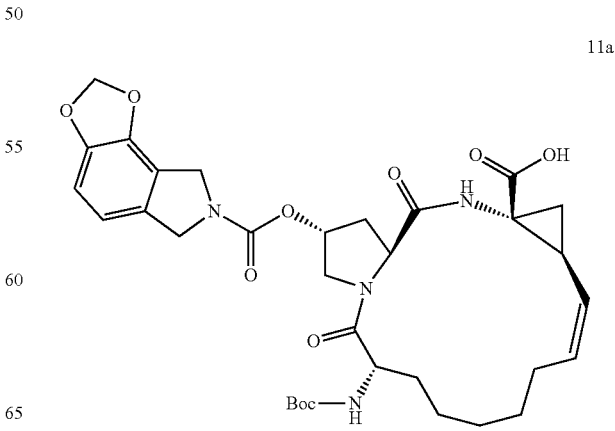

11a

11b

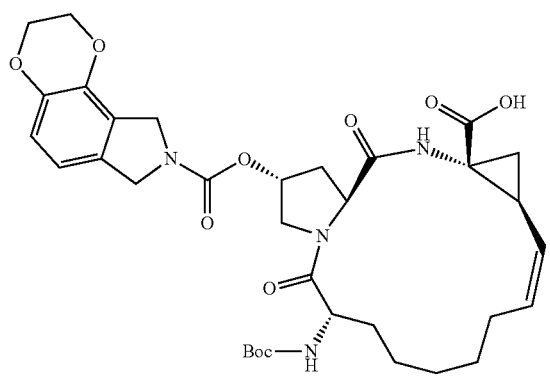

11c

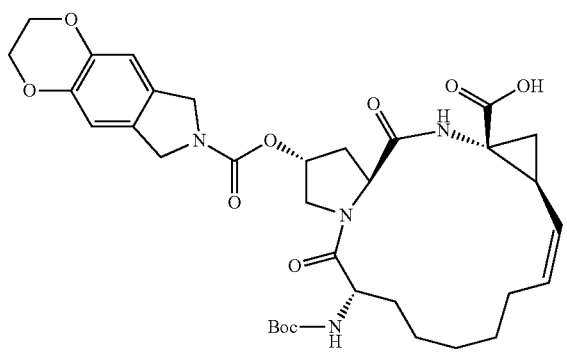

11d

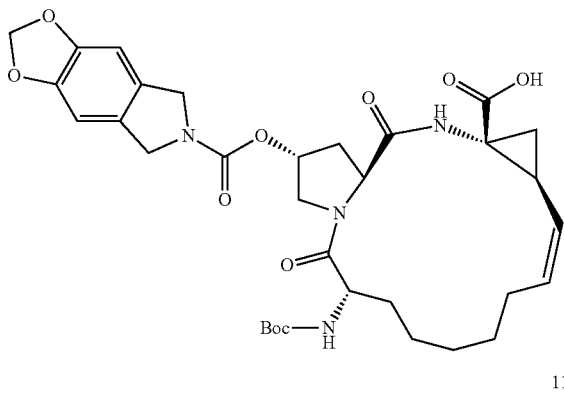

11j

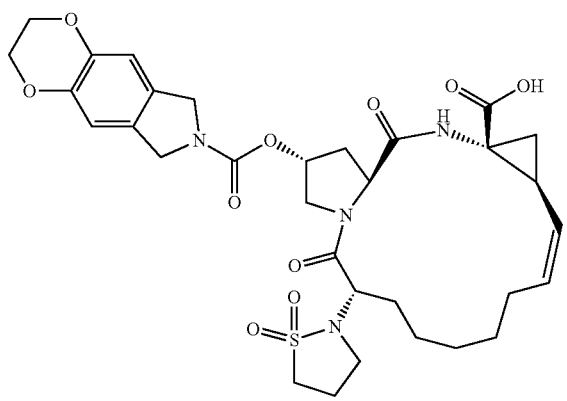

11k

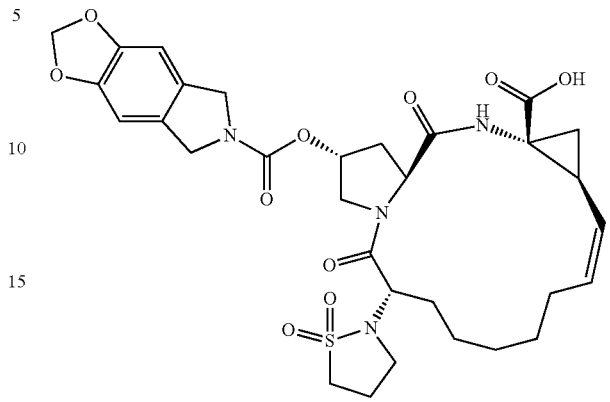

11m

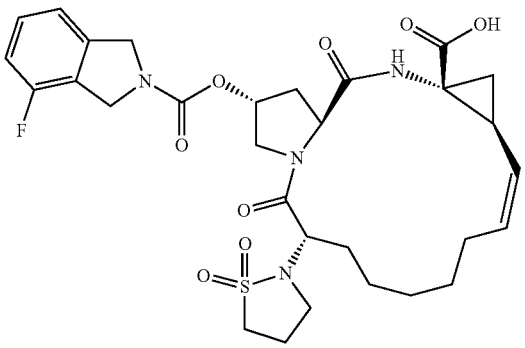

Finally, in the presence of a coupling reagent such as EDCI or HATU, the carboxylic acid product 11 reacted with different kinds of alkylsulfonamide, cycloalkylsulfonamide or arylsulfonamide [RdS(O)$_2$NH$_2$], respectively, to form a series of novel polyheterocyclic based macrocyclic compounds Ia-Ib.

In order to optimize efficacy and biological property of new HCV inhibitors, there are more structure modified compounds designed and synthesized in Schemes 6-11. In Scheme 6, there is a kind of cycloalkylsulfonamde products prepared for potency screening.

Scheme 6:

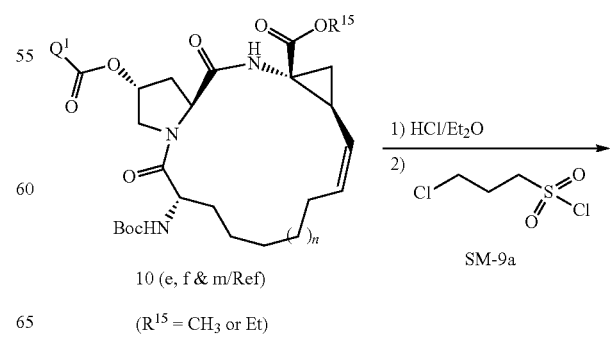

10 (e, f & m/Ref)

(R$^{15}$ = CH$_3$ or Et)

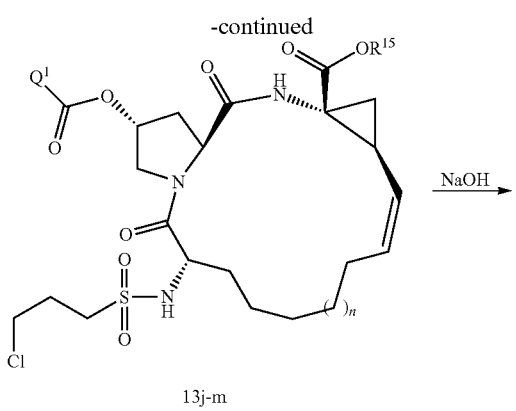

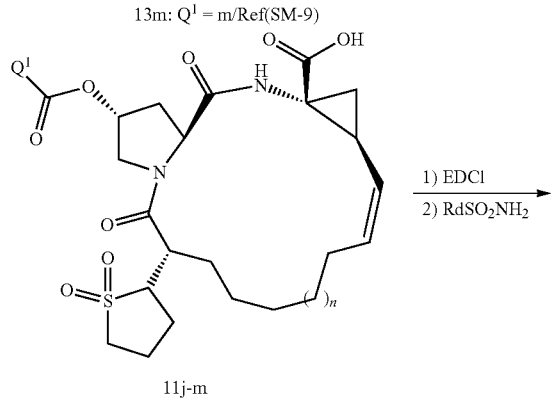

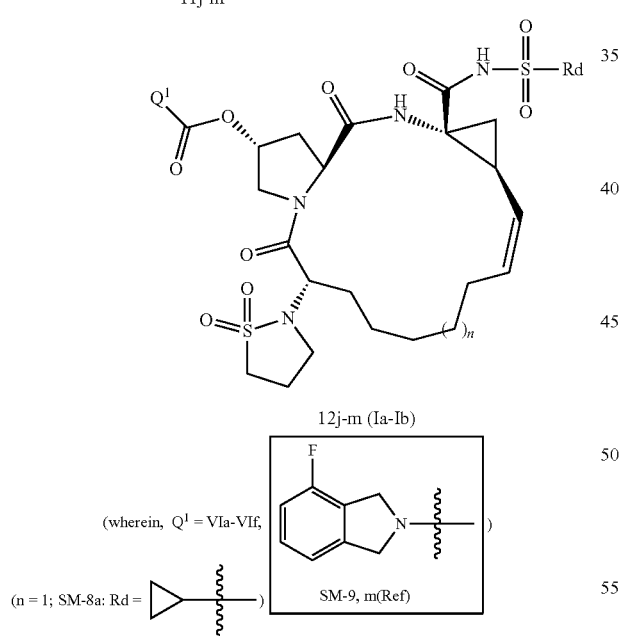

11j & 12j: Q¹ = VIe
11k & 12k: Q¹ = VIf
11m & 12m: Q¹ = m/Ref (SM-9)

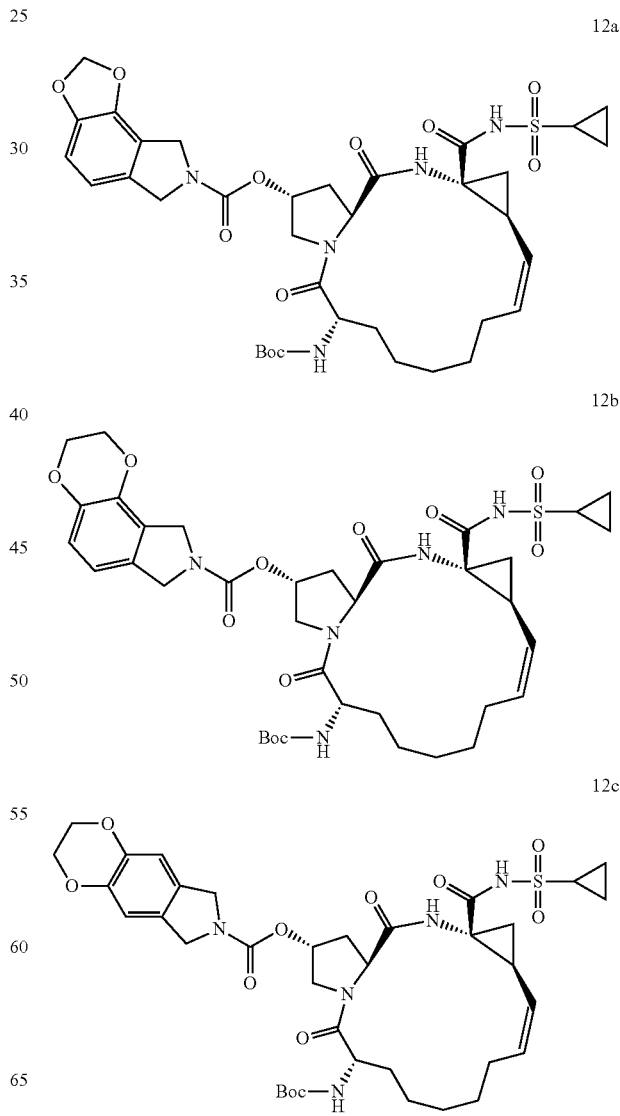

fonyl chloride reagent (RdSO₂Cl or R¹⁷SO₂Cl, SM-9) to obtain an alkylsulfonamide product 13. In the presence of inorganic base (e.g., NaOH or KOH), the intramolecular cyclization was conducted to form sulfonamide compound 11. Finally, in the presence of a coupling reagent such as EDCI or HATU, the carboxylic acid 11 reacted with different kinds of alkylsulfonamide, cycloalkylsulfonamide or arylsulfonamide [RdS(O)₂NH₂, SM-8], respectively, to form a series of novel polyheterocyclic based macrocyclic compounds Ia-Ib, such as 12j-12m as shown below. Furthermore, the compound 10c-d was deprotected first by removing Boc with HCl acid, followed by amidation with an alkylsulfonyl chloride reagent (RdSO₂Cl or R¹⁷SO₂Cl, SM-9) to obtain another kind of alkylsulfonamide product 13, then in the presence of a base (e.g., NaH or NaOMe), the alkylsulfonamide product 13 was reacted with another reagent $R^{16}$—Cl (or $R^{16}$—Br, SM-10) or (Boc)₂O to form another kind of new desired products Ia-Ib (12s-12u) as herein, wherein, $R^{16}$ is $C_1$-$C_6$ alkyl, $C_3$-$C_6$ cycloalkyl, $C_1$-$C_6$ alkoxycarbonyl, $C_3$-$C_6$ cycloalkoxycarbonyl, $C_6$-$C_{10}$ aryl, $C_6$-$C_{10}$ arylcarbonyl, $C_6$-$C_{10}$ aryloxycarbonyl or $C_2$-$C_{10}$ heterocyclic group.

In Scheme 6 above, the compound 10c-d prepared in Schemes 4 and 5 were used for deprotection first by removing Boc with HCl acid, followed by amidation with an alkylsul- 27
-continued
12d
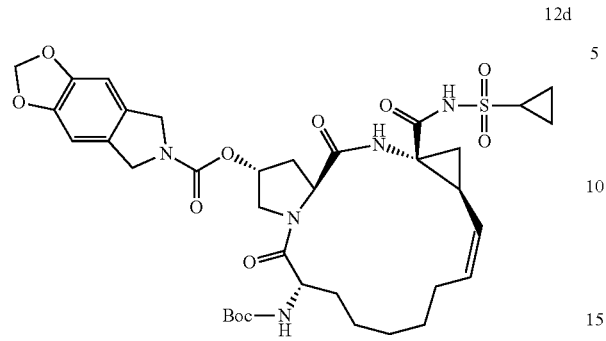
12e
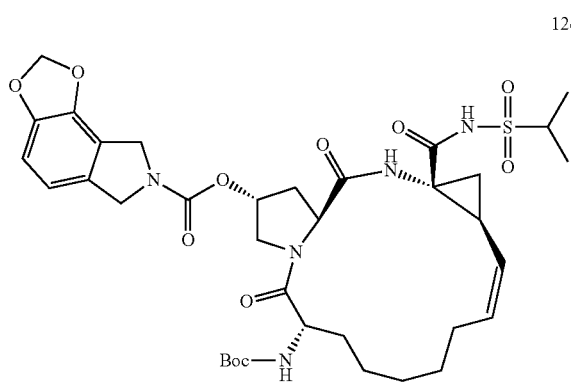
12f
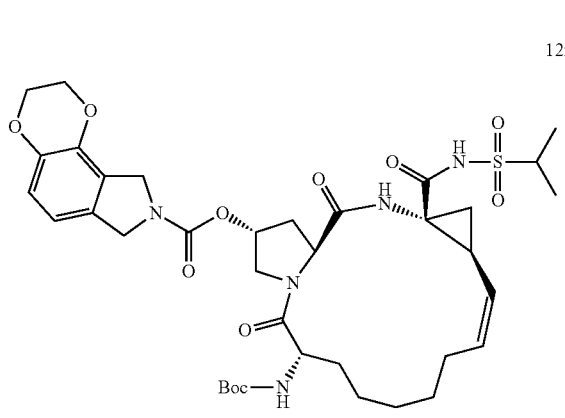
12g
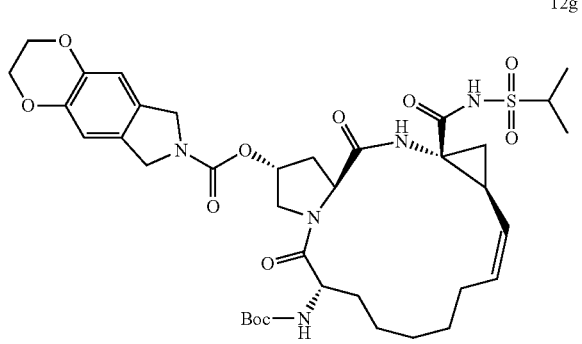
28
-continued
12h
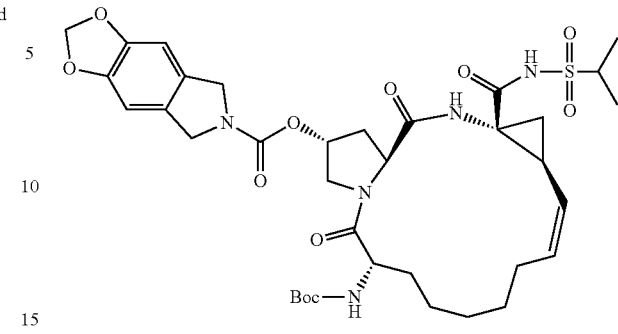
12j
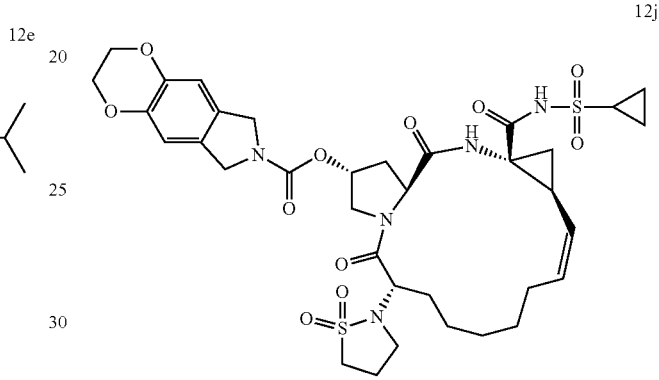
12k
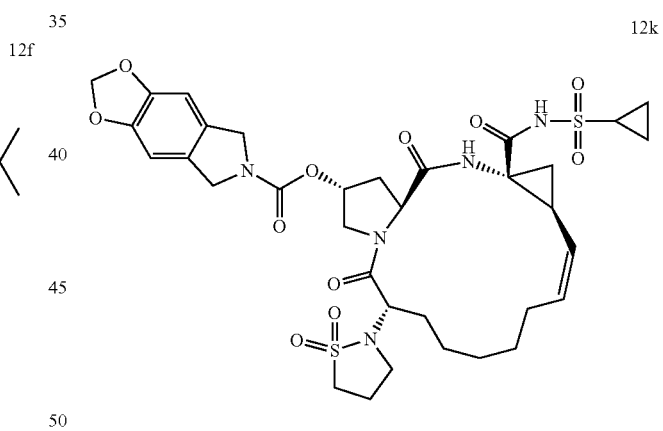
12m
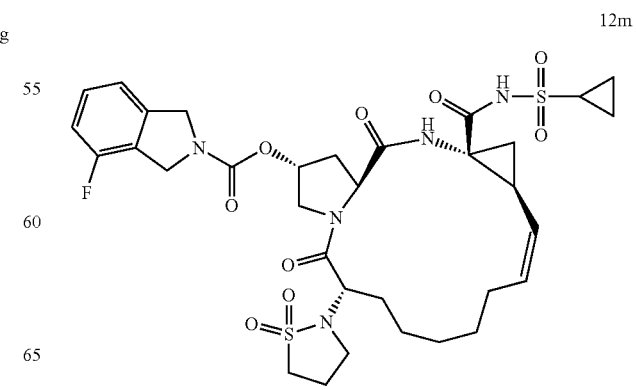

12n

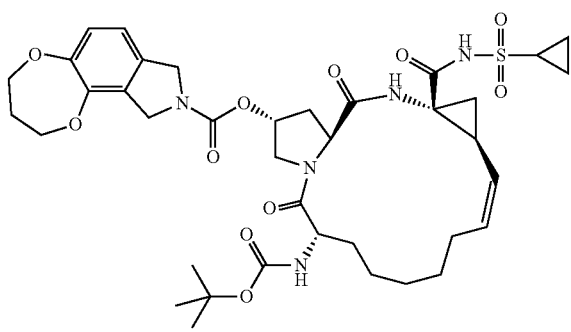

12s

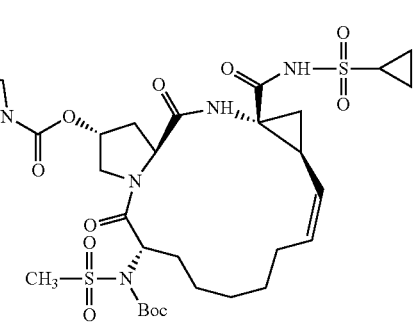

12p

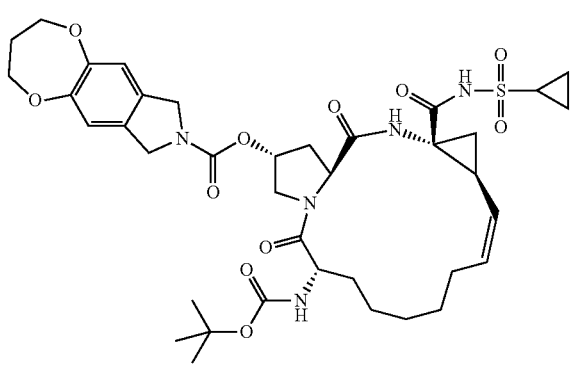

12t

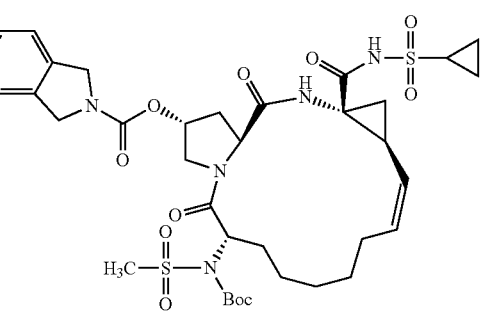

12q

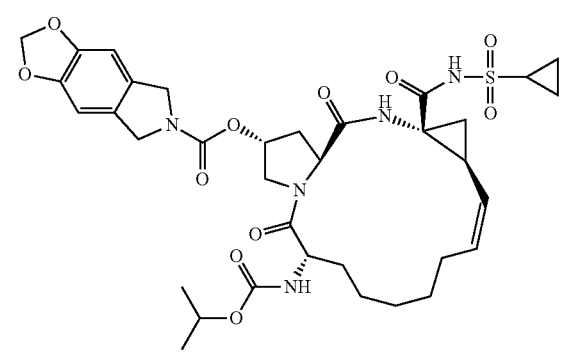

12-u

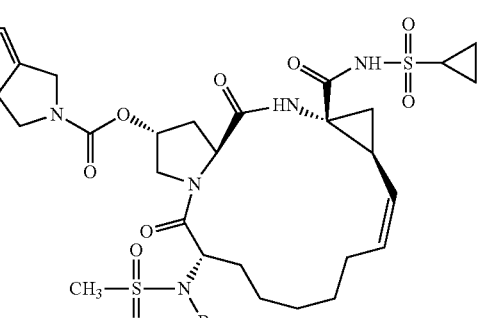

12-Ref Compound (ITMN-191)

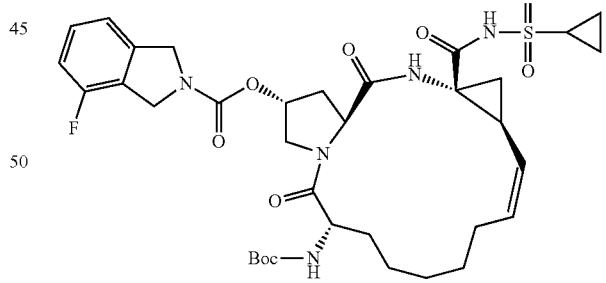

12r

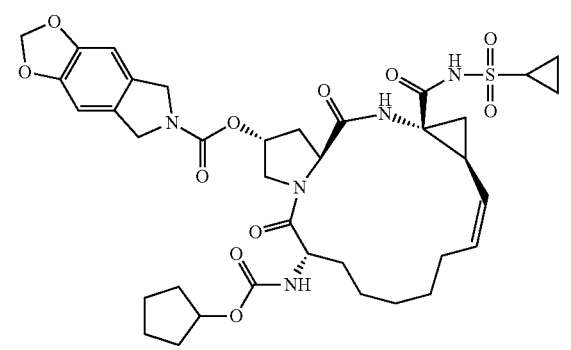

In the following Scheme 7, the product 12 (e.g., 12a-12f and 12-Ref) was used for deprotection first by removing Boc with HCl acid, followed by either alkylation or amidation with reagent SM-10 ($R^{16}$—Cl or $R^{16}$—Br) to obtain an N-alkylated product 15 or amidation with an alkylsulfonyl or arylsulfonyl chloride reagent SM-9 [$R^{17}S(O)_2Cl$] to form product 16, wherein $R^{16}$ and $R^{17}$ each is $C_1$-$C_6$ alkyl, $C_3$-$C_6$ cycloalkyl, $C_1$-$C_6$ alkoxycarbonyl, $C_3$-$C_6$ cycloalkoxycarbonyl, $C_6$-$C_{10}$ aryl, $C_6$-$C_{10}$ arylcarbonyl, $C_6$-$C_{10}$ aryloxycarbonyl or $C_2$-$C_{10}$ heterocyclic group, which generates more polyheterocyclic compounds 15a-15b and 16a-16c shown below.

Scheme 7:
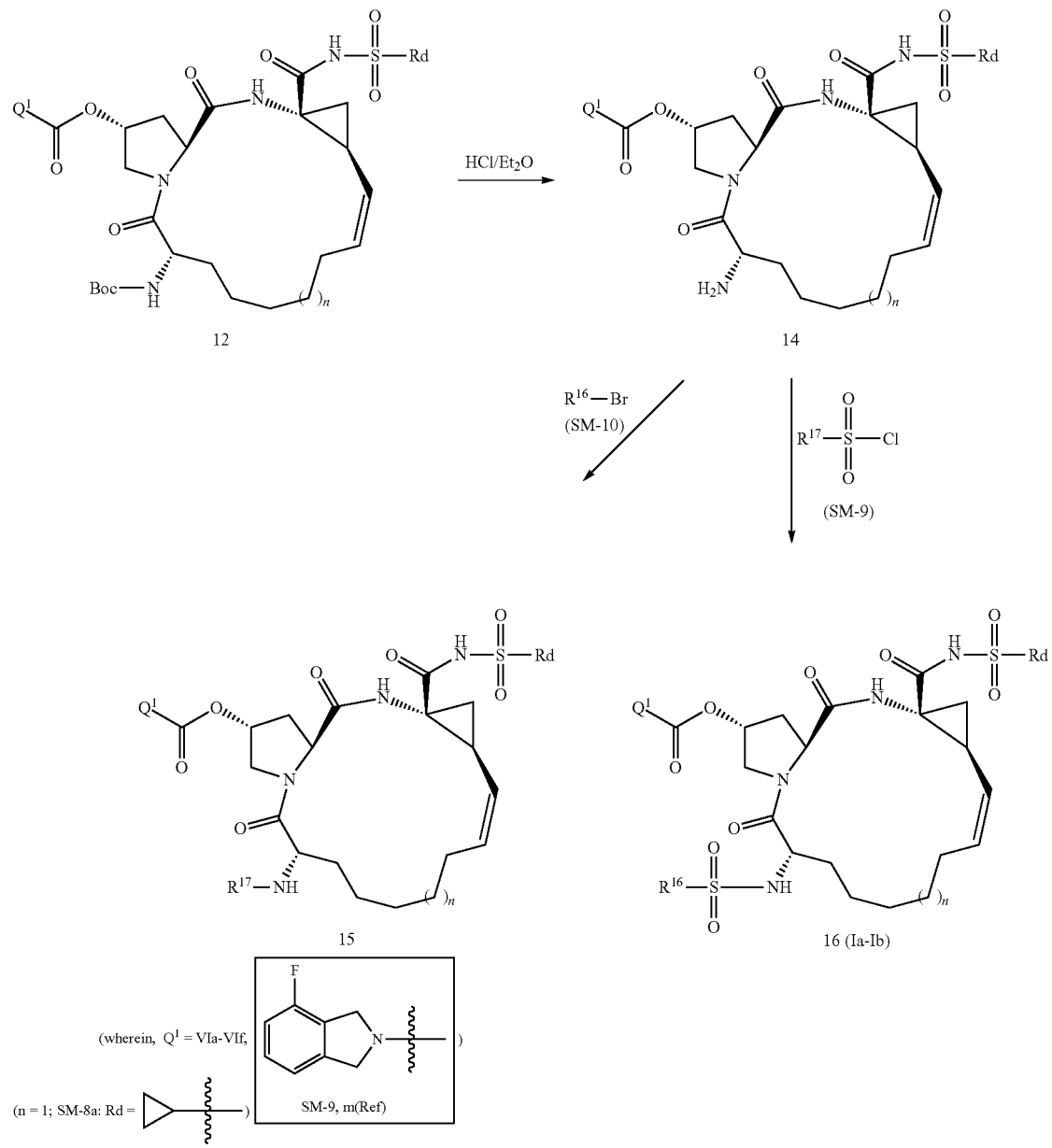
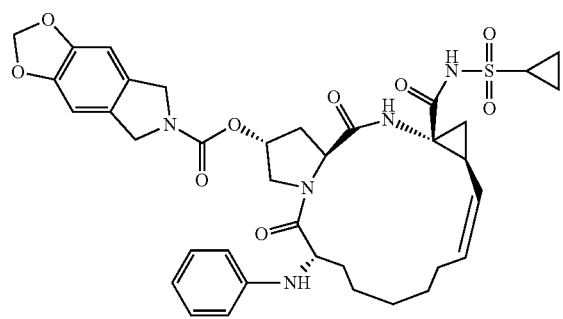
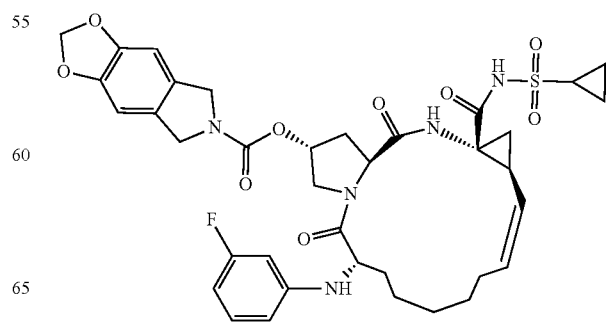

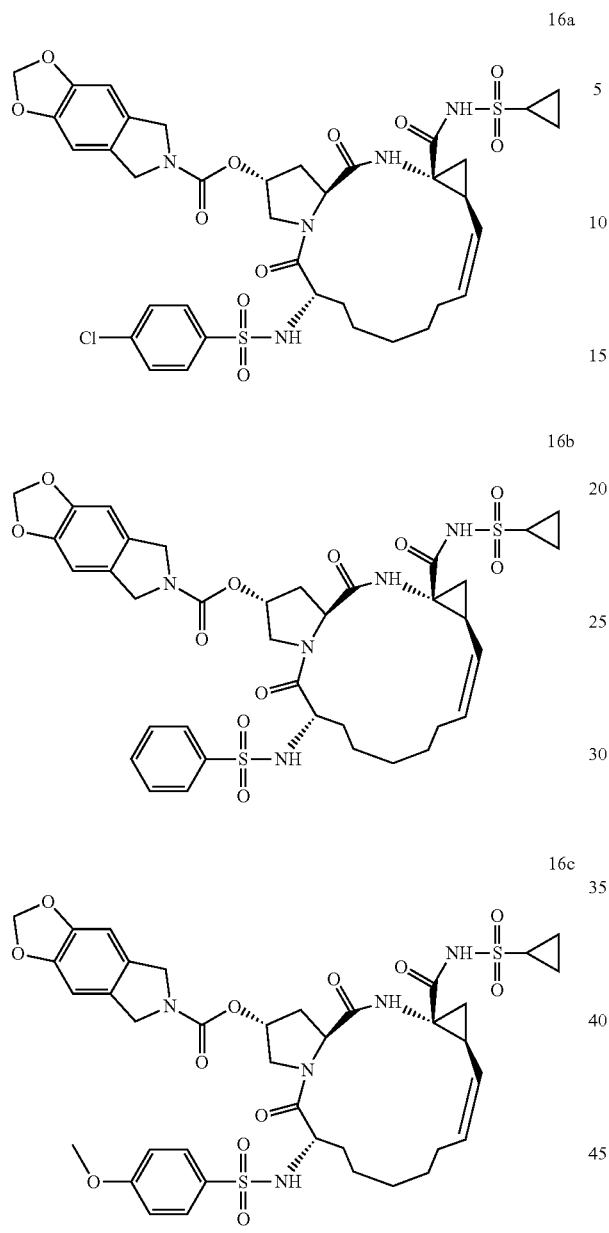

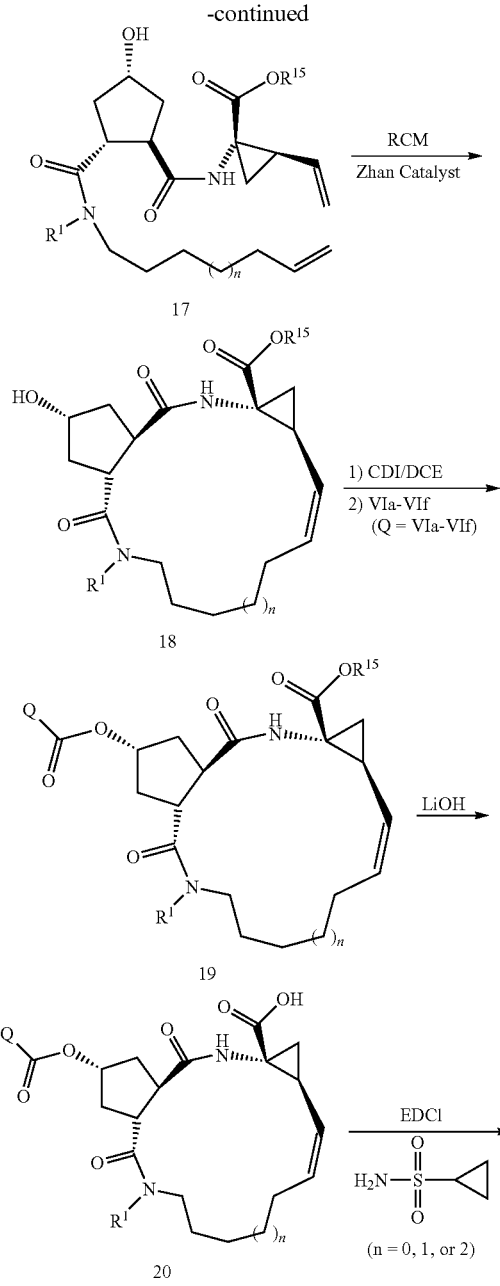

In order to optimize efficacy and biological property of new HCV inhibitors, there are two more different macrocyclic structure designed and synthesized in the following Schemes 8 and 9.

Scheme 8:

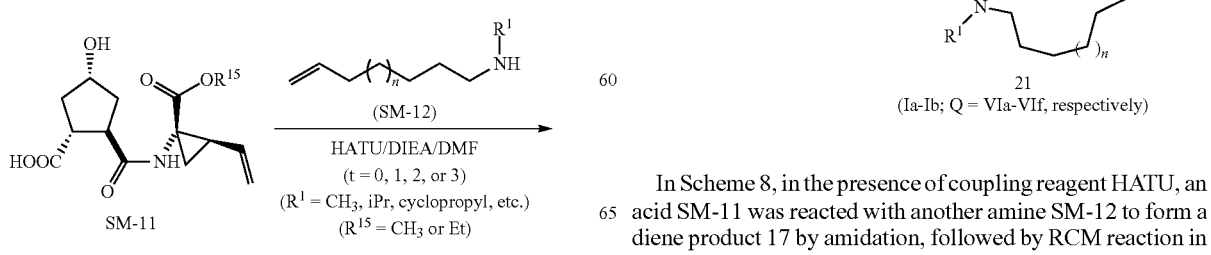

In Scheme 8, in the presence of coupling reagent HATU, an acid SM-11 was reacted with another amine SM-12 to form a diene product 17 by amidation, followed by RCM reaction in the presence of Zhan catalyst-1B to form a 14-16 membered macrocyclic product 18. In the presence of coupling reagent CDI, product 18 was reacted with compounds VIa-VIf, respectively to obtain polyheterocyclic compounds 21a-21f, then the methyl/ethyl ester was hydrolyzed with LiOH in water-MeOH solution to offer a new carboxylic acid 11. Finally, in the presence of a coupling reagent such as EDCI or HATU, the carboxylic acid 20 reacted with different kinds of alkylsulfonamide, cycloalkylsulfonamide or arylsulfonamide [RdS(O)$_2$NH$_2$], respectively, to form a series of novel polyheterocyclic based macrocyclic compounds Ia-Ib (21a-21j), shown below:

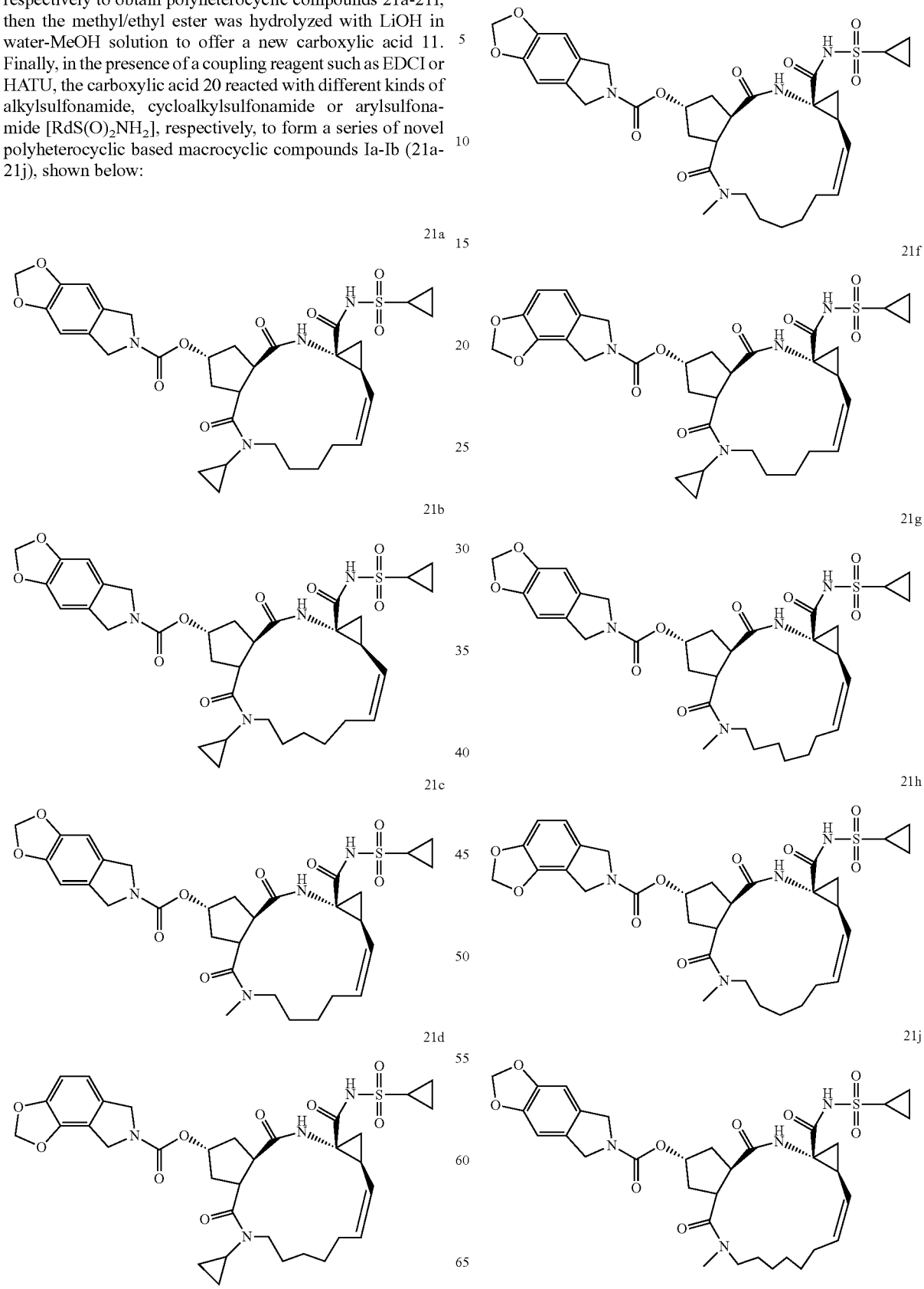

Scheme 9:

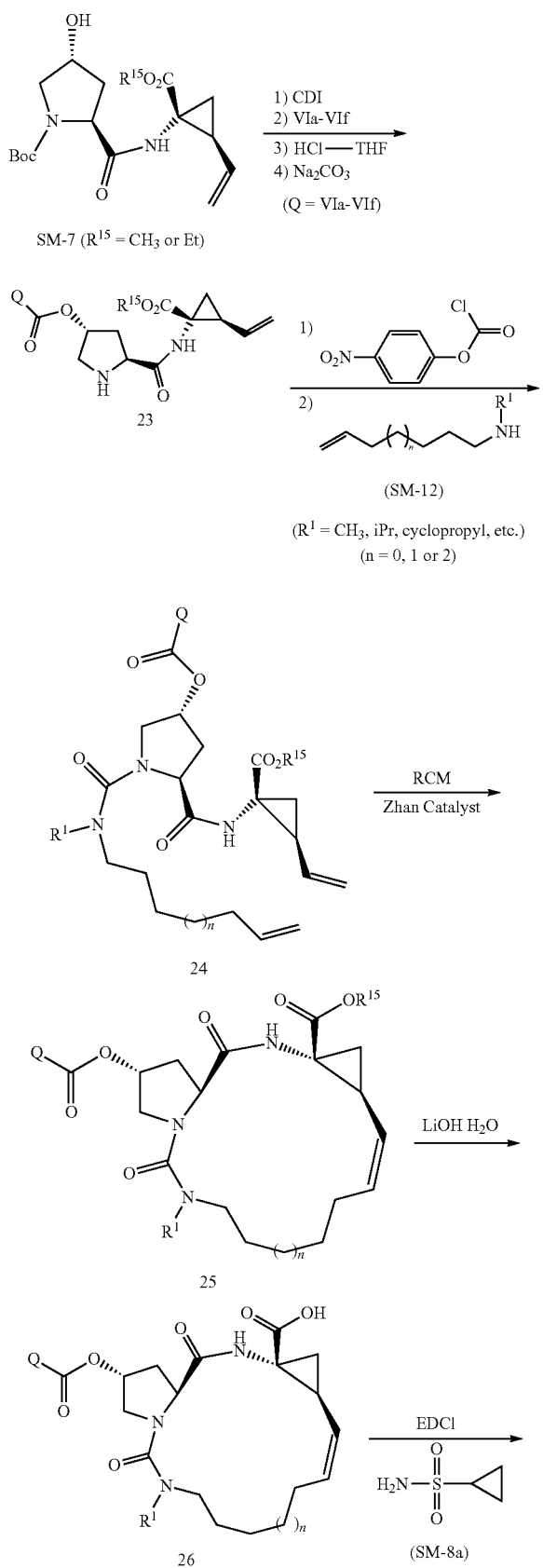

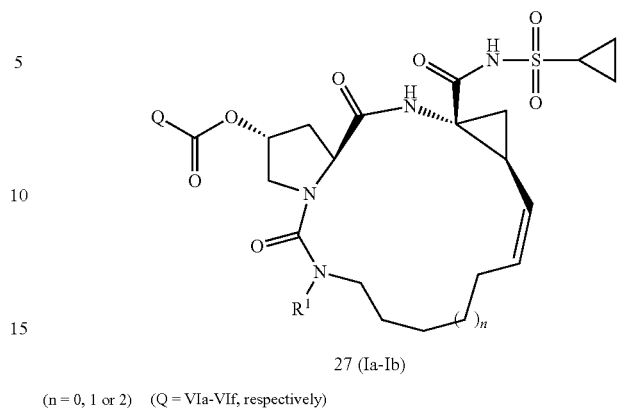

In Scheme 9, in the presence of coupling reagent CDI, SM-7 was reacted with compounds VIa-VIf, respectively to obtain polyheterocyclic compounds 23a-23f, followed by reacting with a reagent chloroformic acid 4-nitrophenyl ester and SM-12 to form a diene product 24. In the presence of Zhan catalyst-1B, the diene product 24 was conducted a RCM reaction to form a desired macrocyclic product 25, then the methyl/ethyl ester was hydrolyzed with LiOH in water-MeOH solution to offer a new carboxylic acid 26. Finally, in the presence of a coupling reagent such as EDCI or HATU, the carboxylic acid 26 reacted with different kinds of alkylsulfonamide, cycloalkylsulfonamide or arylsulfonamide [RdS(O)$_2$NH$_2$], respectively, to form a series of novel polyheterocyclic based macrocyclic compounds Ia-Ib (27a-27c and 27-Ref), shown below:

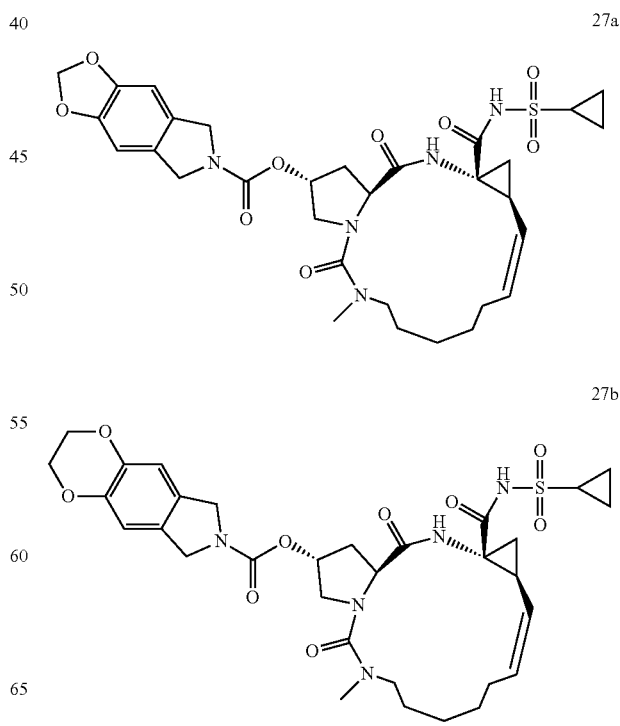

39

-continued

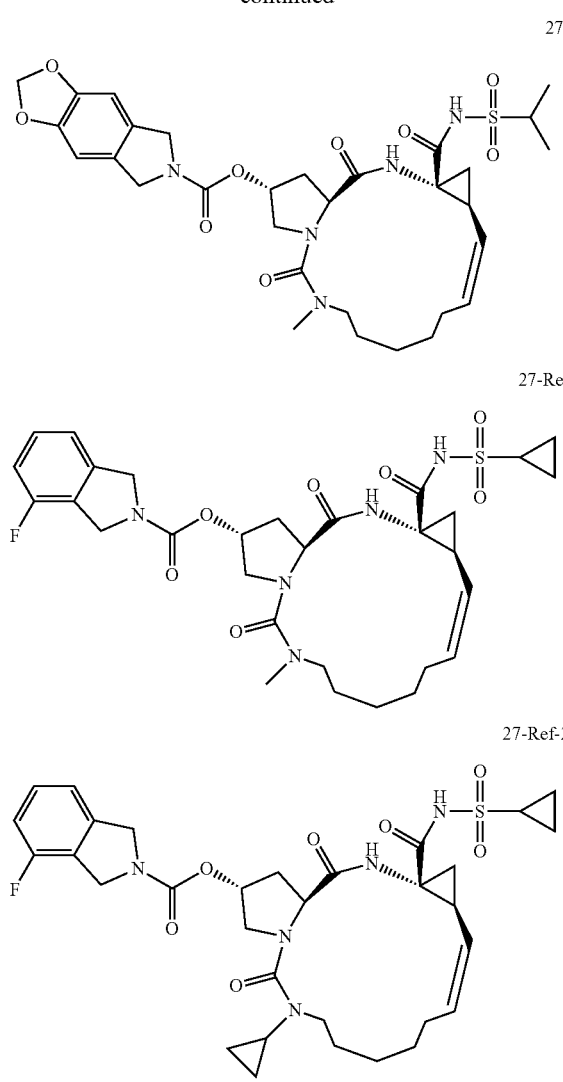

27c

27-Ref

27-Ref-2

To evaluate the difference in potency and other biological activities between the macrocyclic and linear structures for the novel polyheterocyclic based HCV inhibitors, there are different kinds of linear compounds IIa-IIb (30 and 33) with polyheterocyclic groups VIa-VIf prepared as shown in the following Schemes 10 and 11, respectively.

Scheme 10:

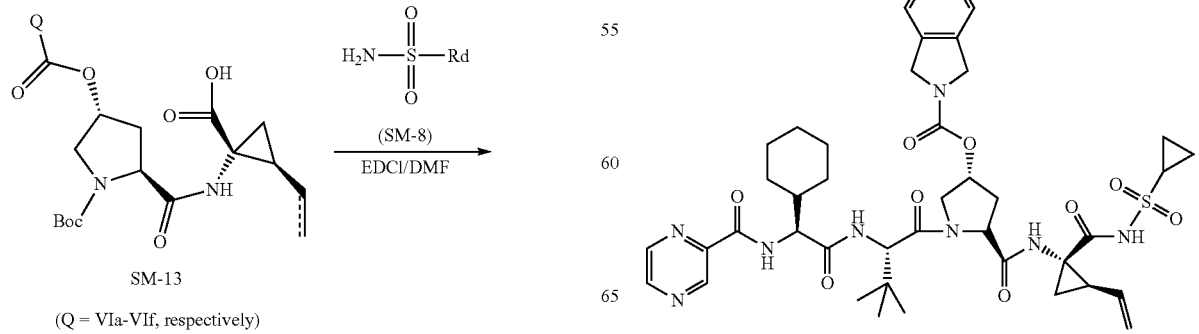

40

-continued

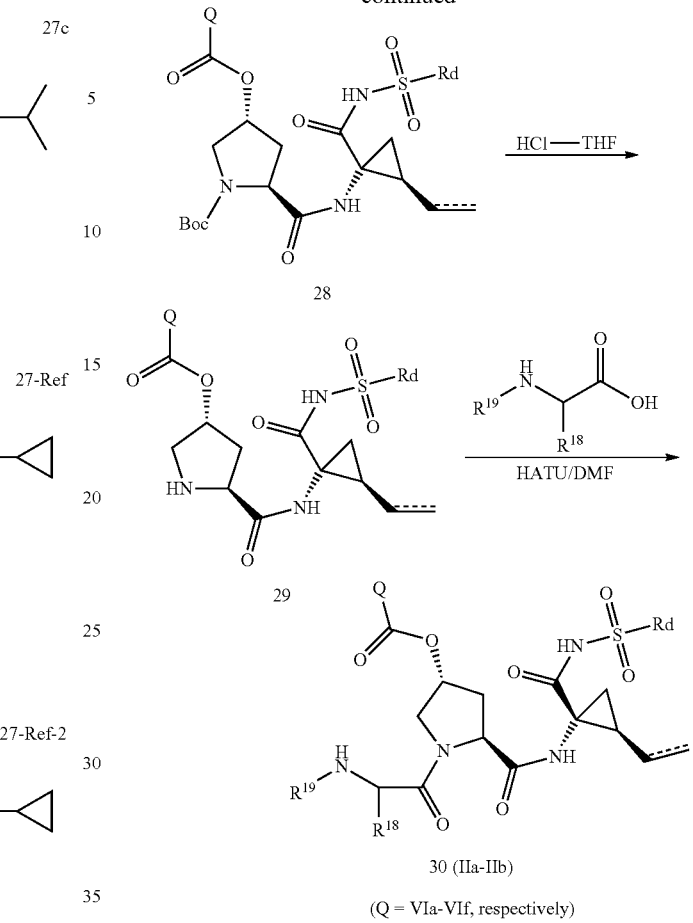

28

29

30 (IIa-IIb)

(Q = VIa-VIf, respectively)

In Scheme 10 above, in the presence of coupling reagent EDCI, an amine SM-13 was reacted with a sulfonamide RdS(O)$_2$NH$_2$], (SM-8) to form product 28, followed by removing Boc protecting group to obtain a de-Boc product 29. Finally, in the presence of a coupling reagent such as EDCI or HATU, the amine intermediate 29 was reacted with different kinds of amino acid derivatives SM-14 selected from a list of chemical reagents shown below to form various products IIa-IIb (30a-30ar) as shown as follows, wherein Rd and R$^{18}$ each is C$_1$-C$_6$ alkyl or C$_3$-C$_6$ cycloalkyl group, and R$^{19}$ is C$_1$-C$_{20}$ alkyl, C$_1$-C$_{20}$ alkylcarbonyl, C$_1$-C$_{20}$ alkoxycarbonyl, or C$_1$-C$_{20}$ alkylsulfonamido groups as shown below from compounds 30a-30ar.

30a

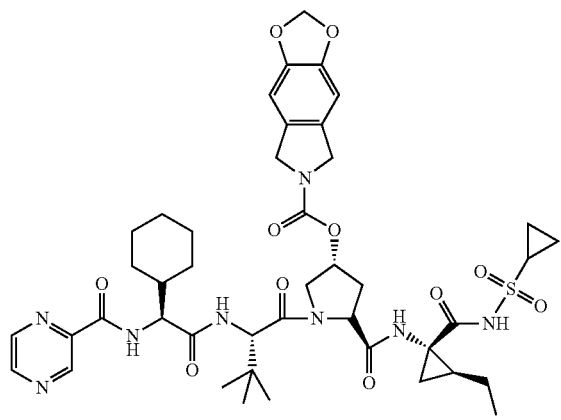
30b
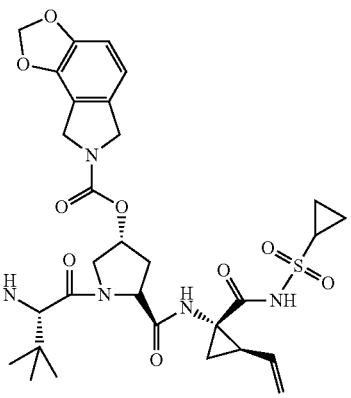
30e
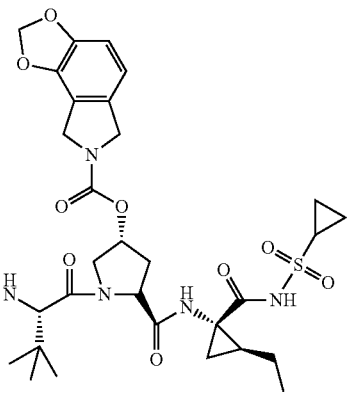
30f
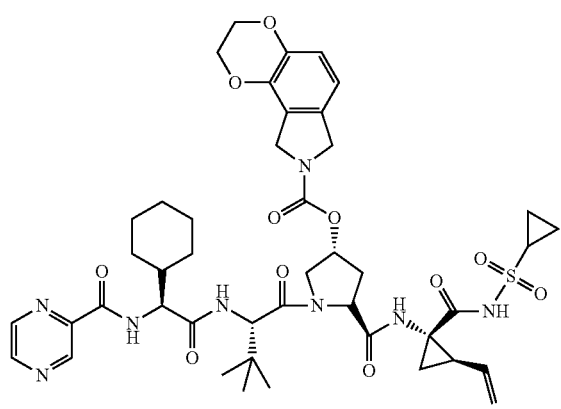
30c
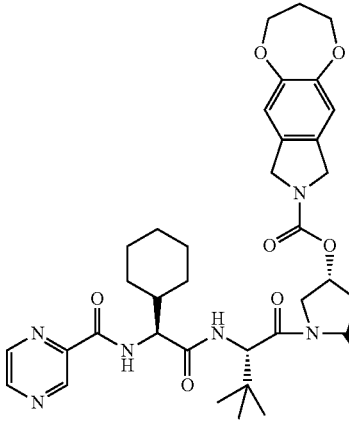
30g
30d

30h
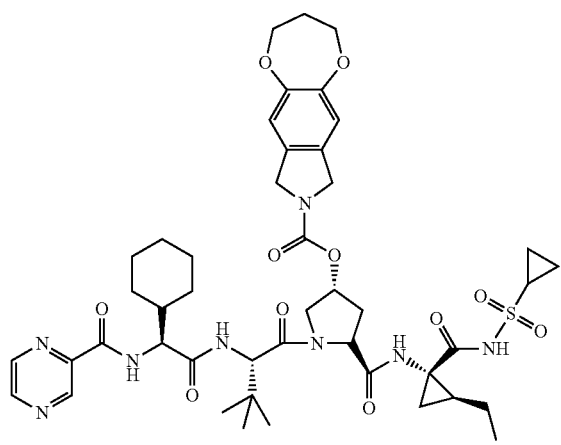
30m
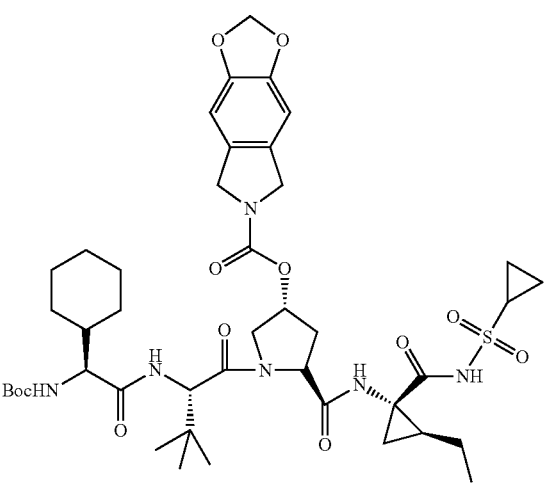
30j
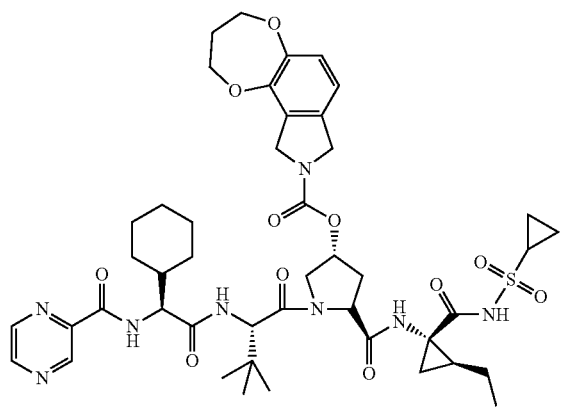
30n
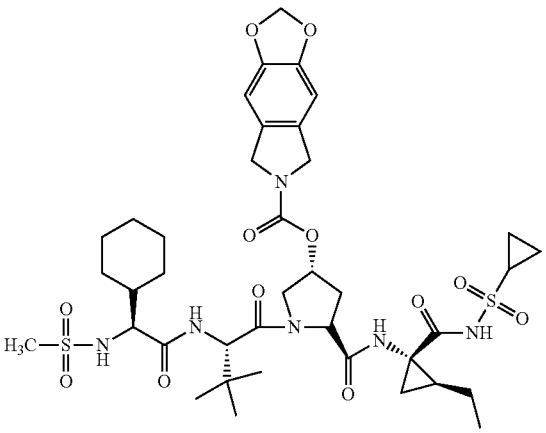
30k
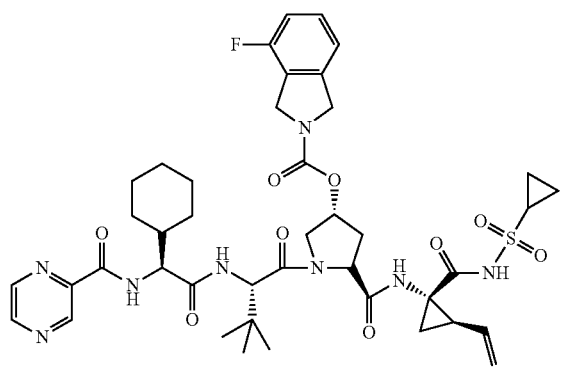
30p
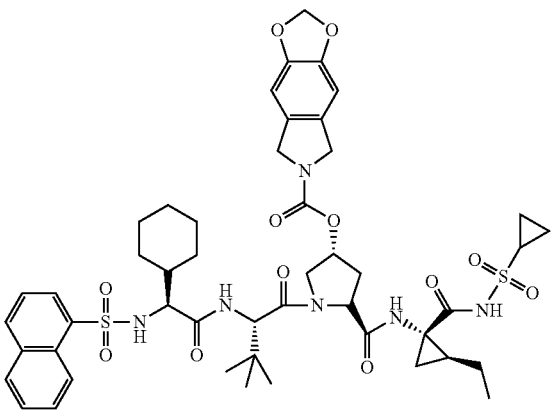

30q
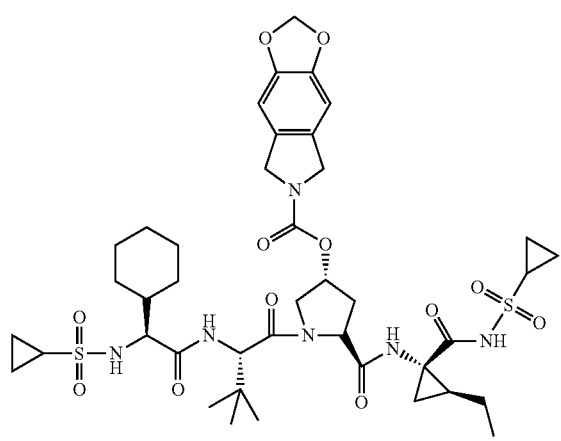
30t
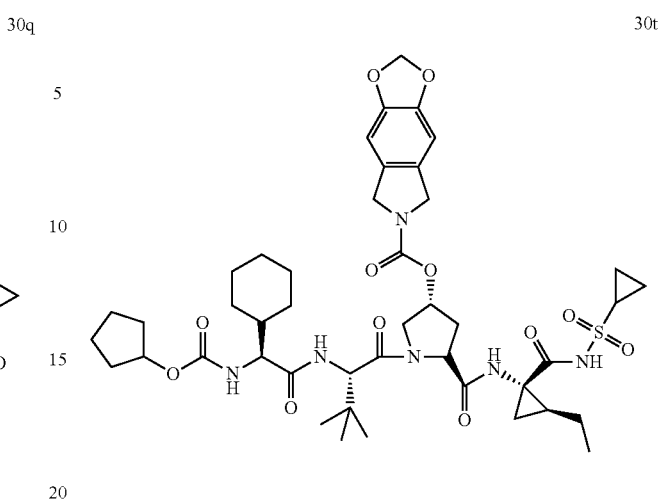
30r
30v
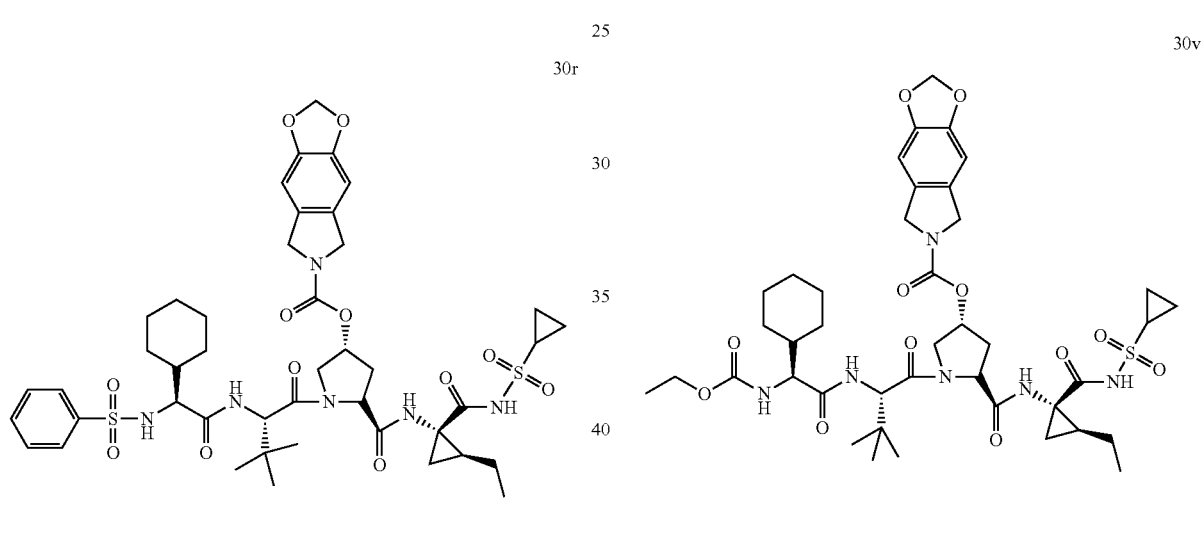
30s
30w
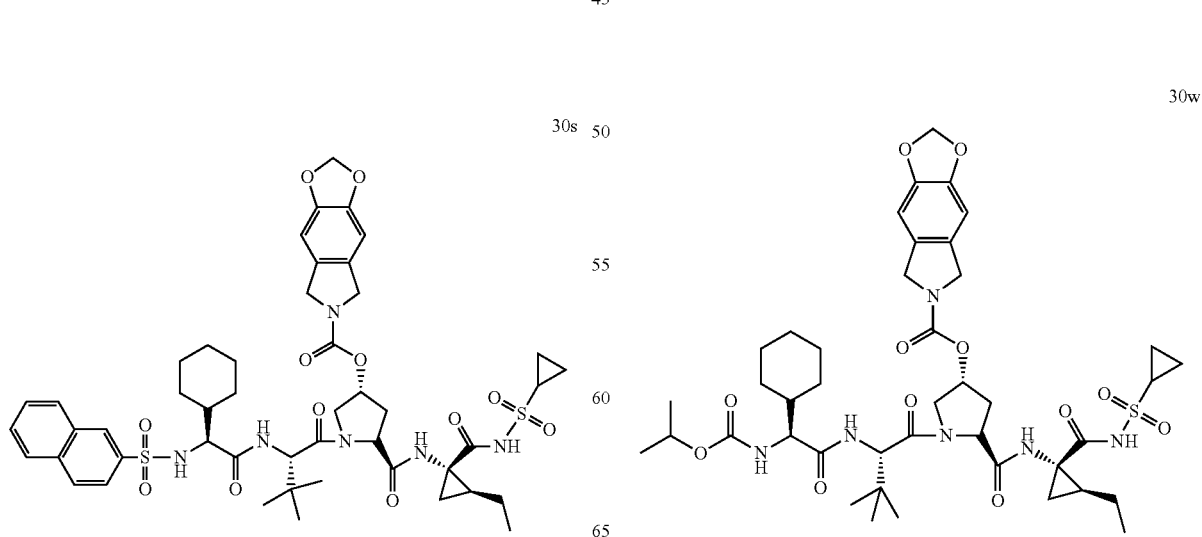

30x
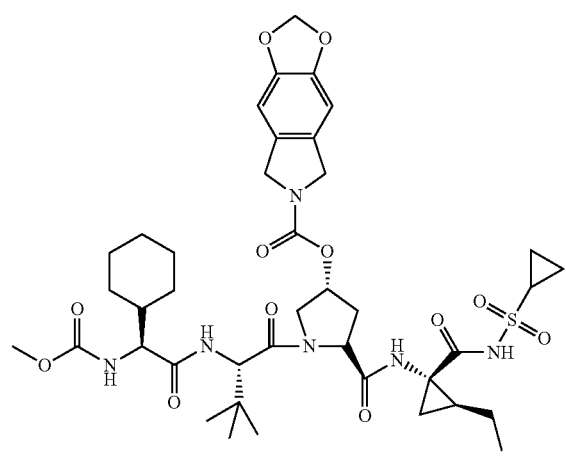
30aa
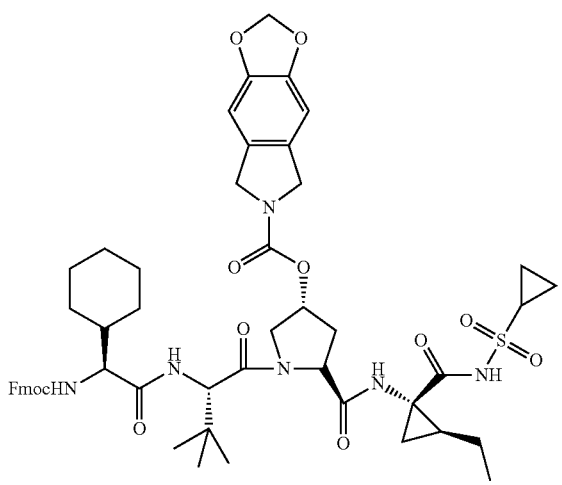
30y
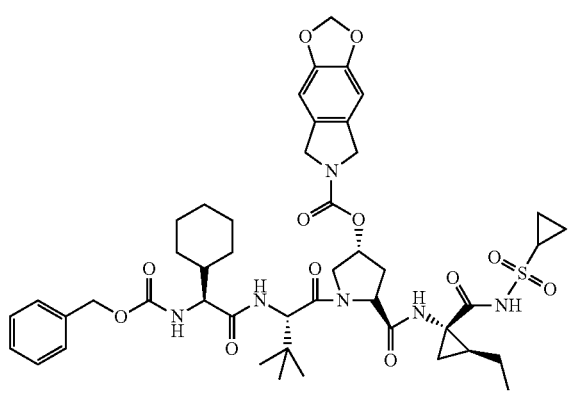
30ab
30z
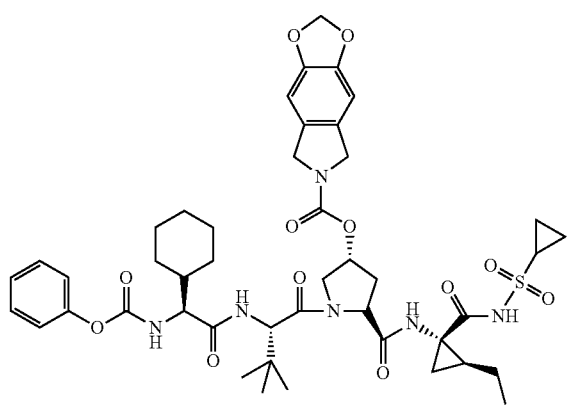
30ac
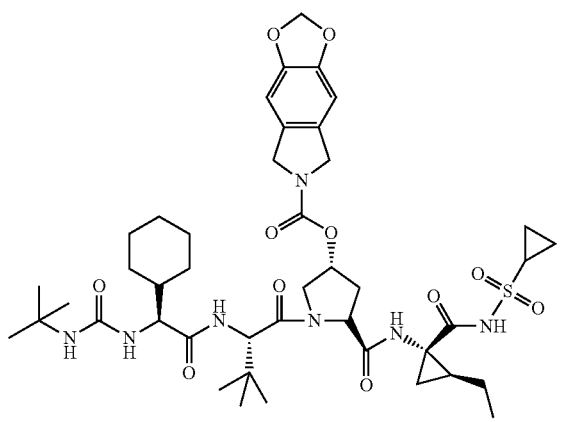

30ad
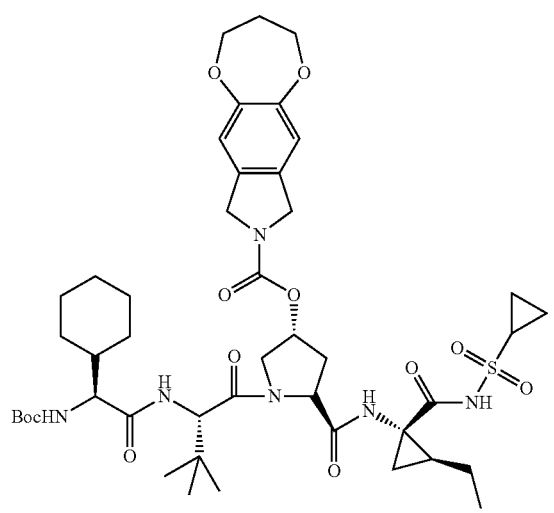
30ag
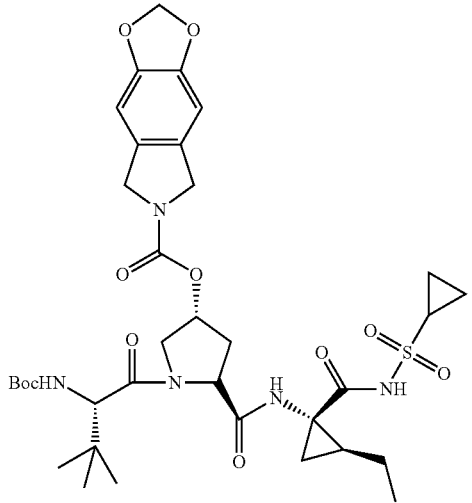
30ae
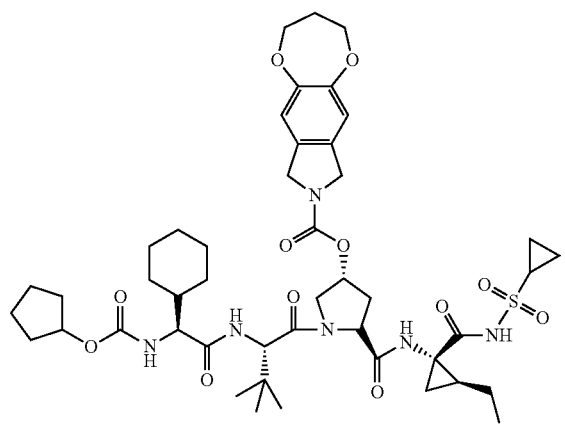
30ah
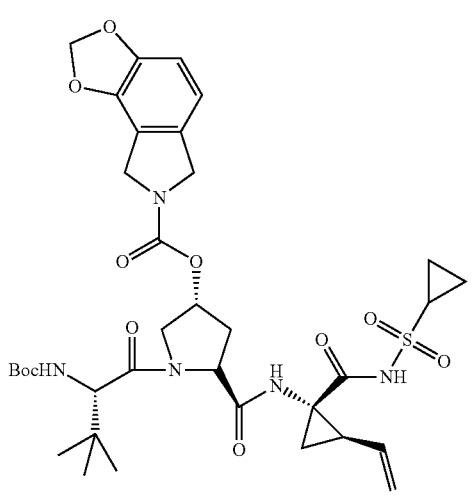
30af
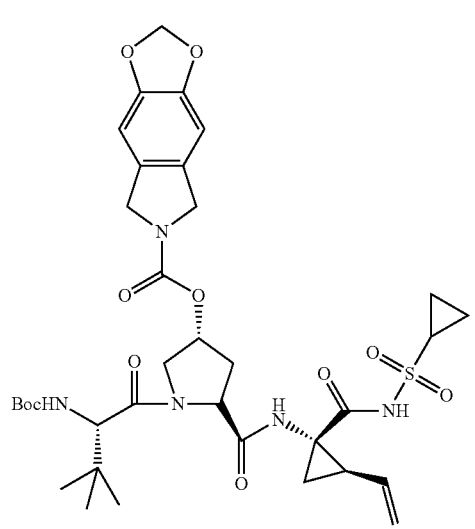
30aj
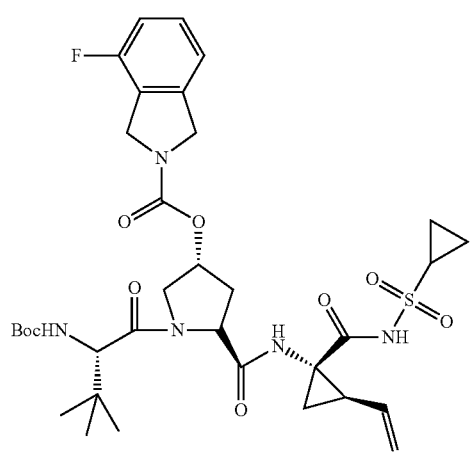

30ak
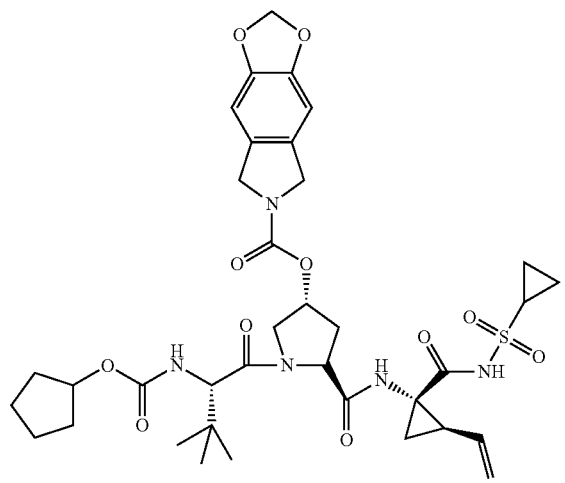
30ap
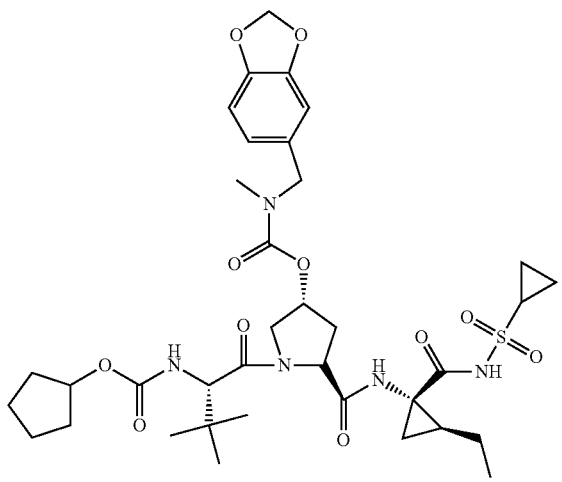
30am
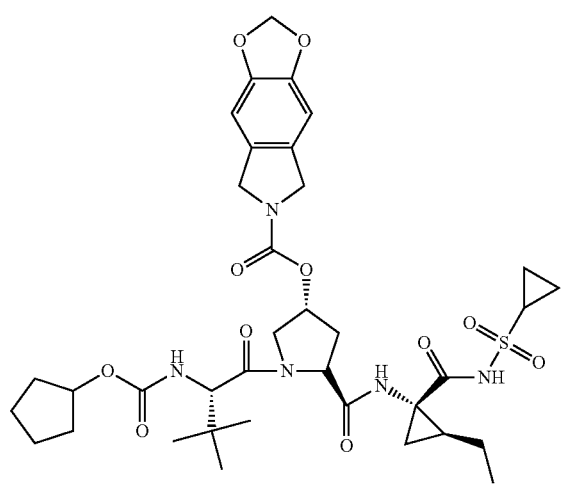
30aq
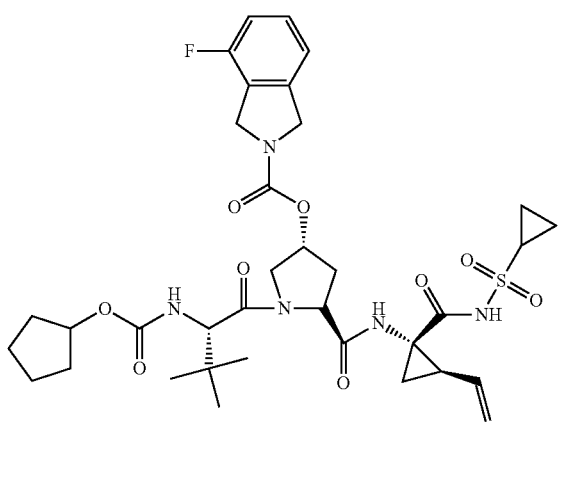
30an
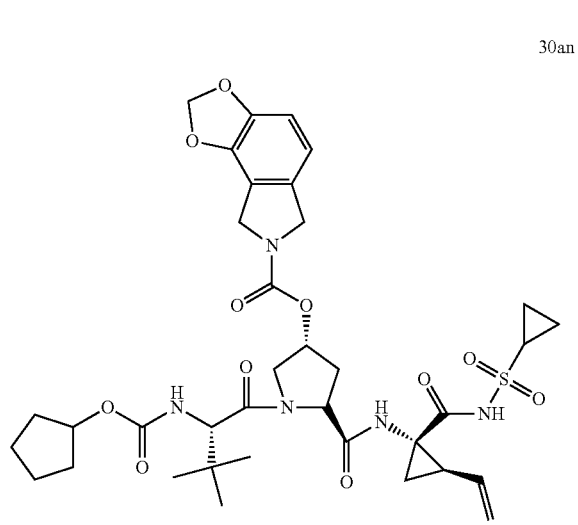
30ar
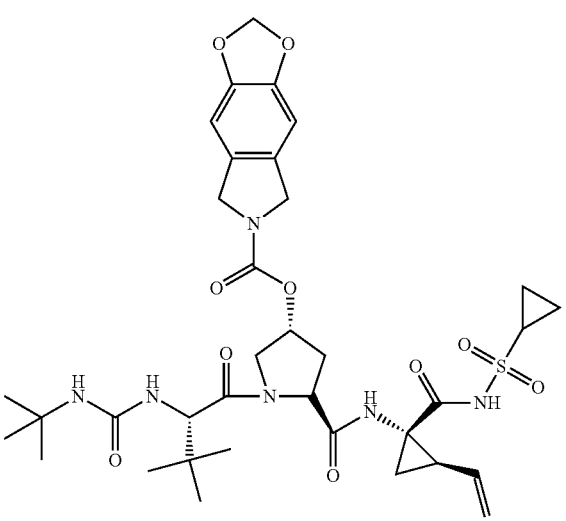

Scheme 11:

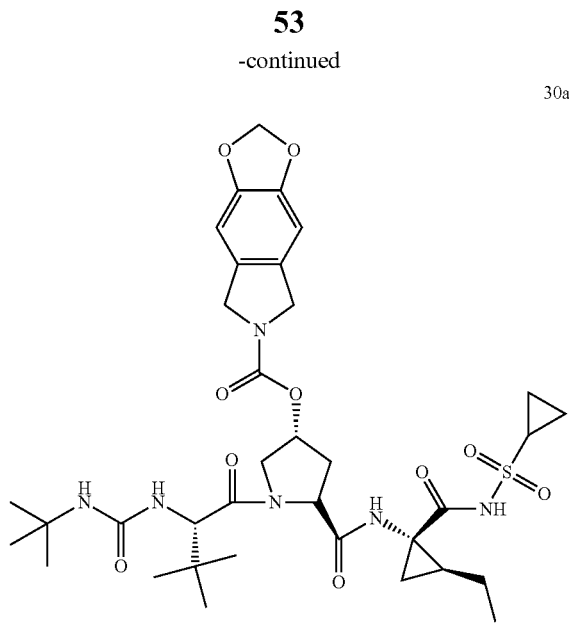
30as

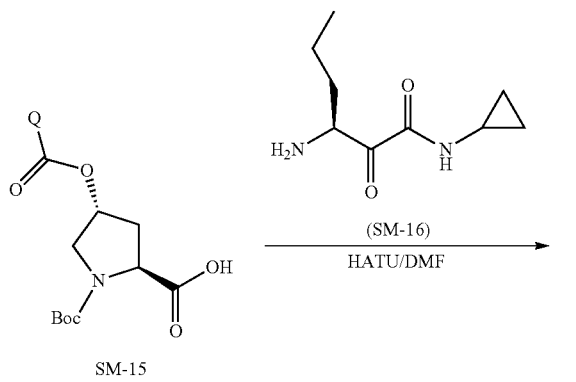
SM-15
(Q = VIa-VIf, respectively)

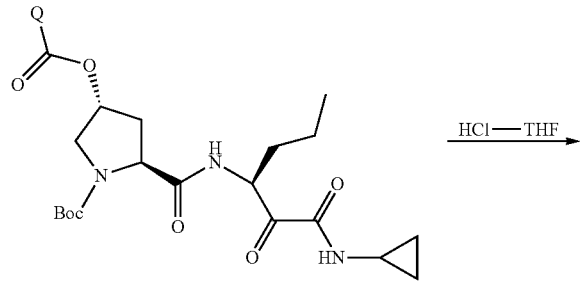
31

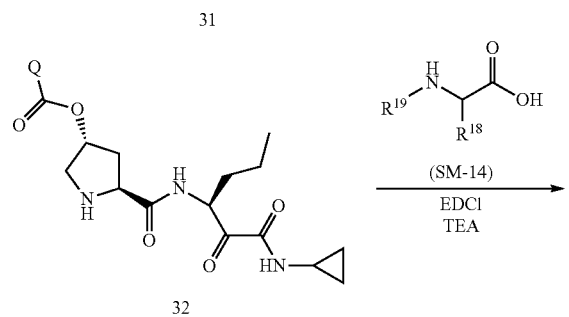
32

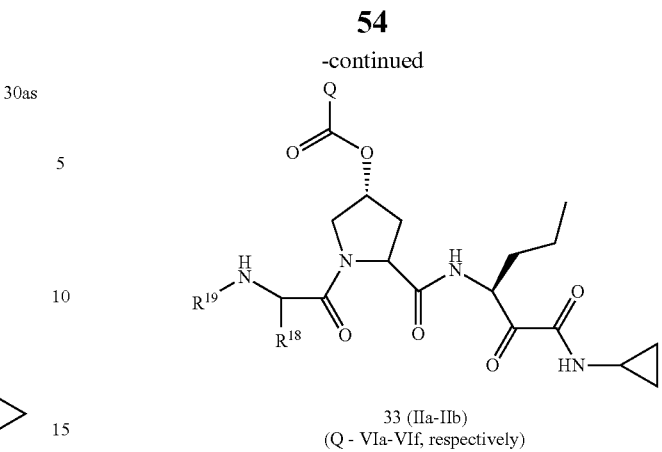
33 (IIa-IIb)
(Q - VIa-VIf, respectively)

In Scheme 11 above, in the presence of coupling reagent HATU in DMF, an acid SM-15 was reacted with another amine reagent SM-16 to form an amide product 31 by amidation, followed by removing Boc protecting group with HCl-THF solution to obtain an amine product 32. Finally, in the presence of a coupling reagent such as EDCI or HATU, the amine intermediate 32 reacted with various carboxylic acids SM-14, respectively to form different kinds of novel polyheterocyclic based linear compounds IIa-IIb (33a-33d) shown as follows, wherein $R^{18}$ each is $C_1$-$C_6$ alkyl or $C_3$-$C_6$ cycloalkyl group, and $R^{19}$ is $C_1$-$C_{20}$ alkyl, $C_1$-$C_{20}$ alkylcarbonyl, $C_1$-$C_{20}$ alkoxycarbonyl, or $C_1$-$C_{20}$ alkylsulfonamido groups.

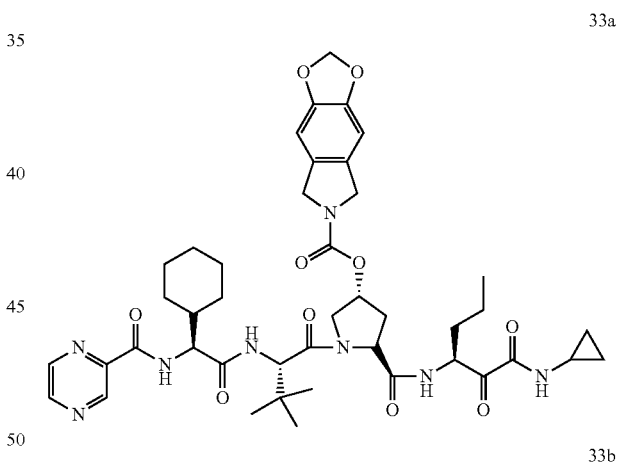
33a

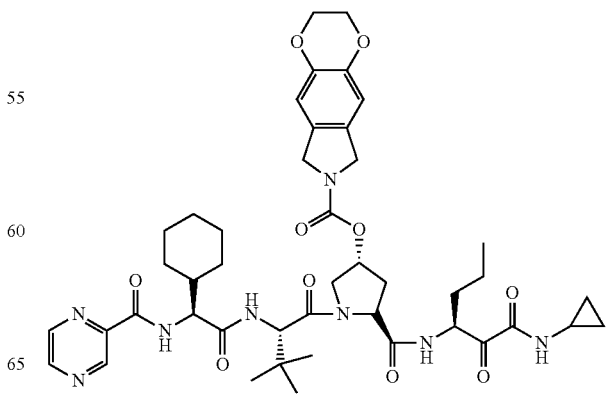
33b

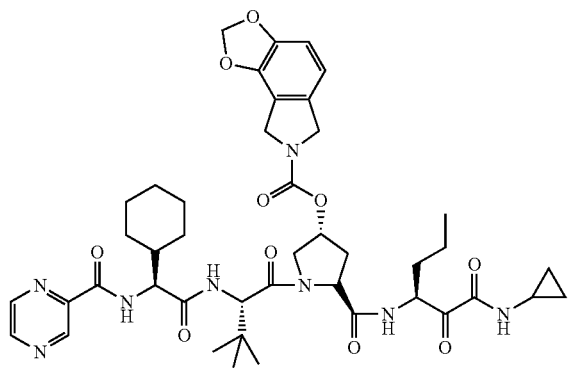

33c

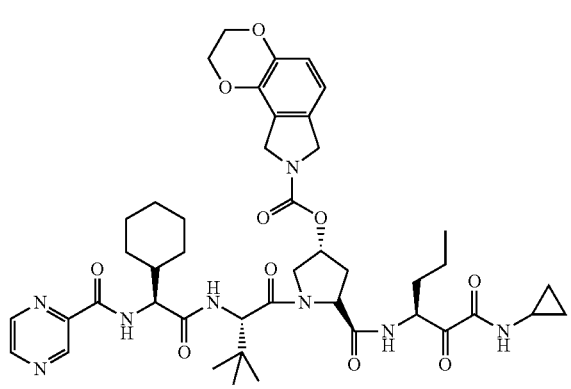

33d

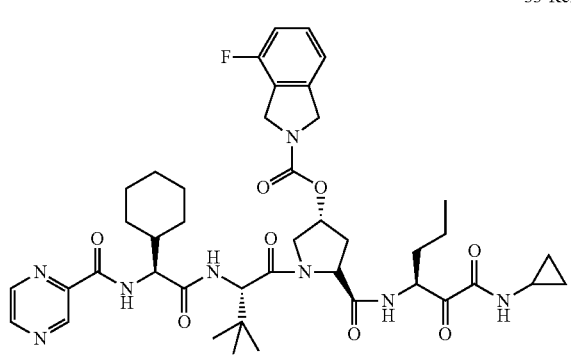

33-Ref

Additional polyheterocyclic based compounds within the scope of the present invention can be prepared using other suitable starting materials through the above synthetic routes or other developed procedures as reported from different references. The methods described in Schemes 1-11 above may also additionally include steps, either before or after the steps described specifically herein, to add or remove suitable protecting groups in order to ultimately allow synthesis of the compounds in this invention. In addition, various synthetic steps may be performed in an alternate sequence or order to give the desired compounds.

Synthetic chemistry transformations and protecting group methodologies (protection and deprotection) useful in synthesizing applicable compounds in this invention are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds mentioned herein may contain a non-aromatic double bond and one or more asymmetric centers. Thus, they can occur as racemates and racemic mixtures, single enantiomers, individual diastereomers, diastereomeric mixtures, tautomers, and cis- or trans-isomeric forms, and/or hydrates. All such isomeric forms are contemplated.

So far, there is no any effective animal model for scientists to evaluate the efficacy of new compounds for inhibiting the HCV NS3 protease. The compounds described above in the present invention can be preliminarily screened by evaluating the $IC_{50}$ and/or $EC_{50}$ results for their activity and efficacy in treating HCV infection by an in vitro and/or in vivo assay as follows, then have some highly potent HCV inhibitors selected for other PK and toxicity studies before clinic trial during new drug development. Other methods will also be apparent for scientists in pharmaceuticals.

HCV NS3-4a Protease Assay In Vitro.

The assay was conducted in Buffer A containing 30 mM NaCl, 5 mM $CaCl_2$, 10 mM DTT, 50 mM Tris (pH7.8), using the Ac-Asp-Glu-Asp(EDANS)-Glu-Glu-Abu-ψ-[COO]-Ala-Ser-Lys (DABCYL)-$NH_2$ (FRETS) fluorescent peptide (AnaSpec, USA) as substrate. Briefly, 140 μL buffer A, 20 μL compounds dissolved in buffer A with different concentration and 20 μL HCV NS3-4A protease diluted in buffer A were added into 96-well plate respectively and mixed well. The reaction was initiate with adding 20 μL of FRET-S. Reactions were continuously monitored at 37° C. using a BMG Polarstar Galaxy (MTX Lab Systems, Inc. USA), with excitation and emission filters of 355 nm and 520 nm, respectively. The 50% inhibitory concentration ($IC_{50}$) was calculated with Reed & Muench methods.

Antiviral Assay:

Antiviral assays were carried out in black-walled, clear bottomed 96-well plates. Renila luciferase reporter replicon cells were seeded at a density of $7 \times 10^3$ cells/well in 100 μl complete DMEM culture without selection antibiotics. Eight twofold serial dilutions of compounds were prepared in complete DMEM and added to the appropriate wells, yielding final concentrations in 200 μl of complete DMEM culture. Following 3 days of incubation, cells were incubated with 100 μl fresh culture containing EnduRen™ Live Cell Substrate (Promega) at final concentrations of 60 μM at 37° C. in 5% $CO_2$ for 2 h in the dark. Luminescence was then measured using an EnVision (Perkin-Elmer) microplate reader. Data were normalized to percentage of the control, and the the 50% effective concentration ($EC_{50}$) values were calculated using the method of Reed-Muench.

Acute Toxicity Study (MTD):

Materials and Methods for MTD Study are as follows:

Animals:

320 KM mice, Certificate Number: 2007000510144, male and female were each half, 40 Wistar rats, certificate number: 2007000510555, male and female were each half Animals were purchased from SLAC Laboratory Animal Limited Co., Feed: Breeding fodder of Radiation, special for rats and mice, was purchased from SLAC Laboratory Animal Limited Co.

Test Group:

Animals were fed freely for adaptation more than 1 week. Healthy rats, body weight between 170-190 g, were divided randomly into 3 groups, 5 male and 5 female in each group. Healthy mice, body weight between 18-20 g, were divided randomly into 22 groups, 5 male and 5 female in each group.

Administration Method:

In rats, the compound weighing 21.00 g, serial number 1-3 respectively, adding 0.7% sodium carboxymethyl cellulose solution 30.00 g, high-speed homogenizer machine 15000 RPM, 10 min mixing, the rats were fed once, oral dose 10000 mg/kg. In mice, the compound weighing 2.00 g, serial number 4-25 respectively, adding 0.7% sodium carboxymethyl cellulose solution 8.00 g, high-speed homogenizer machine 10000 RPM, 10 min mixing, the mice were fed once, oral dose 10000 mg/kg.

Clinical Observation:

Animals were observed every hour after administration in the first day, and behavior observation daily continuous for a week. Dead animals were necropsied, gross pathology of the organs were observed and recorded.

Evaluation of Toxicity:

Toxicity was evaluated by animal mortality, signs of clinical behavior and others.

Among all of synthesized polyheterocyclic compounds 11a-11p, 12a-12u, 15a-15b, and 16a-16c, 30a-30ar, 33a-33d and some reference compounds 12-Ref, 21-Ref, 27-Ref, the results of HCV protease (HCV NS3-4A) inhibition test are listed in Table 1;

where the scope of potent activity ($IC_{50}$): ≥200 nM labeled "A", active in the range of 30-200 nM labeled "B", active range≤30nM labeled "C".

TABLE 1

Activity of Novel Polyheterocyclic Based Compounds for Inhibiting HCV NS3 Protease

| Entry | Compound | NS3-NS4A $IC_{50}$ |
|---|---|---|
| 1 | 11a | A |
| 2 | 11b | A |
| 3 | 11c | A |
| 4 | 11d | A |
| 5 | 12a | C |
| 6 | 12b | C |
| 7 | 12c | C |
| 8 | 12d | C |
| 9 | 12e | C |
| 10 | 12f | C |
| 11 | 12g | C |
| 12 | 12h | C |
| 13 | 12j | B |
| 14 | 12k | C |
| 15 | 12m | B |
| 16 | 12n | C |
| 17 | 12p | C |
| 18 | 12q | C |
| 19 | 12r | C |
| 20 | 12s | C |
| 21 | 12t | C |
| 22 | 12u | C |
| 23 | 12-Ref | C |
| 24 | 15a | C |
| 25 | 15b | C |
| 26 | 16a | C |
| 27 | 16b | C |
| 28 | 16c | C |
| 29 | 21a | B |
| 30 | 21b | B |
| 31 | 21c | C |
| 32 | 21d | B |
| 33 | 21e | C |
| 34 | 21f | B |
| 35 | 27a | B |
| 36 | 27b | B |
| 37 | 27c | B |
| 38 | 27-Ref | B |
| 39 | 27-Ref-2 | B |
| 40 | 30a | C |
| 41 | 30b | C |
| 42 | 30c | C |
| 43 | 30d | C |
| 44 | 30e | C |
| 45 | 30f | C |
| 46 | 30g | C |
| 47 | 30h | C |
| 48 | 30j | C |
| 49 | 30k | C |
| 50 | 30m | C |
| 51 | 30n | C |
| 52 | 30p | C |
| 53 | 30r | C |
| 54 | 30s | C |
| 55 | 30t | C |
| 51 | 30v | C |
| 52 | 30w | C |
| 53 | 30x | C |
| 54 | 30y | C |
| 55 | 30z | C |
| 56 | 30aa | C |
| 57 | 30ab | C |
| 58 | 30ac | C |
| 59 | 30ad | B |
| 60 | 30ae | B |
| 61 | 30af | C |
| 62 | 30ag | C |
| 63 | 30ah | C |
| 64 | 30aj | C |
| 65 | 30ak | C |
| 66 | 30am | C |
| 67 | 30an | C |
| 68 | 30ap | C |
| 69 | 30aq | C |
| 70 | 30ar | C |
| 71 | 30-Ref | C |
| 72 | 33a | B |
| 73 | 33b | B |
| 74 | 33c | B |
| 75 | 33d | A |
| 76 | 30-Ref | B |

The potent screening results in Table 1 show that: (1) the polyheterocyclic based macrocyclic compounds (e.g., 12a-12u) containing cyclopropyl sulfonamide and isopropylsulfonamide have much better HCV inhibition activity than the polyheterocyclic based carboxyl acid products (e.g., 11a-11m) that do not have cyclopropylsulfonamide or isopropylsulfonamide group incorporated by amidation, (2) in general, the polyheterocyclic based macrocyclic compounds Ia-Ib (e.g., 12a-12u) have better efficacy and biological activity than the polyheterocyclic based linear compounds IIa-IIb (e.g., 30a-30ar and 33a-33d), and (3) several of the novel polyheterocyclic based macrocyclic sulfonamide compounds Ia-Ib (e.g., 12a-12d, 12q-12u) are highly effective ($EC_{50}$: 0.001-1.0 uM) as HCV inhibitors, and many of new polyheterocyclo based HCV inhibitors have excellent biological activities to inhibit HCV in comparison with some referred HCV inhibitors already in clinical Phase II and III, such as InterMune (ITMN-191, 12Ref)-Roche, and Merck MK-7009.

Overall, all prepared new polyheterocyclic based compounds have been evaluated for their potency and efficacy in vitro and/or in vivo, and there are two novel classes of polyheterocyclic based compounds found highly effective to inhibit HCV. Moreover, the present invention explores the insight relationship between the structures of new polyheterocyclic compounds and efficacy of HCV inhibition, which provides valuable clue to develop an effective potential HCV inhibitors among the developed novel polyheterocyclic compounds Ia-Ib and IIa-IIb.

Abbreviations of chemical materials, reagnets, and solvents related to the present invention are listed as follows:
SM4: N-Boc-trans-4-hydroxy-L-proline methyl ester
SM5: Boc-L-2-amino-8-azelaic acid
SM6: (1R,2S)-1-amino-2-cyclopropyl methyl vinyl
AIBN: azobisisobutyronitrile
(Boc) 2O: di-tert-butyl carbonate
CDI: N,N'-carbonyldiimidazole imidazole
DBU: 1,8-Diazabicyclo[5.4.0]undec-7-ene
EDCI: N-ethyl-N-(3-dimethyl aminopropyl)carbodiimide hydrochloride
HATU: 2-(7-benzotriazole azo)-N,N,N',N'-tetramethyl urea phosphate hexafluoride
NBS: N-bromosuccinimide
DMAP: 4-dimethylaminopyridine
DIEA: N,N-diisopropyl ethylamine
SOCl2: thionyl chloride
Pd/C: Palladium carbon
HMTA: hexamethylene tetramine
HOAc: acetic acid
HBr: Hydrobromic acid
HCl: hydrochloric acid
TFA: trifluoroacetic acid
TsOH: p-toluenesulfonate
NaOH: sodium hydroxide
ACN: acetonitrile
DCM: dichloromethane
DCE: dichloroethane
DMF: N,N-dimethylformamide
DMSO: dimethyl sulfoxide
Et2O: diethyl ether
EA: ethyl acetate
PE: petroleum ether
THF: tetrahydrofuran
TBME: tert-butyl methyl ether

EXAMPLES

General:
Infrared (IR) spectra were recorded on a Fourier Transform AVATAR™ 360 E.S.P™ spectrophotometer (Unit: $cm^{-1}$). Bands are characterized as broad (br), strong (s), medium (m), and weak (w). $^1$H NMR spectra were recorded on a Varian-400 (400 MHz) spectrometer. Chemical shifts are reported in ppm from tetramethylsilane with the solvent resonance as the internal standard ($CDCl_3$: 7.26 ppm). Data are reported as follows: chemical shift, multiplicity (s=singlet, d=doublet, t=triplet, q=quartet, br=broad, m=multiplet), coupling constants (Hz), integration, and assignment. $^{19}$F and $^{31}$P NMR spectra were recorded on a Varian-400 (400 MHz) and Varian-500 (500 MHz) spectrometers. The chemical shifts of the fluoro resonances were determined relative to trifluoroacetic acid as the external standard ($CF_3CO_2H$: 0.00 ppm), and the chemical shifts of the phosphorus resonances were determined relative to phosphoric acid as the external standard ($H_3PO_4$: 0.00 ppm). Mass spectra were obtained at Thermo Finnigan LCQ Advantage. Unless otherwise noted, all reactions were conducted in oven-(135° C.) and flame-dried glassware with vacuum-line techniques under an inert atmosphere of dry Ar. THF and $Et_2O$ were distilled from sodium metal dried flask, DCM, pentane, and hexanes were distilled from calcium hydride. Most chemicals were obtained from commercial sources or ordered by contract synthesis from Zannan SciTech Co., Ltd. in China. General procedures for preparation of different polyheterocyclic intermediates and products (Ia-Ib and IIa-IIb) are described in the following examples, respectively.

Example 1

Synthesis of Compound VIa

SM-1 (12.2 g, 0.5 mol) and 100 mL DCM were added into a 250 mL reaction flask, then NaOH (5 g) and DMSO (50 mL) were added and heated to 100° C. After the reaction was completed, the mixture was poured into ice water and extracted three times with DCM. The combined organic layer was washed with brine, then dried and concentrated, finally purified by column chromatography with silica gel to obtain the cyclized product 1-1 (7.7 g), yield 61%. ESI-MS (M+H$^+$): m/z calculated: 253.1, founded: 253.2.

The product 1-1 (5.0 g, 0.2 mol) was dissolved in ethanol, catalyst Pd/C (0.5 g) was added under hydrogen pressure (0.6 MPa). When the reaction was completed, the mixture was filtered and washed with ethanol, then the filtrate was concentrated to offer crude product (3.0 g). After purified by flash column, the desired product VIa (2.5 g) was obtained with purity over 99%, yield 76%. Total yield for two steps: 46%.

$^1$H-NMR for the product VIa (CDCl3, 500 MHz): δ 6.71 (s, 2H), 5.91 (s, 2H), 4.20 (s, 2H), 4.15 (s, 2H), 2.22 (s, 1H, NH). ESI-MS (M+H$^+$): m/z calculated 164.1, founded 164.2.

Example 2

Synthesis of Compound VIb

SM-1 (12 g, 0.5 mol) and 30 mL DCE were added to a 250 mL reaction flask, then NaOH (5 g) and DMSO (50 mL) were added and heated to 100° C. After the reaction was completed, the mixture was poured into ice water and extracted three times with DCM. The combined organic layer was washed with brine, then dried and concentrated. After purified by flash column, the desired product 1-2 (9.4 g) was obtained, yield 71%. ESI-MS (M+H$^+$): m/z calculated 268.1, founded 268.2.

The product of 2-1 (5.0 g) was dissolved in ethanol, Pd/C (0.5 g) was added with hydrogen pressure (0.6 MPa). When the reaction was completed, the mixture was filtered and washed with ethanol, the filtrate was concentrated to give crude product (3.0 g). After purified by flash column, the desired product VIb (2.9 g) was obtained. Total yield for two steps: 61%.

$^1$H-NMR for the product VIb (CDCl3, 500 MHz): δ 6.77-6.75 (d, J=8.0 Hz, 1H), 6.72-6.70 (d, J=8.0 Hz, 1H), 4.29-4.28 (m, 2H), 4.27-4.26 (m, 2H), 4.19 (s, 2H), 4.17 (s, 2H), 2.27 (s, 1H, NH). ESI-MS (M+H$^+$): m/z calculated 178.1, founded 178.2.

Example 3

Synthesis of Compound VIc

SM-1 (12 g, 0.5 mol) and Br(CH2)3Br (20 mL) were added to a 250 mL reaction flask, then NaOH (5 g) and DMSO (50 mL) were added and heated to 100° C. The reaction condition was the same as done in Example 2. After the cyclization and purification, the desired product VIc was obtained. Total yield for two steps: 47%.

1H-NMR for the product VIc (CDCl3, 500 MHz): δ 10.09 (s, 214), 6.96-6.94 (d, J=8.0 Hz, 1H), 6.92-6.90 (d, J=7.5 Hz, 1H), 4.40-4.39 (m, 4H), 4.20-4.17 (t, J=5.0 Hz, 2H), 4.13-

4.11 (t, J=5.0 Hz, 2H), 2.19-2.09 (m, 2H). ESI-MS [(M+H)+]: m/z calculated 192.1, founded 192.1.

Example 4

Synthesis of Ru Complex VId

SM-2 (12 g, 0.5 mol) and Br(CH2)3Br (20 mL) were added to a 250 mL reaction flask, then NaOH (5 g) and DMSO (50 mL) were added and heated to 100° C. The reaction condition was the same as done in Example 2. After the cyclization and purification, the desired product VIc was obtained. Total yield for two steps: 41%.

$^1$H-NMR for the product VId (CDCl3, 500 MHz): δ 6.86 (s, 211), 4.30 (brs, 1H), 4.20 (s, 4H), 4.15-4.17 (t, J=5.8 Hz, 4H), 2.16-2.18 (m, 2H). ESI-MS [(M+H)$^+$]: m/z calculated 192.1, founded 192.1.

Example 5

Synthesis of Compound VIe

SM-2 (12 g, 0.5 mol) and DCE (30 mL) were added to a 250 mL reaction flask, then NaOH (5 g) and DMSO (50 mL) were added and heated to 100° C. The reaction condition was the same as done in Example 2. After the cyclization and purification by flash column, the desired product VIe was obtained. Total yield for two steps: 56%.

1H-NMR for the product VIe (CDCl3, 500 MHz): δ 6.74 (s, 2H), 4.23 (s, 4H), 4.13 (s, 4H). ESI-MS (M+H+): m/z calculated 178.1, founded 178.2.

Example 6

Synthesis of Compound VIf

SM-2 (12 g, 0.5 mol) and DCM (100 mL) were added to a 250 mL reaction flask, then NaOH (5 g) and DMSO (50 mL) were added and heated to 100° C. The reaction condition was the same as done in Example 1. After the cyclization and purification by flash column, the desired product VIf was obtained. Total yield for two steps: 51%.

1H-NMR for the product VIf (CDCl3, 500 MHz): δ 6.69 (s, 2H), 5.95 (s, 2H), 4.14 (s, 4H). ESI-MS (M+H+): m/z calculated 164.1, founded 164.2.

Example 7

Synthesis of Compound 4a

SM-4 (5.37 g, 21.9 mmol) and CDI (14.2 g, 87.5 mmol, 4 eq.) were dissolved in 100 mL anhydrous dichloromethane (DCM) and stirred overnight, followed by adding another compound VIa (43.7 mmol, 2 eq.) until completed. The reaction mixture was worked out and purified by flash column to obtain the product 4a (5.2 g) was obtained, yield 71%.

$^1$H-NMR for the product 4a (CDCl$_3$, 500 MHz): δ 6.78-6.80 (m, 1H), 6.69-6.75 (m, 1H), 6.00 (s, 2H), 5.34 (m, 1H), 4.67-4.70 (d, J=13.5 Hz, 2H), 4.60-4.63 (d, J=15 Hz, 2H), 4.40-4.48 (m, 1H), 3.66-3.78 (m, 5H), 2.48 (m, 1H), 2.24-2.26 (m, 1H), 1.48 (s, 4H), 1.45 (s, 5H). ESI-MS (M+H$^+$): m/z calculated 435.2, founded 435.3.

Example 8

Synthesis of Compound 4b

SM-4 (5.37 g, 21.9 mmol) and CDI (14.2 g, 87.5 mmol, 4 eq.) were dissolved in 100 mL anhydrous dichloromethane and stirred at room temperature overnight, followed by adding another compound VIb (43.7 mmol, 2 eq.) until completed. The reaction mixture was worked out and purified by flash column to obtain the product 4b (6.1 g), yield 82%.

$^1$H-NMR for the product 4b (CDCl$_3$, 500 MHz): δ 6.81-6.84 (m, 1H), 6.68-6.75 (m, 1H), 5.33 (m, 1H), 4.67 (s, 2H), 4.60 (s, 2H), 4.39-4.48 (m, 1H), 4.30 (m, 2H), 4.28 (m, 2H), 3.63-3.79 (m, 5H), 2.47-2.49 (m, 1H), 2.22-2.26 (m, 1H), 1.48 (s, 2H), 1.45 (s, 5H). ESI-MS (M+H$^+$): m/z calculated 449.2, founded 449.3.

Example 9

Synthesis of Compound 4c

SM-4 (5.37 g, 21.9 mmol) and CDI (14.2 g, 87.5 mmol, 4 eq.) were dissolved in 100 mL anhydrous dichloromethane and stirred at room temperature overnight, followed by adding another compound VIc (43.7 mmol, 2 eq.) until completed. The reaction mixture was worked out and purified by flash column to obtain the product 4c (6.1 g), yield 82%.

The product 4c was confirmed by ESI-MS (M+H$^+$): m/z calculated 449.2, founded 449.3.

Example 10

Synthesis of Compound 4d

SM-4 (5.37 g, 21.9 mmol) and CDI (14.2 g, 87.5 mmol, 4 eq.) were dissolved in 100 mL anhydrous dichloromethane and stirred at room temperature overnight, followed by adding another compound VId (43.7 mmol, 2 eq.) until completed. The reaction mixture was worked out and purified by flash column to obtain the product 4d (6.1 g), yield 82%.

The product 4d was confirmed by ESI-MS (M+H$^+$): m/z calculated 449.2, founded 449.3.

Example 11

Synthesis of Compound 4e

SM-4 (5.37 g, 21.9 mmol) and CDI (14.2 g, 87.5 mmol, 4 eq.) were dissolved in 100 mL anhydrous dichloromethane and stirred at room temperature overnight, followed by adding another compound VIe (43.7 mmol, 2 eq.) until completed. The reaction mixture was worked out and purified by flash column to obtain the product 4e (5.7 g), yield 75%.

$^1$H-NMR for the product 4e (CDCl$_3$, 500 MHz): δ 6.77 (s, 1H), 6.73 (s, 1H), 5.32 (m, 1H), 4.63 (s, 2H), 4.56 (s, 2H), 4.37-4.48 (m, 1H), 4.26 (s, 4H), 3.64-3.79 (m, 5H), 2.47 (m, 1H), 2.21-2.26 (m, 1H), 1.48 (s, 4H), 1.44 (s, 5H). ESI-MS (M+H$^+$): m/z calculated 449.2, founded 449.3.

Example 12

Synthesis of Compound 4f

SM-4 (5.37 g, 21.9 mmol) and CDI (14.2 g, 87.5 mmol, 4 eq.) were dissolved in 100 mL anhydrous dichloromethane and stirred at room temperature overnight, followed by adding another compound VIf (43.7 mmol, 2 eq.) until completed. The reaction mixture was worked out and purified by flash column to obtain the product 4f (5.9 g), yield 74%.

$^1$H-NMR for the product 4f (CDCl$_3$, 500 MHz): δ 6.71 (s, 11-1), 6.67 (s, 1H), 5.97 (s, 2H), 5.32 (m, 1H), 4.63 (s, 2H), 4.57 (s, 2H), 4.38-4.47 (m, 1H), 3.64-3.76 (m, 5H), 2.47 (m, 1H), 2.23-2.25 (m, 1H), 1.47 (s, 4H), 1.44 (s, 5H). ESI-MS (M+H$^+$): m/z calculated 435.2, founded 435.3.

Example 13

Synthesis of Compound 6a

The product of 4a (2 g, 4.9 mmol) was dissolved in 40 mL 4N HCl/Et$_2$O solvent and stirred at 30° C. until the completely deprotecting of Boc to give product 5a.

The concentrated 5a was dissolved in 50 mL DMF, compound SM-5 (1.40 g, 5.14 mmol, 1.05 eq.) and HATU (2.05 g, 5.39 mmol, 1.1 eq.) were added. After cooled in ice bath for 15 minute, DIEA (2.53 g, 19.6 mmol, 4 eq.) was added dropwise, the mixture was warmed to room temperature and stirred overnight until completed (monitored by HPLC-ELSD). The organic layer was separated and the water phase was extracted twice with ethyl acetate (2×100 mL). The combined organic layer as was washed with 1N hydrochloric acid, water, saturated sodium bicarbonate, and brine, dried and evaporated, finally purified by flash column to obtain desired product 6a (2.5 g), yield 87%, confirmed by ESI-MS (M+H$^+$): in/z calculated: 588.3, founded: 588.3.

Example 14

Synthesis of Compound 7a

The product of 6a (2.3 g, 4.2 mmol) was dissolved in 30 mL THF, 15 mL methanol and 15 mL water. Lithium hydroxide monohydrate (0.54 g, 12.8 mmol, 3 eq.) was added and stirred overnight until completed. The reaction mixture was worked out and purified by flash column to obtain the product 7a (2.1 g), yield >95%, confirmed by ESI-MS (M+H$^+$): m/z calculated 574.3, founded 574.4.

Example 15

Synthesis of Compound 8

The raw material SM-7 (6.5 g, 18 mmol) was dissolved in HCl/Et$_2$O solution (4M, 80 mL) and stirred at 30° C. until completed.

The above de-Boc product was concentrated and dissolved in 150 mL DMF. Compound (L)-N-Boc-2-amino-8-azelaic acid (SM-5, 5.2 g, 19 mmol, 1.05 eq.) and HATU (7.6 g, 20 mmol, 1.1 eq.) were added. After cooled in ice bathed for 15 minute, DIEA (9.5 g, 76 mmol, 4 eq.) was added dropwise, the mixture was warmed to room temperature and stirred overnight until completed. The reaction mixture was worked out and purified by flash column to obtain the product 8 (2.5 g), yield 87%.

$^1$H-NMR for the product 8 (CDCl3, 500 MHz): δ 7.73 (s, 1H), 5.70-5.79 (m, 2H), 5.27-5.31 (d, 1H, J=17 Hz), 5.22-5.24 δ (d, 1H, J=8 Hz), 5.11-5.13 (m, 1H), 4.93-5.01 (m, 2H), 4.68-4.71 (t, 1H, J=7.5 Hz), 4.54 (br, 1H), 4.36-4.37 (m, 1H), 3.94-3.97 (d, 1H, J=11.5 Hz), 3.65 (s, 3H), 3.55-3.58 (m, 1H), 3.39 (br, 1H), 2.97 (s, 1H), 2.89 (s, 1H), 2.49-2.52 (m, 1H), 2.12-2.16 (m, 1H), 2.02-2.04 (m, 4H), 1.83-1.85 (m, 1H), 1.74-1.78 (m, 1H), 1.59-1.61 (m, 1H), 1.43 (s, 9H), 1.31-1.40 (m, 4H), confirmed by ESI-MS (M+H$^+$): m/z calculated: 508.3, founded: 508.5.

Example 16

Synthesis of Compound 9a

The two methods of synthesis of compounds 9a-9d shown above.

Method I:

The product 7a (2.0 g, 4 mmol) and vinyl substituted cyclopropyl amino acid methyl ester reagents SM-6 (1.3 g, 4.2 mmol, 1.05 eq.) and the coupling reagent HATU (1.83 g, 4.82 mmol, 1.1 eq.) were dissolved in 80 mL DMF. After cooled in ice bathed for 15 minute, DIEA (2.27 g, 17.5 mmol, 4 eq.) was added dropwise, the mixture was warmed to room temperature and stirred overnight, followed by adding the product VIa (5.12 mmol, 2 eq.) until completed. The reaction mixture was worked out and purified by flash column to obtain the product 9a (2.4 g), yield 81%, confirmed by ESI-MS (M+H$^+$): m/z calculated 699.3, founded 699.4.

Method II:

The product of the above Experiment 9 8 (1.3 g, 2.56 mmol) and CDI (1.66 g, 10.2 mmol, 4 eq.) were dissolved in 50 mL anhydrous dichloromethane and stirred at room temperature overnight. When HPLC-ELSD shows the reaction was completed, the product of Experiment 1 VIa (5.12 mmol, 2 eq.) was added and stirred at room temperature until completed. The reaction mixture was worked out and purified by flash column to obtain the product 9a (1.4 g), yield 86%, confirmed by ESI-MS (M+H$^+$): m/z calculated: 699.3, founded: 699.4.

Example 17

Synthesis of Compound 9b

The synthesis of compounds 9b adopted method II shown above: the product 8 (1.3 g, 2.56 mmol) and CDI (1.66 g, 10.2 mmol, 4 eq.) were dissolved in 50 mL of anhydrous dichloromethane at room temperature overnight, followed by adding the product VIb (5.12 mmol, 2 eq.) until completed. The reaction mixture was worked out and purified by flash column to obtain the product 9b (1.6 g), yield 94%, confirmed by ESI-MS (M+H$^+$): m/z calculated 711.4, founded 711.5.

Example 18

Synthesis of Compound 9c

The synthesis of compounds 9c adopted method II shown above: the product 8 (1.3 g, 2.56 mmol) and CDI (1.66 g, 10.2 mmol, 4 eq.) were dissolved in 50 mL of anhydrous dichloromethane at room temperature overnight, followed by adding the product VIc (5.12 mmol, 2 eq.) until completed. The reaction mixture was worked out and purified by flash column to obtain the product 9c (1.3 g), yield 77%, confirmed by ESI-MS (M+H$^+$): m/z calculated 711.4, founded 711.5.

Example 19

Synthesis of Compound 9d

The synthesis of compounds 9d adopted method II shown above: the product 8 (1.3 g, 2.56 mmol) and CDI (1.66 g, 10.2 mmol, 4 eq.) were dissolved in 50 mL of anhydrous dichloromethane at room temperature overnight, followed by adding the product VId (5.12 mmol, 2 eq.) until completed. The reaction mixture was worked out and purified by flash column to obtain the product 9d (1.3 g), yield 77%, confirmed by ESI-MS (M+H$^+$): m/z calculated 711.4, founded 711.5.

Example 20

Synthesis of Compound 9e

The synthesis of compounds 9e adopted method II shown above: the product of the above mentioned Experiment 9 8

(1.3 g, 2.56 mmol) and CDI (1.66 g, 10.2 mmol, 4 eq.) were dissolved in 50 mL of anhydrous dichloromethane at room temperature overnight, followed by adding the product VIe (5.12 mmol, 2 eq.) until completed. The reaction mixture was worked out and purified by flash column to obtain the product 9e (1.4 g), yield 83%, and confirmed by ESI-MS (M+H$^+$): m/z calculated 711.4, founded 711.5.

Example 21

Synthesis of Compound 9f

The synthesis of compounds 9f adopted method II shown above: the product 8 (1.3 g, 2.56 mmol) and CDI (1.66 g, 10.2 mmol, 4 eq.) were dissolved in 50 mL of anhydrous dichloromethane at room temperature overnight, followed by adding the product VIf (5.12 mmol, 2 eq.) until completed. The reaction mixture was worked out and purified by flash column to obtain the product 9f (1.3 g), yield 78%, and confirmed by ESI-MS (M+H$^+$): m/z calculated: 697.3, founded: 697.4.

Example 22

Synthesis of Compound 9-Ref

Synthesis of compounds 9-Ref adopted method II shown above: the product 8 (1.3 g, 2.56 mmol) and CDI (1.66 g, 10.2 mmol, 4 eq.) were dissolved in 50 mL of anhydrous DCE at room temperature overnight, followed by adding another compound SM-8 (43.7 mmol, 2 eq.) until completed. The reaction mixture was worked out and purified by flash column to obtain the product 9e (1.4 g), yield 81%.

$^1$H-NMR for the product 9-Ref (CDCl$_3$, 500 MHz): δ 7.65-7.70 (d, 1H, J=9 Hz), 6.96-7.07 (m, 2H), 5.72-5.78 (m, 2H), 5.40 (br, 1H), 5.28-5.31 (d, 1H, J=16.5 Hz), 5.12-5.14 (d, 1H, J=10.5 Hz), 5.07-5.09 (d, 1H, J=7.5 Hz), 4.93-5.00 (m, 2H), 4.64-4.79 (m, 5H), 4.36-4.37 (m, 1H), 4.06 (m, 1H), 3.72-3.75 (m, 1H), 3.67 (s, 3H), 2.78 (m, 1H), 2.26 (m, 1H), 2.14-2.16 (m, 1H), 2.01-2.03 (m, 2H), 1.86-1.88 (m, 1H), 1.70-1.73 (m, 1H), 1.57-1.60 (m, 1H), 1.45-1.49 (m, 2H), 1.37-1.40 (m, 4H), 1.32 (s, 4H), 1.29 (s, 5H), and confirmed by Mass spectrometry, ESI-MS (M+H$^+$): m/z calculated 691.3, founded 691.4.

Example 23

Synthesis of Compound 10a

Under argon protection atmosphere, compound 9a (2.25 mmol) was dissolved in 450 mL of anhydrous dichloromethane, and Zhan Catalyst-1B (RC-303, 74.4 mg, 0.113 mmol, 0.05 eq.) was added. The reaction flask was stirred in a preheated oil bath at 80° C. overnight until completed. The reaction mixture was worked out and purified by flash column to obtain the product 10a (1.2 g), yield 64%, and confirmed by ESI-MS (M+H$^+$): m/z calculated 669.3, founded 669.4.

Example 24

Synthesis of Compound 10b

Under argon protection atmosphere, compound 9b (2.25 mmol) was dissolved in 450 mL of anhydrous dichloromethane, and Zhan Catalyst-1B (RC-303, 74.4 mg, 0.113 mmol, 0.05 eq.) was added. The reaction flask was stirred in a preheated oil bath at 80° C. overnight until completed. The reaction mixture was worked out and purified by flash column to obtain the product 10b (1.3 g), yield 67%, and confirmed by ESI-MS (M+H$^+$): m/z calculated 683.3, founded 683.5.

Example 25

Synthesis of Compound 10c

Under argon protection atmosphere, compound 9c (2.25 mmol) was dissolved in 450 mL of anhydrous dichloromethane, and Zhan Catalyst-1B (RC-303, 74.4 mg, 0.113 mmol, 0.05 eq.) was added. The reaction flask was stirred in a preheated oil bath at 80° C. overnight until completed. The reaction mixture was worked out and purified by flash column to obtain the product 10c (1.2 g), yield 56%, and confirmed by ESI-MS (M+H$^+$): m/z calculated 683.3, founded 683.5.

Example 2

Synthesis of Compound 10d

Under argon protection atmosphere, compound 9d (2.25 mmol) was dissolved in 450 mL of anhydrous dichloromethane, and Zhan Catalyst-1B (RC-303, 74.4 mg, 0.113 mmol, 0.05 eq.) was added. The reaction flask was stirred in a preheated oil bath at 80° C. overnight until completed. The reaction mixture was worked out and purified by flash column to obtain the product 10d (1.3 g), yield 61%, and confirmed by ESI-MS (M+H$^+$): m/z calculated 683.3, founded 683.5.

Example 27

Synthesis of Compound 10e

Under argon protection atmosphere, compound 9e (2.25 mmol) was dissolved in 450 mL of anhydrous dichloromethane, and Zhan Catalyst-1B (RC-303, 74.4 mg, 0.113 mmol, 0.05 eq.) was added. The reaction flask was stirred in a preheated oil bath at 80 V overnight until completed. The reaction mixture was worked out and purified by flash column to obtain the product 10e (1.1 g), yield 51%, and confirmed by ESI-MS (M+H$^+$): m/z calculated 683.3, founded 683.5.

Example 28

Synthesis of Compound 10f

Under argon protection atmosphere, compound 9f (2.25 mmol) was dissolved in 450 mL of anhydrous dichloromethane, and Zhan Catalyst-1B (RC-303, 74.4 mg, 0.113 mmol, 0.05 eq.) was added. The reaction flask was stirred in a preheated oil bath at 80 V overnight until completed. The reaction mixture was worked out and purified by flash column to obtain the product 10f (0.9 g), yield 47%, and confirmed by ESI-MS (M+H$^+$): m/z calculated 669.3, founded 669.4.

Example 29

Synthesis of Compound 10-Ref

Under argon protection atmosphere, compound 9-Ref (2.25 mmol) was dissolved in 450 mL of anhydrous dichloromethane, and Zhan Catalyst-1B (RC-303, 74.4 mg, 0.113 mmol, 0.05 eq.) was added. The reaction flask was stirred in a preheated oil bath at 80 V overnight until completed. The reaction mixture was worked out and purified by flash column to obtain the product 10-Ref (1.4 g), yield 71%.

¹H-NMR for the product 10-Ref (CDCl₃, 500 MHz): δ 6.96-7.07 (m, 3H), 5.53-5.55 (m, 1H), 5.39 (m, 1H), 5.23-5.28 (m, 2H), 4.69-4.84 (m, 5H), 4.49 (m, 1H), 4.05-4.07 (m, 1H), 3.86-3.89 (m, 1H), 3.67 (s, 3H), 2.82-2.85 (m, 1H), 2.25-2.27 (m, 1H), 2.16-2.19 (m, 3H), 1.85-1.88 (m, 2H), 1.56-1.73 (m, 3H), 1.38-1.43 (m, 4H), 1.35 (s, 4H), 1.34 (s, 5H), and confirmed by ESI-MS (M+H⁺): m/z calculated 643.3, founded 643.5.

Example 30

Synthesis of Compound 11a

The compound 10a (0.6 mmol) was dissolved in 30 mL THF, 15 mL methanol and 15 mL water. Lithium hydroxide monohydrate (122.9 mg, 2.93 mmol, 5 eq.) was added and stirred overnight until completed. The reaction mixture was worked out and purified by flash column to obtain the product 11a (466 mg), yield>95%, and confirmed by ESI-MS (M+H⁺): m/z calculated 655.3, founded 655.3.

Example 31

Synthesis of Compound 11b

The compound 10b (0.6 mmol) was dissolved in 30 mL THF, 15 mL methanol and 15 mL water. Lithium hydroxide monohydrate (122.9 mg, 2.93 mmol, 5 eq.) was added and stirred overnight until completed. The reaction mixture was worked out and purified by flash column to obtain the product 11b (439 mg), yield>95%, and confirmed by ESI-MS (M+H⁺): m/z calculated 669.3, founded 669.3.

Example 32

Synthesis of Compound 11c

The compound 10c (0.6 mmol) was dissolved in 30 mL THF, 15 mL methanol and 15 mL water. Lithium hydroxide monohydrate (122.9 mg, 2.93 mmol, 5 eq.) was added and stirred overnight until completed. The reaction mixture was worked out and purified by flash column to obtain the product 11e (453 mg), yield>95%, and confirmed by ESI-MS (M+H⁺): m/z calculated 673.3, founded 673.3.

Example 33

Synthesis of Compound 11d

The compound 10d (0.6 mmol) was dissolved in 30 mL THF, 15 mL methanol and 15 mL water. Lithium hydroxide monohydrate (122.9 mg, 2.93 mmol, 5 eq.) was added and stirred overnight until completed. The reaction mixture was worked out and purified by flash column to obtain the product 11d (457 mg), yield>95%, and confirmed by ESI-MS (M+H⁺): m/z calculated 673.3, founded 673.3.

Example 34

Synthesis of Compound 11e

The compound 10e (0.6 mmol) was dissolved in 30 mL THF, 15 mL methanol and 15 mL water. Lithium hydroxide monohydrate (122.9 mg, 2.93 mmol, 5 eq.) was added and stirred overnight until completed. The reaction mixture was worked out and purified by flash column to obtain the product 11e (418 mg), yield 85%, and confirmed by ESI-MS (M+H⁺): m/z calculated 669.3, founded 669.3.

Example 35

Synthesis of Compound 11f

The compound 10f (0.6 mmol) was dissolved in 30 mL THF, 15 mL methanol and 15 mL water. Lithium hydroxide monohydrate (122.9 mg, 2.93 mmol, 5 eq.) was added and stirred overnight until completed. The reaction mixture was worked out and purified by flash column to obtain the product 11f (453 mg), yield>95%, and confirmed by ESI-MS (M+H⁺): m/z calculated 655.3, founded 655.4.

Example 36

Synthesis of Compound 11j

Compound 10e (0.55 g, 0.81 mmol) was suspended in 10 mL 4N HCl/ether solvent, stirred for 2 h and concentrated. 10 mL DCM and triethylamine (0.82 g, 8 mmol) were added and cooled to 0-5° C. The raw material sulfonyl chloride (0.29 g, 1.6 mmol) was added slowly and the reaction was stirred at room temperature overnight until completed. The reaction mixture was worked out and purified by flash column, and the product 13j (0.43 g, yield: 73%).

Compound 13j (0.4 g) was to added to the mixture solvent of NaOH (120 mg, 3 mmol), 10 mL methanol and 0.5 mL of water. The reaction mixture was stirred at 60° C. for 5 hr until completed. The reaction mixture was worked out and purified by flash column to obtain the product 11j (0.31 g, yield: 80%).

¹H-NMR for the product 11j (CDCl₃, 500 MHz): δ 7.30 (s, 1H); 6.76 (s, 1H); 6.68 (s, 1H); 5.69 (q, J=8.0Hz, 1H); 5.48 (s, 1H); 5.15 (t, J=8.0 Hz, 1H); 4.63-4.48 (m, 5H); 4.24 (s, 4H); 4.23-4.14 (m, 2H); 3.86 (m, 1H); 3.71 (m, 1H); 3.39 (m, 1H); 3.07-2.91 (m, 2H); 2.57 (m, 1H); 2.44 (m, 1H); 2.36-2.22 (br, 4H); 2.04 (m, 1H); 1.93 (m, 1H); 1.81 (m, 1H); 1.64-1.55 (br, 3H); 1.46-1.29 (br, 4H); 1.24-1.20 (br, 2H), and confirmed by ESI-MS (M+H⁺): in/z calculated 673.2, founded 673.3.

Example 37

Synthesis of Compound 11k

The synthesis of compound 11k was the same as 11j.

Compound 10f (0.55 g, 0.81 mmol) was suspended in 10 mL 4N HCl/ether solvent, stirred for 2 h and concentrated. 10 mL DCM and triethylamine (0.82 g, 8 mmol) were added and cooled to 0-5° C. The raw material sulfonyl chloride (0.29 g, 1.6 mmol) was added slowly and the reaction was stirred at room temperature overnight until completed. The reaction mixture was worked out and purified by flash column, and the product 13k (0.48 g, yield: 91%).

Compound 13k (0.4 g) was added to the mixture solvent of NaOH (120 mg, 3 mmol), 10 mL methanol and 0.5 mL of water. The reaction mixture was stirred at 60° C. for 5 hr until completed. The reaction mixture was worked out and purified by flash column to obtain the product 11k (0.30 g, yield: 78%).

¹H-NMR for the product 11k (CDCl₃, 500 MHz): δ 7.32 (s, 1H); 6.71 (s, 1H); 6.63 (s, 2H); 5.96 (s, 2H); 5.69 (q, J=8.0Hz, 1H); 5.48 (s, 1H); 5.15 (t, J=8.0 Hz, 1H); 4.64-4.49 (m, 5H); 4.23-4.15 (m, 2H); 3.89 (m, 1H); 3.72 (m, 1H); 3.40 (m, 1H); 3.09-2.89 (m, 2H); 2.58 (m, 1H); 2.48 (m, 1H); 2.39-2.26 (br, 4H); 2.08 (m, 1H); 1.96 (m, 1H); 1.82 (m, 1H); 1.69-1.54 (br, 3H); 1.46-1.29 (br, 4H); 1.26-1.20 (br, 2H) and confirmed by ESI-MS (M+H$^+$): m/z calculated 659.2, founded 659.3.

Example 38

Synthesis of Compound 11m

The synthesis of compound 11m was the same as 11j.
Compound 10-Ref (0.55 g, 0.81 mmol) was suspended in 10 mL 4N HCl/ether solvent, stirred for 2 h and concentrated. 10 mL DCM and triethylamine (0.82 g, 8 mmol) were added and cooled to 0-5° C. The raw material sulfonyl chloride (0.29 g, 1.6 mmol) was added slowly and the reaction was stirred at room temperature overnight until completed. The reaction mixture was worked out and purified by flash column, and the product 13m (0.35 g, yield: 65%).
Compound 13m (0.3 g) was added to the mixture solvent of NaOH (120 mg, 3 mmol), 10 mL methanol and 0.5 mL of water. The reaction mixture was stirred at 60° C. for 5 hr until completed. The reaction mixture was worked out and purified by flash column to obtain the product 11m (0.21 g, yield: 76%).
$^1$H-NMR for the product 11m (CDCl$_3$, 500 MHz): δ 7.25 (m, 1H); 7.06-6.95 (m, 2H); 5.71 (q, J=8.0 Hz, 1H); 5.49 (s, 1H); 5.32 (s, 1H); 5.14 (t, J=8.0 Hz, 1H); 4.80-4.4.61 (m, 5H); 4.31 (m, 1H); 4.16 (m, 1H); 3.86 (m, 1H); 3.72 (q, J=5.6 Hz, 1H); 3.40 (q, J=5.6 Hz, 1H); 3.02 (m, 1H); 2.92 (m, 1H); 2.61 (br, 1H); 2.52-2.41 (br, 2H); 2.33-2.24 (br, 3H); 2.06 (br, 1H); 1.93 (br, 1H); 1.83 (br, 1H); 1.63-1.54 (br, 3H); 1.42-1.22 (br, 6H) and confirmed by ESI-MS (M+H$^+$): m/z calculated 633.2, founded 633.3.

Example 39

Synthesis of compound 11-Ref

Synthesis of compound 11-Ref was the same as 11a.
The compound 10-Ref (0.6 mmol) was dissolved in 30 mL THF, 15 mL methanol and 15 mL water. Lithium hydroxide monohydrate (122.9 mg, 2.93 mmol, 5 eq.) was added and stirred overnight until completed. The reaction mixture was worked out and purified by flash column to obtain the product 11-Ref (438 mg), yield>95%.
$^1$H-NMR for the product 11-Ref (CDCl$_3$, 500 MHz): δ 7.16 (m, 1H), 6.96-7.07 (m, 2H), 5.63-5.64 (m, 1H), 5.32 (m, 1H), 5.20-5.28 (m, 2H), 4.68-4.78 (m, 5H), 4.34-4.40 (m, 1H), 4.19 (m, 1H), 3.89 (m, 1H), 2.68-2.78 (m, 1H), 2.32 (m, 2H), 2.21 (m, 1H), 2.10 (m, 1H), 1.84-1.87 (m, 2H), 1.59-1.62 (m, 2H), 1.40-1.45 (m, 5H), 1.32 (s, 4H), 1.30 (s, 5H) and confirmed by ESI-MS (M+H$^+$): m/z calculated 629.3, founded 629.4.

Example 40

Synthesis of Compound 12a

Compound 11a (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.
The obtained solid mixture above was dissolved in 10 mL of anhydrous DCE, DBU (61.0 mg, 0.40 mmol) and RSO$_2$NH$_2$ (0.36 mmol, R=cyclopropyl) were added and stirred at room temperature overnight until completed. The reaction mixture was worked out and purified by flash column to obtain the product 12a (56 mg; Yield: 58%).

$^1$H-NMR for the product 12a (CDCl$_3$, 500 MHz): δ 10.29-10.30 (d, 1H), 6.97-7.02 (d, 2H), 6.60-6.78 (m, 2H), 5.98-5.99 (m, 2H), 5.70-5.73 (m, 1H), 5.47 (m, 1H), 4.98-5.08 (m, 2H), 4.56-4.70 (m, 5H), 4.37-4.40 (m, 1H), 4.21-4.23 (m, 1H), 3.84-3.86 (m, 1H), 2.90-2.93 (m, 1H), 2.50-2.56 (m, 2H), 2.46-2.48 (m, 1H), 2.25-2.28 (m, 1H), 1.89-1.95 (m, 2H), 1.74-1.79 (m, 2H), 1.46-1.58 (m, 6H), 1.36-1.39 (m, 2H), 1.29 (s, 4H), 1.25 (s, 5H), 1.08-1.16 (m, 2H), 0.90-0.95 (m, 1H); and confirmed by ESI-MS (M+H$^+$): m/z calculated 758.3, founded 758.4.

Example 41

Synthesis of Compound 12b

Compound 11b (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.
The obtained solid mixture was dissolved in 10 mL of anhydrous dichloromethane, DBU (61.0 mg, 0.40 mmol) and RSO$_2$NH$_2$ (0.36 mmol, R=cyclopropyl) were added and stirred at room temperature overnight until completed. The reaction mixture was worked out and purified by flash column to obtain the product 12b (53 mg; Yield: 51%).
$^1$H-NMR for the product 12b (CDCl$_3$, 500 MHz): δ 10.25-10.25 (d, 1H), 6.88-6.91 (m, 1H), 6.77-6.80 (m, 1H), 6.58-6.60 (m, 1H), 5.68-5.74 (m, 1H), 5.45 (m, 1H), 4.98-5.06 (m, 2H), 4.64-4.68 (m, 2H), 4.52-4.60 (m, 3H), 4.35-4.39 (m, 1H), 4.22-4.29 (m, 5H), 3.82-3.84 (m, 1H), 2.88-2.91 (m, 1H), 2.45-2.56 (m, 2H), 2.41-2.45 (m, 1H), 2.23-2.29 (m, 1H), 1.82-1.93 (m, 1H), 1.60-1.79 (m, 3H), 1.36-1.56 (m, 8H), 1.23-1.29 (m, 9H), 0.93-1.06 (m, 2H), 0.89-0.93 (m, 1H); and confirmed by ESI-MS (M+H$^+$): m/z calculated 772.3, founded 773.4.

Example 42

Synthesis of Compound 12c

Compound 11e (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.
The obtained solid mixture was dissolved in 10 mL of anhydrous dichloromethane, DBU (61.0 mg, 0.40 mmol) and RSO$_2$NH$_2$ (0.36 mmol, R=cyclopropyl) were added and stirred at room temperature overnight until completed. The reaction mixture was worked out and purified by flash column to obtain the product 12c (47 mg; Yield: 42%).
$^1$H-NMR for the product 12c (CDCl$_3$, 500 MHz): δ 10.27 (s, 1H), 6.92 (s, 1H), 6.77 (s, 1H), 6.65 (s, 1H), 5.72-5.73 (m, 1H), 5.46 (m, 1H), 5.09 (m, 1H), 5.00 (m, 1H), 4.64 (m, 2H), 4.53-4.56 (m, 3H), 4.37-4.40 (m, 1H), 4.25 (m, 5H), 3.84-3.86 (m, 1H), 2.90 (m, 1H), 2.46-2.53 (m, 3H), 2.27-2.29 (m, 1H), 1.87-1.94 (m, 2H), 1.72 (m, 2H), 1.58 (m, 1H), 1.47 (m, 5H), 1.38 (m, 2H), 1.31 (s, 9H), 1.11 (m, 2H), 0.91 (m, 1H); and confirmed by ESI-MS (M+H$^+$): m/z calculated 772.3, founded 773.4.

Example 43

Synthesis of Compound 12d

Compound 11f (0.18 mmol) was dissolved in 10 mL anhydrous dichloromethane, EDCI (69.8 mg, 0.36 mmol, 2 eq.)

was added and stirred at room temperature overnight until completed. The reaction mixture was worked out and concentrated.

The obtained solid mixture was dissolved in 10 mL of anhydrous dichloromethane, DBU (61.0 mg, 0.40 mmol) and $RSO_2NH_2$ (0.36 mmol, R=cyclopropyl) were added and stirred at room temperature overnight until completed. The reaction mixture was worked out and purified by flash column to obtain the product 12d (65 mg; Yield: 67%).

$^1$H-NMR for the product 12d (CDCl$_3$, 500 MHz): δ 10.24 (s, 1H), 6.80 (s, 1H), 6.72 (s, 1H), 6.59 (s, 1H), 5.98 (s, 2H), 5.70-5.76 (m, 1H), 5.47 (m, 1H), 5.03 (m, 2H), 4.65 (m, 2H), 4.53-4.57 (m, 3H), 4.38-4.41 (m, 1H), 4.23 (m, 1H), 3.85 (d, 1H), 2.92 (m, 1H), 2.51-2.57 (m, 2H), 2.45 (m, 1H), 2.28 (m, 1H), 1.95 (m, 2H), 1.59 (m, 1H), 1.59-1.65 (m, 2H), 1.48 (m, 5H), 1.38 (m, 2H), 1.30 (s, 9H), 1.12 (m, 2H), 0.92 (m, 1H). ESI-MS (M+H$^+$): m/z calculated 758.3, founded 758.5.

Example 44

Synthesis of Compound 12e

Compound 11a (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid mixture was dissolved in 10 mL of anhydrous dichloromethane, DBU (61.0 mg, 0.40 mmol) and $RSO_2NH_2$ (0.363 mmol, R=isopropyl) were added and stirred at room temperature overnight until completed. The reaction mixture was worked out and purified by flash column to obtain the product 12e (53 mg; Yield: 49%).

$^1$H-NMR for the product 12e (CDCl$_3$, 500 MHz): δ 9.91-9.93 (d, 1H), 6.72-6.83 (m, 3H), 5.95-5.99 (m, 2H), 5.72-5.73 (m, 1H), 5.47 (m, 1H), 4.99-5.05 (m, 2H), 4.57-4.71 (m, 5H), 4.40-4.42 (m, 1H), 4.22 (m, 1H), 3.83-3.85 (d, 1H), 3.70-3.72 (m, 1H), 2.55-2.57 (m, 2H), 2.46-2.48 (m, 1H), 2.27-2.30 (m, 1H), 1.97 (m, 1H), 1.76-1.86 (m, 3H), 1.42-1.46 (m, 6H), 1.32-1.37 (m, 4H), 1.24-1.28 (d, 9H), 0.89-0.91 (m, 3H). ESI-MS (M+H$^+$): m/z calculated 760.3, founded 760.4.

Example 45

Synthesis of Compound 12f

Compound 11b (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid mixture was dissolved in 10 mL of anhydrous dichloromethane, DBU (61.0 mg, 0.40 mmol) and $RSO_2NH_2$ (0.363 mmol, R=isopropyl) were added and stirred at room temperature overnight until completed. The reaction mixture was worked out and purified by flash column to obtain the product 12f (50 mg; Yield: 46%).

$^1$H-NMR for the product 12f (CDCl$_3$, 500 MHz): δ 9.94 (s, 1H), 6.73-6.78 (m, 2H), 6.59-6.73 (m, 1H), 5.69-5.75 (m, 1H), 5.47 (m, 1H), 4.99-5.05 (m, 2H), 4.63-4.67 (m, 2H), 4.42-4.53 (m, 3H), 4.29-4.38 (m, 1H), 4.25-4.29 (m, 5H), 3.83-3.86 (m, 1H), 3.68-3.75 (m, 1H), 2.53-2.58 (m, 2H), 2.43-2.48 (m, 1H), 2.28-2.30 (m, 1H), 1.96-2.00 (m, 1H), 1.69-1.93 (m, 3H), 1.42-1.47 (m, 6H), 1.32-1.44 (m, 4H), 1.24-1.29 (m, 9H), 0.86-0.93 (m, 3H); and confirmed by ESI-MS (M+H$^+$): m/z calculated 774.3, founded 774.4.

Example 46

Synthesis of Compound 12g

Compound 11c (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid mixture was dissolved in 10 mL of anhydrous dichloromethane, DBU (61.0 mg, 0.40 mmol) and $RSO_2NH_2$ (0.363 mmol, R=isopropyl) were added and stirred at room temperature overnight until completed. The reaction mixture was worked out to obtain the white solid product 12g (45 mg; Yield: 38%).

$^1$H-NMR for the product 12g (CDCl$_3$, 500 MHz): δ 9.91 (s, 1H), 6.77-6.78 (m, 2H), 6.65 (s, 1H), 5.69-5.75 (m, 1H), 5.47 (m, 1H), 5.01-5.03 (m, 2H), 4.60-4.64 (m, 2H), 4.53-4.60 (m, 3H), 4.39-4.42 (m, 1H), 4.26 (m, 5H), 3.84-3.85 (m, 1H), 3.69-3.72 (m, 1H), 2.54-2.56 (m, 2H), 2.43-2.48 (m, 1H), 2.28-2.29 (m, 1H), 1.96 (m, 1H), 1.74-1.86 (m, 2H), 1.59 (m, 1H), 1.37-1.43 (m, 7H), 1.32-1.33 (m, 15H); and confirmed by ESI-MS (M+H$^+$): m/z calculated 774.3, founded 774.4.

Example 47

Synthesis of Compound 12h

Compound 11d (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid mixture was dissolved in 10 mL of anhydrous dichloromethane, DBU (61.0 mg, 0.40 mmol) and $RSO_2NH_2$ (0.363 mmol, R=isopropyl) were added and stirred at room temperature overnight until completed. The reaction mixture was worked out and purified by flash column to obtain the product 12h (53 mg; Yield: 48%).

$^1$H-NMR for the product 12h (CDCl$_3$, 500 MHz): δ 9.95 (s, 1H), 6.90 (s, 1H), 6.71 (s, 1H), 6.59 (s, 1H), 5.98 (s, 2H), 5.73 (m, 1H), 5.47 (m, 1H), 5.04 (m, 2H), 4.65 (m, 2H), 4.53-4.57 (m, 3H), 4.39-4.41 (m, 1H), 4.23 (m, 1H), 3.84-3.85 (d, 1H), 3.70 (m, 1H), 2.53 (m, 2H), 2.48 (m, 1H), 2.28 (m, 1H), 1.95 (m, 1H), 1.76-1.86 (m, 3H), 1.57 (m, 1H), 1.41-1.46 (m, 7H), 1.30 (m, 15H); and confirmed by ESI-MS (M+H$^+$): m/z calculated 760.3, founded 760.4.

Example 48

Synthesis of Compound 12j

Compound 11j (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid mixture was dissolved in 10 mL of anhydrous dichloromethane, DBU (61.0 mg, 0.40 mmol) and $RSO_2NH_2$ (0.363 mmol, R=cyclopropyl) were added and stirred at room temperature overnight until completed. The reaction mixture was worked out and purified by flash column to obtain the product 12j (73 mg; Yield: 61%).

$^1$H-NMR for the product 12j (CDCl$_3$, 500 MHz): δ 10.35 (s, 1H), 7.35 (s, 1H), 6.74 (s, 1H), 6.67 (s, 1H), 5.72-5.77 (q, 1H, J=8.5 Hz), 5.52 (m, 1H), 5.00-5.04 (t, 1H, J=9.5 Hz), 4.57-4.64 (m, 2H), 4.46-4.57 (m, 3H), 4.23-4.25 (m, 5H), 4.08-4.11 (d, 1H), 3.88-3.90 (m, 1H), 3.65-3.69 (m, 1H), 3.32-3.37 (m, 1H), 2.92-3.05 (m, 2H), 2.88-2.92 (m, 1H), 2.66-2.74 (m, 1H), 2.40-2.53 (m, 2H), 2.26-2.35 (m, 3H), 1.80-2.05 (m, 3H), 1.48-1.68 (m, 3H), 1.26-1.48 (m, 6H), 1.08-1.13 (m, 2H), 0.90-0.94 (m, 1H). ESI-MS (M+H$^+$): m/z calculated 776.3, founded 776.4.

Example 49

Synthesis of Compound 12k

Compound 11k (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid was dissolved in 10 mL of anhydrous dichloromethane, DBU (61.0 mg, 0.40 mmol) and RSO$_2$NH$_2$ (0.363 mmol, R=cyclopropyl) were added and stirred at room temperature overnight until completed. The reaction mixture was worked out and purified by flash column to obtain the product 12k (54 mg; Yield: 38%).

$^1$H-NMR for the product 12k (CDCl$_3$, 500 MHz): δ 10.36 (s, 1H), 7.39 (s, 1H), 6.70 (s, 1H), 6.64 (s, 1H), 5.97 (s, 2H), 5.74-5.76 (m, 2H), 5.53 (m, 1H), 5.01-5.05 (t, 1H, J=9.5 Hz), 4.46-4.64 (m, 5H), 4.24-4.26 (d, 1H), 4.10-4.13 (m, 1H), 3.88-3.91 (m, 1H), 3.66-3.68 (m, 1H), 3.33-3.38 (m, 1H), 2.90-3.03 (m, 3H), 2.71 (m, 1H), 2.49-2.51 (m, 1H), 2.42-2.45 (m, 1H), 2.28-2.34 (m, 3H), 1.81-2.02 (m, 4H), 1.62-1.69 (m, 4H), 1.44-1.49 (m, 4H), 1.08-1.14 (m, 2H), 0.86-0.96 (m, 1H). ESI-MS (M+H$^+$): m/z calculated 762.2, founded 762.3.

Example 50

Synthesis of Compound 12m

Compound 11m (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid was dissolved in 10 mL of anhydrous dichloromethane, DBU (61.0 mg, 0.40 mmol) and RSO$_2$NH$_2$ (0.363 mmol, R=cyclopropyl) were added and stirred at room temperature overnight until completed. The reaction mixture was worked out and purified by flash column to obtain the product 12m (61 mg; Yield: 52%).

$^1$H-NMR for the product 12m (CDCl$_3$, 500 MHz): δ 10.38-10.41 (d, 1H), 7.51-7.55 (d, 1H, J=20 Hz), 6.94-7.05 (m, 2H), 5.73-5.79 (m, 2H), 5.54 (m, 1H), 5.02-5.06 (t, 1H, J=9.5 Hz), 4.75-4.85 (m, 2H), 4.54-4.64 (m, 3H), 4.29-4.33 (t, 1H, J=11 Hz), 4.08-4.10 (d, 1H), 3.85-3.89 (m, 1H), 3.65-3.68 (m, 1H), 3.31-3.36 (m, 3H), 2.73-2.74 (m, 1H), 2.51-2.52 (m, 2H), 2.27-2.36 (m, 3H), 1.72-2.02 (m, 4H), 1.27-1.66 (m, 9H), 1.09-1.13 (m, 2H), 0.91-0.95 (m, 1H). ESI-MS (M+H$^+$): m/z calculated 736.2, founded 736.4.

Example 51

Synthesis of Compound 12n

Compound 11c (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid mixture was dissolved in 10 mL of anhydrous dichloromethane, DBU (61.0 mg, 0.40 mmol) and RSO$_2$NH$_2$ (0.36 mmol, R=cyclopropyl) were added and stirred at room temperature overnight until completed. The reaction mixture was worked out and purified by flash column to obtain the product 12n (47 mg; Yield: 42%).

$^1$H-NMR for the product 12n (CDCl$_3$, 500 MHz): δ10.27 (s, 1H), 6.89-6.92 (m, 2H), 6.67-6.79 (m, 1H), 5.72-5.74 (m, 1H), 5.46-5.47 (m, 1H), 4.99-5.07 (m, 2H), 4.55-4.69 (m, 5H), 4.39 (m, 1H), 4.21-4.25 (m, 5H), 3.84-3.86 (m, 1H), 2.90-2.93 (m, 1H), 2.45-2.56 (m, 3H), 2.19-2.29 (m, 3H), 1.89-1.95 (m, 2H), 1.71-1.79 (m, 2H), 1.58 (m, 1H), 1.34-1.50 (m, 7H), 1.29 (s, 5H), 1.25 (s, 4H), 1.08-1.16 (m, 2H), 0.92-0.94 (m, 1H). ESI-MS (M+H$^+$): m/z calculated 786.3, founded 786.4.

Example 52

Synthesis of Compound 12p

Compound 11d (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid mixture was dissolved in 10 mL of anhydrous dichloromethane, DBU (61.0 mg, 0.40 mmol) and RSO$_2$NH$_2$ (0.36 mmol, R=cyclopropyl) were added and stirred at room temperature overnight until completed. The reaction mixture was worked out and purified by flash column to obtain the product 12p (65 mg; Yield: 67%).

$^1$H-NMR for the product 12p (CDCl$_3$, 500 MHz): δ 10.28 (s, 1H), 7.00 (s, 1H), 6.87 (s, 1H), 6.75 (s, 1H), 5.70-5.72 (m, 1H), 5.45 (m, 1H), 4.97-5.09 (m, 2H), 4.52-4.63 (m, 5H), 4.35-4.38 (m, 1H), 4.14-4.22 (m, 5H), 3.83-3.84 (m, 1H), 2.88-2.91 (m, 1H), 2.44-2.53 (m, 3H), 2.17-2.27 (m, 3H), 1.76-1.91 (m, 4H), 1.57 (m, 1H), 1.37-1.51 (m, 7H), 1.28 (s, 9H), 1.06-1.13 (m, 2H), 0.89-0.93 (m, 1H). ESI-MS (M+H$^+$): m/z calculated 786.3, founded 786.4.

Example 53

Synthesis of Compound 12q

Compound 12d (0.18 mmol) was dissolved in 20 mL HCl-Et$_2$O (2N) and stirred at 30° C. until completed to obtain de-Boc product, followed by reacting with another reagent iPrOC(O)Cl (1.2 eq) to obtain the product 12q. yield: 72%.

$^1$H-NMR for the product 12q (CDCl$_3$, 500 MHz): δ10.27 (s, 1H), 6.97 (br, 1H), 6.70 (s, 1H), 6.59 (s, 1H), 5.95 (s, 2H), 5.70 (q, J=8.1 Hz, 1H), 5.44 (s, 1H), 5.14 (s, 1H), 4.99 (t, J=8.1 Hz, 1H), 4.65-4.47 (m, 5H), 4.35 (m, 2H), 4.24 (br, 1H), 3.82 (m, 1H), 2.91 (m, 1H), 2.45 (m, 3H), 2.23 (m, 1H), 1.92 (br, 2H), 1.74 (br, 2H), 1.59 (m, 1H), 1.47-1.27 (br, 8H), 1.11-1.06 (br, 5H), 1.01 (d, J=4.7 Hz, 3H), 0.96 (m, 1H). ESI-MS (M+H$^+$): m/z calculated 744.3, founded 744.3.

Example 54

Synthesis of Compound 12r

Compound 12d (0.18 mmol) was dissolved in 20 mL HCl-Et$_2$O (2N) and stirred at 30° C. until completed to obtain de-Boc product, followed by reacting with another reagent iPrOC(O)Cl (1.2 eq) to obtain the product 12r. yield: 76%.

$^1$H-NMR for the product 12r (CDCl$_3$, 500 MHz): δ 10.35 (s, 1H), 7.26 (s, 1H), 6.68 (s, 1H), 6.57 (s, 1H), 5.92 (s, 2H), 5.67 (q, J=8.1 Hz, 1H), 5.42 (s, 1H), 4.95 (t, J=8.1 Hz, 1H), 4.58 (m, 5H), 4.29 (m, 2H), 3.81 (m, 1H), 2.86 (m, 1H), 2.42 (br, 3H), 2.24 (m, 1H), 1.77 (m, 4H), 1.58-1.25 (m, 18H), 1.07 (m, 2H), 0.90 (m, 1H). ESI-MS (M+H$^+$): m/z calculated 770.3, founded 770.4.

Example 55

Synthesis of Compound 12s

The synthetic procedure is the same as in Examples 48-50 starting 10f with in 0.3 mmol scale. Finally, 32 mg of product 12s was obtained, and confirmed by ESI-MS (M+H$^+$): m/z calculated 770.3, founded 770.4.

Example 56

Synthesis of Compound 12t

The synthetic procedure is the same as in Examples 48-50 starting 10f with in 0.3 mmol scale. Finally, 41 mg of product 12s was obtained, and confirmed by ESI-MS (M+H$^+$): m/z calculated 770.3, founded 770.4.

Example 57

Synthesis of Compound 12u

The synthetic procedure is the same as in Examples 48-50 starting 10-Ref with in 0.3 mmol scale. Finally, 52 mg of product 12u was obtained, and confirmed by ESI-MS (M+H$^+$): m/z calculated 810.3, founded 810.4.

Example 58

Synthesis of Compound 12-Ref

Compound 11-Ref (0.18 mmol) was dissolved in 10 mL anhydrous dichloromethane, EDCI (69.8 mg, 0.36 mmol, 2 eq.) was added and stirred at room temperature overnight until completed. The reaction mixture was worked out and concentrated.

The obtained solid was dissolved in 10 mL of anhydrous dichloromethane, DBU (61.0 mg, 0.40 mmol) and RSO$_2$NH$_2$ (0.363 mmol, R=cyclopropyl) were added and stirred at room temperature overnight until completed. The reaction mixture was worked out and purified by flash column to obtain the product 12-Ref (62 mg; Yield: 53%).

$^1$H-NMR for the product 12-Ref (CDCl3, 500 MHz): δ 10.28-10.29 (d, 1H), 6.87-7.07 (m, 3H), 5.72-5.74 (m, 1H), 5.48 (br, 1H), 4.99-5.03 (m, 2H), 4.58-4.79 (m, 5H), 4.42 (m, 1H), 4.21 (m, 1H), 3.83-3.85 (m, 1H), 2.90-2.93 (m, 1H), 2.48-2.57 (m, 3H), 2.27-2.30 (m, 1H), 1.88-1.97 (m, 2H), 1.67-1.79 (m, 2H), 1.45-1.58 (m, 6H), 1.34-1.40 (m, 2H), 1.27 (s, 4H), 1.24 (s, 5H), 1.08-1.15 (m, 2H), 0.91-0.94 (m, 1H).
ESI-MS (M+H$^+$): m/z calculated 732.3, founded 732.5.

Example 59

Synthesis of Compound 15a

Compound 12d (3.0 mmol) was dissolved in 30 mL HCl-Et2O (4N) to remove Boc group, followed by adding phenyl borate and Cu(AcO)2 (2 eq/each.) in DCE (30 mL) to obtain the product 15a (Yield: 62%). ESI-MS (M+H$^+$): m/z calculated 734.3, founded 734.4.

Example 60

Synthesis of Compound 15b

Compound 12d (3.0 mmol) was dissolved in 30 mL HCl-Et2O (4N) to remove Boc group, followed by adding m-fluorophenyl borate and Cu(AcO)2 (2 eq/each.) in DCE (30 mL) to obtain the product 15b (Yield: 53%). ESI-MS (M+H$^+$): m/z calculated 752.3, founded 752.3.

Example 61

Synthesis of Compound 16a

Compound 12d (3.0 mmol) was dissolved in 30 mL HCl-Et2O (4N) to remove Boc group, followed by adding p-chlorophenylsulfonyl chloride (1.3 eq) in DCE (30 mL) to obtain the product 16a (Yield: 81%). ESI-MS (M+H$^+$): m/z calculated 832.2, founded 832.2.

Example 62

Synthesis of Compound 16b

Compound 12d (3.0 mmol) was dissolved in 30 mL HCl-Et2O (4N) to remove Boc group, followed by adding phenylsulfonyl chloride (1.3 eq)) in DCE (30 mL) to obtain the product 16b (Yield: 74%). ESI-MS (M+H$^+$): m/z calculated 798.2, founded 798.3.

Example 63

Synthesis of Compound 16c

Compound 12d (3.0 mmol) was dissolved in 30 mL HCl-Et2O (4N) to remove Boc group, followed by adding p-methoxyphenylsulfonyl chloride (1.3 eq) in DCE (30 mL) to obtain the product 16c (Yield: 79%). ESI-MS (M+H$^+$): m/z calculated: 828.2, founded: 828.3.

Example 64

Synthesis of Compound 17

SM-11 (35 g), DMF (350 mL) were added to a flask, followed by adding SM-12 (17 g) and HATU (10.4 g) into the reaction mixture in ice-water bath. After stirred for 10 minutes, DIEA (125 mL) was added, the mixture was allowed to room temperature. The mixture was stirred overnight and concentrated under reduced pressure. The reaction mixture was worked out and purified by flash column to obtain the foamy solid product 17 (18.6 g). Confirmed by ESI-MS (M+H$^+$): m/z calculated 407.3, founded 407.5.

Example 65

Synthesis of Compound 21a

The synthetic procedure starting with intermediate 17 is the same as in Examples 16-47 for preparation of 12a-12h in 1.0 mmol scale to prepare 21a. After purification, 59 mg of product 21a was obtained. Confirmed by ESI-MS (M+H$^+$): m/z calculated 669.3, founded 669.4.

Example 66

Synthesis of Compound 21b

The synthetic procedure starting with intermediate 17 is the same as in Examples 16-47 for preparation of 12a-12h in

Example 67

Synthesis of Compound 21c

The synthetic procedure starting with intermediate 17 is the same as in Examples 16-47 for preparation of 12a-12h in 1.0 mmol scale to prepare 21c. After purification, 49 mg of product 21c was obtained. Confirmed by ESI-MS (M+H$^+$): m/z calculated 643.3, founded 643.4.

Example 68

Synthesis of Compound 21d

The synthetic procedure starting with intermediate 17 is the same as in Examples 16-47 for preparation of 12a-12h in 1.0 mmol scale to prepare 21d. After purification, 63 mg of product 21d was obtained. Confirmed by ESI-MS (M+H$^+$): m/z calculated 683.3, founded 683.4.

Example 69

Synthesis of Compound 21e

The synthetic procedure starting with intermediate 17 is the same as in Examples 16-47 for preparation of 12a-12h in 1.0 mmol scale to prepare 21e. After purification, 63 mg of product 21e was obtained.

$^1$H-NMR for the product 21e (CDCl$_3$, 500 MHz): δ 10.60 (s, 1H), 7.10 (s, 1H), 6.61-6.74 (m, 3H), 5.95 (s, 2H), 5.65-5.69 (m, 1H), 5.26-5.29 (m, 1H), 4.98-5.09 (m, 1H), 4.65-4.68 (m, 1H), 4.41-4.56 (m, 4H), 3.88-3.91 (m, 1H), 3.47-3.53 (m, 2H), 3.19-3.26 (m, 1H), 3.07 (s, 1H), 2.96-3.01 (m, 1H), 2.90 (s, 3H), 2.50-2.64 (m, 1H), 2.24-2.28 (m, 1H), 2.04-2.16 (m, 3H), 1.67-1.99 (m, 4H), 1.08-1.49 (m, 8H), 0.86-0.96 (m, 2H). ESI-MS (M+H$^+$): m/z calculated 657.3, founded 657.4

Example 70

Synthesis of Compound 21f

The synthetic procedure starting with intermediate 17 is the same as in Examples 16-47 for preparation of 12a-12h in 1.0 mmol scale to prepare 21f. After purification, 63 mg of product 21f was obtained. Confirmed by ESI-MS (M+H$^+$): m/z calculated 669.3, founded 669.5.

Example 71

Synthesis of Compound 27a

The synthetic procedure starting with SM-7 in 5.0 mmol scale is the same as in Examples 7-47 for preparation of 12a-12h to prepare 27a. After purification, 69 mg of product 27a was obtained.

$^1$H-NMR for the product 27a (CDCl$_3$, 500 MHz): δ 6.71 (s, 1H), 6.66 (s, 1H), 5.97-5.98 (s, 2H), 5.70-5.73 (m, 1H), 5.31-5.37 (m, 1H), 5.13-5.17 (m, 1H), 4.83-4.86 (m, 1H), 4.51-4.62 (m, 4H), 3.80-3.83 (m, 1H), 3.78-3.79 (m, 1H), 3.52-3.54 (m, 1H), 3.06-3.09 (m, 1H), 2.90 (s, 3H), 2.48-2.49 (m, 1H), 2.23-2.35 (m, 2H), 2.00-2.08 (m, 4H), 1.63-1.72 (m, 2H), 1.38-1.51 (m, 8H), 1.80-1.82 (m, 3H). ESI-MS (M+H$^+$): m/z calculated 658.3, founded 658.4.

Example 72

Synthesis of Compound 27b

The synthetic procedure starting with SM-7 in 5.0 mmol scale is the same as in Examples 7-47 for preparation of 12a-12h to prepare 27b. After purification, 83 mg of product 27b was obtained.

$^1$H-NMR for the product 27b (CDCl$_3$, 500 MHz): δ 6.72-6.76 (m, 2H), 5.71-5.72 (m, 1H), 5.36-5.37 (m, 1H), 5.15-5.17 (m, 1H), 4.84-4.85 (m, 1H), 4.53-4.61 (m, 4H), 4.25 (s, 4H), 3.79-3.82 (m, 2H), 3.51-3.53 (m, 1H), 2.93-3.04 (m, 2H), 2.89 (s, 3H), 2.48-2.49 (m, 1H), 2.24-2.35 (m, 2H), 1.93-2.03 (m, 3H), 1.69-1.73 (m, 1H), 1.49-1.51 (m, 2H), 1.27-1.38 (m, 3H), 1.06-1.14 (m, 2H), 0.80-0.88 (m, 3H). ESI-MS (M+H$^+$): m/z calculated 672.3, founded 672.4.

Example 73

Synthesis of Compound 27c

The synthetic procedure starting with SM-7 in 5.0 mmol scale is the same as in Examples 7-47 for preparation of 12a-12h to prepare 27c. After purification, 57 mg of product 27c was obtained. Confirmed by ESI-MS (M+H$^+$): m/z calculated 630.3, founded 630.5

Example 74

Synthesis of Compound 27-Ref

The synthetic procedure starting with SM-7 in 5.0 mmol scale is the same as in Examples 7-47 for preparation of 12a-12h to prepare 27-Ref. After purification, 89 mg of product 27-Ref was obtained.

$^1$H-NMR for the product 21e (CDCl$_3$, 500 MHz): δ 7.41-7.43 (m, 1H), 6.96-7.07 (m, 2H), 5.71-5.73 (m, 1H), 5.38-5.39 (m, 1H), 5.13-5.18 (m, 1H), 4.84-4.88 (m, 1H), 4.73-4.77 (m, 2H), 4.67-4.70 (m, 2H), 3.80-3.84 (m, 1H), 3.65-3.68 (m, 1H), 3.52-3.56 (m, 1H), 3.06-3.09 (m, 1H), 2.93-2.96 (m, 1H), 2.89 (s, 3H), 2.49-2.52 (m, 2H), 2.24-2.36 (m, 2H), 2.00-2.10 (m, 2H), 1.68-1.69 (m, 2H), 1.48-1.51 (m, 2H), 1.27-1.38 (m, 5H), 1.07-1.31 (m, 2H). ESI-MS (M+H$^+$): m/z calculated 632.3, founded 632.4.

Example 75

Synthesis of Compound 27-Ref-2

The synthetic procedure starting with SM-7 in 5.0 mmol scale is the same as in Examples 7-47 for preparation of 12a-12h to prepare 27-Ref-2. After purification, 61 mg of product 27-Ref-2 was obtained. Confirmed by ESI-MS (M+H$^+$): m/z calculated 658.3, founded 658.4.

Example 76

Synthesis of Compound 30a

Chemical SM-13a (5.4 g, 10 mmol), sulfonamide (SM-8a, 1.1 eq) and DMF (80 mL) were added into 250 mL flask reactor, followed by adding coupling reagent EDCI (1.3 eq) to keep the amidation at 55° C. until completed. The reaction mixture was worked out to obtain crude product 28a, followed by removing Boc group with HCl-THF solution to obtain 29a (3.7 g, yield: 83%), which was purified by precipitation in hexane-EtOAc and dried directly for next step. ESI-MS (M+H$^+$): m/z calculated 533.2, founded 533.2.

In the presence of coupling reagent HATU (1.3 eq) in DMF (1.0 mL), compound 29a (60 mg, 0.1 mmol) was reacted with another acid derivative SM-14a to obtain product 30a. After purification by flash column, 39 mg of 30a was obtained.

$^1$H-NMR for the product 30a (CDCl$_3$, 500 MHz): δ 9.98 (s, 1H), 9.39 (m, 1H), 8.77 (m, 1H), 8.56 (m, 1H), 8.19 (d, J=9.0 Hz, 1H), 7.32 (s, 1H), 6.89 (m, 1H), 6.71 (s, 1H), 6.67 (s, 1H), 5.95-5.96 (d, J=5.1 Hz, 2H), 5.72-5.81 (m, 1H), 5.26-5.30 (m, 1H), 5.13-5.16 (m, 1H), 5.40 (s, 1H), 4.63-4.70 (m, 2H), 4.52-4.60 (m, 3H), 4.43-4.48 (m, 2H), 4.20-4.22 (d, J=1.8 Hz, 1H), 3.88-3.91 (m, 1H), 2.81-2.86 (m, 1H), 2.35-2.38 (m, 1H), 2.06-2.13 (m, 1H), 2.04 (s, 1H), 1.95 (m, 2H), 1.87 (m, 1H), 1.61-1.73 (m, 6H), 1.46-1.50 (m, 1H), 1.24-1.31 (m, 4H), 0.99-1.06 (m, 12H). ESI-MS [(M+H)$^+$]: m/z calculated 891.4, founded 891.5

Example 77

Synthesis of Compound 30b

The synthetic procedure was carried out as the same as in Example 76 for preparation of compound 30b. After purification, 46 mg of product 30b was obtained.

$^1$H-NMR for the product 30b (CDCl$_3$, 500 MHz): δ 9.99 (s, 1H), 9.39 (m, 1H), 8.76 (m, 1H), 8.55 (m, 1H), 8.19 (d, J=9.0 Hz, 1H), 7.24 (s, 1H), 6.87-6.89 (d, J=8.6 Hz, 1H), 6.72 (s, 1H), 6.67 (s, 1H), 5.95-5.96 (d, J=5.1 Hz, 2H), 5.40 (s, 1H), 4.64-4.70 (m, 2H), 4.53-4.59 (m, 3H), 4.44-4.49 (m, 2H), 4.18-4.20 (d, J=1.8 Hz, 1H), 3.86-3.89 (m, 1H), 2.96 (s, 1H), 2.88 (m, 1H), 2.04 (s, 1H), 1.95 (m, 2H), 1.85 (m, 1H), 1.53-1.73 (m, 9H), 1.17-1.35 (m, 6H), 0.96-1.03 (m, 12H). ESI-MS [(M+H)$^+$]: m/z calculated 893.4, founded 893.4

Example 78

Synthesis of Compound 30c

The synthetic procedure was carried out as the same as in Example 76 for preparation of compound 30c. After purification, 41 mg of product 30c was obtained.

$^1$H-NMR for the product 30c (CDCl$_3$, 500 MHz): δ 10.37 (s, 1H), 9.26 (m, 1H), 8.74 (m, 1H), 8.57 (m, 1H), 8.34-8.36 (m, 1H), 7.31-7.32 (m, 1H), 6.76 (m, 1H), 6.79 (m, 1H), 5.92 (m, 1H), 5.39 (s, 1H), 5.30-5.33 (m, 1H), 5.13-5.15 (m, 2H), 4.72-4.74 (m, 1H), 4.61 (m, 2H), 4.49 (m, 2H), 4.40-4.43 (m, 2H), 4.25 (m, 4H), 2.87 (m, 1H), 2.47 (m, 1H), 2.25 (m, 2H), 1.89 (m, 4H), 1.78-1.80 (m, 4H), 1.65-1.67 (m, 1H), 1.44-1.48 (m, 2H), 1.13-1.21 (m, 8H), 1.02 (s, 9H). ESI-MS [(M+H)$^+$]: m/z calculated 905.4, founded 905.4

Example 79

Synthesis of Compound 30d

The synthetic procedure was carried out as the same as in Example 76 for preparation of compound 30d. After purification, 38 mg of product 30d was obtained.

$^1$H-NMR for the product 30d (CDCl$_3$, 500 MHz): δ10.38 (s, 1H), 9.27 (s, 1H), 8.74 (m, 1H), 8.57 (m, 1H), 8.34-8.36 (m, 1H), 7.30-7.32 (m, 1H), 6.82 (m, 1H), 6.64-6.71 (m, 1H), 5.90 (m, 1H), 5.39 (s, 1H), 5.30-5.32 (m, 1H), 5.13-5.15 (m, 2H), 4.73-4.75 (m, 1H), 4.64 (m, 2H), 4.46-4.52 (m, 2H), 4.37-4.39 (m, 2H), 4.27-4.29 (m, 4H), 2.88 (m, 1H), 2.46 (m, 1H), 2.23 (m, 2H), 1.87-1.90 (m, 6H), 1.78-1.80 (m, 4H), 1.65-1.67 (m, 1H), 1.43-1.49 (m, 2H), 1.14-1.231 (m, 6H), 1.03 (s, 9H). ESI-MS [(M+H)$^+$]: m/z calculated 905.4, founded 905.4.

Example 80

Synthesis of Compound 30e

The synthetic procedure was carried out as the same as in Example 76 for preparation of compound 30e. After purification, 43 mg of product 30e was obtained.

$^1$H-NMR for the product 30e (CDCl$_3$, 500 MHz): δ10.39 (s, 1H), 9.27 (s, 1H), 8.74 (m, 1H), 8.57 (m, 1H), 8.38 (m, 1H), 7.30-7.32 (m, 1H), 6.78 (m, 1H), 6.69-6.74 (m, 1H), 5.99 (s, 2H), 5.87-5.95 (m, 1H), 5.40 (s, 1H), 5.31-5.34 (m, 1H), 5.12-5.14 (m, 2H), 4.73-4.76 (m, 1H), 4.65-4.66 (m, 2H), 4.47-4.58 (m, 3H), 4.37-4.42 (m, 1H), 2.88 (m, 1H), 2.47 (m, 1H), 2.24 (m, 2H), 1.89 (m, 3H), 1.78-1.80 (m, 4H), 1.65-1.67 (m, 1H), 1.42-1.47 (m, 2H), 1.14-1.23 (m, 6H), 1.03 (s, 9H), 0.84-0.88 (m, 3H), ESI-MS [(M+H)$^+$]: m/z calculated 891.4, founded 891.4

Example 81

Synthesis of Compound 30f

The synthetic procedure was carried out as the same as in Example 76 for preparation of compound 30f. After purification, 43 mg of product 30f was obtained.

$^1$H-NMR for the product 30f (CDCl$_3$, 500 MHz): δ9.97-9.99 (m, 1H), 9.40 (s, 1H), 8.76 (m, 1H), 8.55 (m, 1H), 8.19 (m, 1H), 7.32-7.35 (m, 1H), 7.00 (m, 1H), 6.65-6.77 (m, 2H), 5.92-5.97 (m, 2H), 5.41 (s, 1H), 4.47-4.76 (m, 7H), 4.21-4.26 (m, 1H), 3.88-3.90 (m, 1H), 2.84-2.91 (m, 1H), 2.33-2.40 (m, 2H), 2.21 (m, 3H), 1.83 (m, 1H), 1.55-1.65 (m, 9H), 1.12-1.42 (m, 6H), 0.96-1.03 (m, 13H). ESI-MS [(M+H)$^+$]: m/z calculated 893.4, founded 893.5

Example 82

Synthesis of Compound 30g

The synthetic procedure was carried out as the same as in Example 76 for preparation of compound 30g. After purification, 26 mg of product 30g was obtained. Confirmed by ESI-MS [(M+H)$^+$]: m/z calculated 919.4, founded 919.4.

Example 83

Synthesis of Compound 30h

The synthetic procedure was carried out as the same as in Example 76 for preparation of compound 30h. After purification, 43 mg of product 30h was obtained.

$^1$H-NMR for the product 30h (CDCl$_3$, 500 MHz): δ9.99 (s, 1H), 9.38 (m, 1H), 8.76 (m, 1H), 8.56 (m, 1H), 8.15-8.17 (m, 1H), 7.10 (s, 1H), 6.89 (s, 1H), 6.84 (s, 1H), 6.73-6.75 (m, 2H), 5.40 (s, 1H), 4.62-4.72 (m, 2H), 4.52-4.60 (m, 3H), 4.41-4.46 (m, 2H), 4.16-4.21 (m, 5H), 3.85-3.88 (m, 1H), 2.84-2.91 (m, 1H), 2.36-2.45 (m, 1H), 2.32-2.36 (m, 1H), 2.16-2.21 (m, 2H), 1.87 (m, 1H), 1.72-1.75 (m, 6H), 1.65-1.68 (m, 3H), 1.57-1.59 (m, 2H), 1.49-1.5 (m, 2H), 1.31-1.33 (m, 2H), 1.27 (m, 1H), 1.21-1.23 (m, 2H), 1.08-1.09 (m, 3H), 1.01 (s, 9H), 0.97-0.99 (m, 3H). ESI-MS [(M+H)$^+$]: m/z calculated 921.4, founded 921.4.

Example 84

Synthesis of Compound 30j

The synthetic procedure was carried out as the same as in Example 76 for preparation of compound 30j. After purification, 43 mg of product 30j was obtained.

$^1$H-NMR for the product 30j (CDCl$_3$, 500 MHz): δ 9.98-10.02 (m, 1H), 9.40-9.41 (m, 1H), 8.75 (m, 1H), 8.52-8.55 (m, 1H), 8.18-8.21 (m, 1H), 7.09 (s, 1H), 6.89-6.92 (m, 1H), 6.79-6.81 (d, J=8.0 Hz, 1H), 6.74-6.75 (d, J=8.0 Hz, 1H), 5.42 (s, 1H), 4.67-4.76 (m, 2H), 4.54-4.61 (m, 3H), 4.42-4.49 (m, 2H), 4.24-4.26 (t, J=5.5Hz, 2H), 4.16-4.20 (m, 3H), 3.87-3.93 (m, 1H), 2.84-2.91 (m, 1H), 2.40-2.46 (m, 1H), 2.30-2.36 (m, 1H), 2.18-2.23 (m, 2H), 1.88 (m, 1H), 1.80 (m, 3H), 1.63-1.71 (m, 5H), 1.57-1.61 (m, 3H), 1.36-1.41 (m, 1H), 1.30 (m, 2H), 1.18-1.26 (m, 2H), 1.08-1.10 (m, 2H), 1.02-1.04 (m, 2H), 0.99 (s, 9H), 0.96-0.98 (m, 3H). ESI-MS [(M+H)$^+$]: m/z calculated 921.4, founded 921.4.

Example 85

Synthesis of Compound 30k

The synthetic procedure was carried out as the same as in Example 76 for preparation of compound 30k. After purification, 42 mg of product 30k was obtained.

$^1$H-NMR for the product 30k (CDCl$_3$, 500 MHz): δ10.36 (s, 1H), 9.27 (m, 1H), 8.74 (m, 1H), 8.57 (m, 1H), 8.34-8.37 (m, 1H), 7.30 (m, 1H), 7.08 (m, 1H), 6.98 (m, 2H), 5.92 (m, 1H), 5.41 (s, 1H), 5.30-5.33 (m, 1H), 5.13-5.15 (m, 2H), 4.75 (m, 3H), 4.65-4.68 (m, 1H), 4.59 (m, 1H), 4.47-4.51 (m, 1H), 4.38-4.42 (m, 1H), 2.87 (m, 1H), 2.49 (m, 1H), 2.37 (m, 1H), 2.23-2.26 (m, 1H), 1.89 (m, 1H), 1.79 (m, 4H), 1.67 (m, 2H), 1.42-1.45 (m, 2H), 1.26-1.31 (m, 4H), 1.14-1.19 (m, 4H), 1.01-1.06 (m, 12H). ESI-MS [(M+H)$^+$]: m/z calculated 865.4, founded 865.6.

Example 86

Synthesis of Compound 30m

The synthetic procedure was carried out as the same as in Example 76 for preparation of compound 30m. After purification, 43 mg of product 30m was obtained.

$^1$H-NMR for the product 30m (CDCl$_3$, 500 MHz): δ 10.02 (m, 1H), 7.20 (s, 1H), 6.71 (s, 1H), 6.64 (m, 2H), 5.95-5.97 (m, 2H), 5.38 (s, 1A), 4.82-4.83 (m, 1H), 4.62-4.69 (m, 2H), 4.45-4.51 (m, 4H), 4.17-4.20 (m, 1H), 3.83-3.85 (m, 2H), 2.93 (m, 1H), 2.48 (m, 1H), 2.29 (m, 1H), 1.89 (m, 1H), 1.63-1.72 (m, 5H), 1.53-1.60 (m, 5H), 1.49 (s, 9H), 1.34-1.37 (m, 3H), 1.16-1.21 (m, 2H), 1.04-1.06 (m, 4H), 1.00 (s, 9H), 0.97-0.99 (m, 3H). ESI-MS [(M+H)$^+$]: m/z calculated 887.4, founded 887.4.

Example 87

Synthesis of Compound 30n

The synthetic procedure was carried out as the same as in Example 76 for preparation of compound 30n. After purification, 43 mg of product 30n was obtained.

$^1$H-NMR for the product 30n (CDCl$_3$, 500 MHz): δ 10.10 (s, 1H), 7.39 (s, 1H), 6.94 (m, 1H), 6.68 (s, 1H), 6.61 (m, 1H), 5.96 (s, 2H), 5.42 (s, 1H), 5.25 (br, 1H), 4.52-4.64 (m, 4H), 4.42-4.49 (m, 2H), 4.17-4.19 (m, 1H), 3.88-3.89 (m, 1H), 3.65 (m, 1H), 2.94 (m, 1H), 2.90 (s, 1H), 2.36-2.41 (m, 2H), 1.93 (m, 1H), 1.73 (m, 3H), 1.58-1.64 (m, 6H), 1.35 (m, 2H), 1.19-1.26 (m, 5H), 1.03-1.06 (m, 3H), 1.03 (s, 9H), 0.98-0.99 (m, 3H). ESI-MS [(M+H)$^+$]: m/z calculated 865.3, founded 865.4

Example 88

Synthesis of Compound 30p

The synthetic procedure was carried out as the same as in Example 76 for preparation of compound 30p. After purification, 33 mg of product 30p was obtained.

$^1$H-NMR for the product 30p (CDCl$_3$, 500 MHz): δ 10.24 (s, 1H), 8.65 (m, 1H), 8.08 (m, 1H), 8.01 (m, 1H), 7.9 (m, 1H), 7.67 (m, 1H), 7.58 (m, 1H), 7.48 (m, 1H), 7.40 (m, 1H), 6.68 (m, 1H), 6.62 (s, 1H), 6.44 (s, 1H), 5.86-5.91 (m, 2H), 5.63 (s, 1H), 5.40 (s, 1H), 4.44-4.62 (m, 4H), 4.37-4.40 (m, 2H), 3.99-4.01 (m, 1H), 3.83 (m, 1H), 3.26 (m, 1H), 2.96 (m, 1H), 2.46 (m, 1H), 2.35 (m, 1H), 1.86 (m, 1H), 1.56-1.65 (m, 4H), 1.46-1.48 (m, 4H), 1.39-1.42 (m, 4H), 1.09 (m, 3H), 0.99-1.02 (m, 4H), 0.84 (s, 9H), 0.72 (m, 3H). ESI-MS [(M+H)$^+$]: m/z calculated 977.4, founded 977.4.

Synthesis of Compound 30q

The synthetic procedure was carried out as the same as in Example 76 for preparation of compound 30q. After purification, 39 mg of product 30q was obtained. Confirmed by ESI-MS [(M+H)$^+$]: m/z calculated 891.4, founded 891.5.

Example 90

Synthesis of Compound 30r

The synthetic procedure was carried out as the same as in Example 76 for preparation of compound 30r. After purification, 44 mg of product 30r was obtained.

$^1$H-NMR for the product 30r (CDCl$_3$, 500 MHz): δ 10.51 (s, 1H), 7.65-7.67 (d, J=7.4 Hz, 2H), 7.47-7.51 (m, 2H), 7.34-7.37 (t, J=7.8 Hz, 2H), 6.98-6.99 (m, 1H), 6.54 (s, 1H), 6.30 (s, 1H), 5.87 (s, 1H), 5.81 (s, 2H), 5.45 (s, 1H), 4.55-4.63 (m, 3H), 4.46-4.49 (m, 1H), 4.19-4.26 (m, 2H), 4.05-4.07 (m, 1H), 3.85-3.87 (m, 1H), 3.18 (m, 1H), 2.96 (m, 1H), 2.68 (m, 1H), 2.42 (m, 1H), 1.84 (m, 1H), 1.65-1.67 (m, 2H), 1.51-1.55 (m, 9H), 1.25-1.37 (m, 5H), 1.08-1.13 (m, 5H), 0.99 (s, 9H), 0.85 (m, 3H). ESI-MS [(M+H)$^+$]: m/z calculated 927.4, founded 927.4.

Example 91

Synthesis of Compound 30s

The synthetic procedure was carried out as the same as in Example 76 for preparation of compound 30s. After purification, 37 mg of product 30s was obtained.

$^1$H-NMR for the product 30s (CDCl$_3$, 500 MHz): δ 10.52 (s, 1H), 8.10 (m, 1H), 7.84-7.88 (t, J=9.0 Hz, 2H), 7.76-7.78 (m, 1H), 7.66-7.67 (m, 1H), 7.59-7.62 (m, 1H), 7.51-7.54 (m, 1H), 6.98 (m, 1H), 6.49 (s, 1H), 6.24 (s, 1H), 5.88-5.91 (m, 2H), 5.72 (s, 1H), 5.49 (s, 1H), 5.41 (s, 1H), 4.59-4.66 (m, 3H), 4.49-4.51 (m, 1H), 4.19-4.24 (m, 2H), 4.03-4.05 (m, 1H), 3.85-3.87 (m, 1H), 3.25 (m, 1H), 2.98 (m, 1H), 2.68 (m, 1H), 2.45 (m, 1H), 1.87 (m, 1H), 1.64-1.66 (m, 2H), 1.50-1.59 (m, 8H), 1.30-1.36 (m, 4H), 0.99-1.05 (m, 5H), 0.94 (s, 9H), 0.88 (m, 3H). ESI-MS [(M+H)$^+$]: m/z calculated 977.4, founded 977.4

Example 92

Synthesis of Compound 30t

The synthetic procedure was carried out as the same as in Example 76 for preparation of compound 30t. After purification, 21 mg of product 30t was obtained.

$^1$H-NMR for the product 30t (CDCl$_3$, 500 MHz): δ 10.05 (m, 1H), 7.32 (s, 1H), 6.71 (m, 1H), 6.63 (m, 1H), 6.59 (m, 1H), 5.96 (m, 2H), 5.39 (s, 1H), 4.91 (m, 1H), 4.43-4.66 (m, 7H), 4.19 (m, 1H), 3.87-3.95 (m, 1H), 3.68-3.77 (m, 1H), 2.93 (m, 1H), 2.49 (m, 1H), 2.33 (m, 1H), 1.96 (s, 1H), 1.81 (m, 1H), 1.71 (m, 3H), 1.57-1.63 (m, 6H), 1.36 (m, 3H), 1.25 (s, 3H), 1.15 (s, 2H), 1.11 (s, 3H), 0.99-1.04 (m, 18H). ESI-MS [(M+H)$^+$]: m/z calculated 899.4, founded 899.4

Example 93

Synthesis of Compound 30v

The synthetic procedure was carried out as the same as in Example 76 for preparation of compound 30v. After purification, 45 mg of product 30v was obtained.

$^1$H-NMR for the product 30v (CDCl$_3$, 500 MHz): δ 10.04 (s, 1H), 7.23 (s, 1H), 6.72 (s, 1H), 6.64 (m, 2H), 5.96-5.97 (m, 2H), 5.38 (s, 1H), 4.97-4.98 (m, 1H), 4.59-4.69 (m, 2H), 4.47-4.52 (m, 4H), 4.18-4.20 (m, 1H), 3.94 (m, 1H), 3.84 (m, 1H), 2.94 (m, 1H), 2.47 (m, 1H), 2.33 (m, 1H), 1.87 (m, 1H), 1.66-1.69 (m, 5H), 1.56-1.58 (m, 5H), 1.36 (m, 3H), 1.22-1.27 (m, 3H), 1.17-1.19 (m, 2H), 1.14-1.16 (m, 2H), 1.03-1.08 (m, 4H), 1.00 (s, 9H), 0.97-0.98 (m, 3H). ESI-MS [(M+H)$^+$]: m/z calculated 859.4, founded 859.4

Example 94

Synthesis of Compound 30w

The synthetic procedure was carried out as the same as in Example 76 for preparation of compound 30w. After purification, 40 mg of product 30w was obtained.

$^1$H-NMR for the product 30w (CDCl$_3$, 500 MHz): δ 10.02 (m, 1H), 7.19 (s, 1H), 6.72 (s, 1H), 6.65 (m, 2H), 5.96-5.97 (m, 2H), 5.38 (s, 1H), 4.89 (m, 2H), 4.60-4.69 (m, 2H), 4.47-4.51 (m, 4H), 4.20-4.22 (m, 1H), 3.83-3.90 (m, 2H), 2.94 (m, 1H), 2.48 (m, 1H), 2.33 (m, 1H), 1.88 (m, 1H), 1.64-1.69 (m, 5H), 1.56-1.58 (m, 5H), 1.36-1.37 (m, 3H), 1.25 (s, 3H), 1.24 (s, 3H), 1.14-1.19 (m, 3H), 0.97-1.05 (m, 12H), 0.82-0.91 (m, 3H). ESI-MS [(M+H)$^+$]: m/z calculated 873.4, founded 873.5

Example 95

Synthesis of Compound 30x

The synthetic procedure was carried out as the same as in Example 76 for preparation of compound 30x. After purification, 41 mg of product 30x was obtained.

$^1$H-NMR for the product 30x (CDCl$_3$, 500 MHz): δ 10.09 (s, 1H), 7.34 (br, 1H), 6.71 (s, 1H), 6.65 (m, 2H), 5.96-5.97 (m, 2H), 5.38 (s, 1H), 5.05 (m, 1H), 4.59-4.689 (m, 2H), 4.49-4.52 (m, 4H), 4.17-4.19 (m, 1H), 3.96 (m, 1H), 3.88 (m, 1H), 3.68 (s, 3H), 2.92 (m, 1H), 2.43 (m, 1H), 2.34 (m, 1H), 1.88 (m, 1H), 1.64-1.69 (m, 5H), 1.56-1.57 (m, 5H), 1.35 (m, 3H), 1.26 (m, 4H), 1.17-1.20 (m, 2H), 1.01 (s, 9H), 0.88-0.89 (m, 3H). ESI-MS [(M+H)$^+$]: m/z calculated 845.4, founded 845.4

Example 96

Synthesis of Compound 30y

The synthetic procedure was carried out as the same as in Example 76 for preparation of compound 30y. After purification, 43 mg of product 30y was obtained. Confirmed by ESI-MS [(M+H)$^+$]: m/z calculated 921.4, founded 921.4

Example 97

Synthesis of Compound 30z

The synthetic procedure was carried out as the same as in Example 76 for preparation of compound 30z. After purification, 31 mg of product 30z was obtained. Confirmed by ESI-MS [(M+H)$^+$]: m/z calculated 907.4, founded 907.5.

Example 98

Synthesis of Compound 30aa

The synthetic procedure was carried out as the same as in Example 76 for preparation of compound 30aa. After purification, 31 mg of product 30aa was obtained.

$^1$H-NMR for the product 30aa (CDCl$_3$, 500 MHz): δ 10.00 (s, 1H), 7.76-7.78 (d, J=7.3 Hz, 2H), 7.58-7.62 (d, J=7.4 Hz, 2H), 7.38-7.42 (m, 2H), 7.30-7.34 (m, 2H), 7.03 (s, 1H), 6.69 (m, 2H), 6.65 (s, 1H), 5.93-5.96 (m, 2H), 5.38 (s, 1H), 5.13-5.15 (m, 1H), 4.59-4.69 (m, 2H), 4.52 (s, 2H), 4.39-4.48 (m, 4H), 4.17-4.20 (m, 1H), 3.95 (m, 1H), 3.83-3.87 (m, 1H), 2.91 (m, 1H), 2.43 (m, 1H), 2.30 (m, 1H), 1.86 (s, 1H), 1.68-1.73 (m, 2H), 1.61-1.64 (m, 3H), 1.53-1.58 (m, 3H), 1.33-1.36 (m, 2H), 1.26-1.30 (m, 2H), 1.15-1.20 (m, 3H), 0.97-1.03 (m, 15H). ESI-MS [(M+H)$^+$]: m/z calculated 1009.4, founded 1009.4

Example 99

Synthesis of Compound 30ab

The synthetic procedure was carried out as the same as in Example 76 for preparation of compound 30ab. After purification, 46 mg of product 30ab was obtained.

$^1$H-NMR for the product 30ab (CDCl$_3$, 500 MHz): δ 10.49 (brs, 1H), 7.40 (brs, 1H), 6.68 (s, 1H), 6.64 (m, 2H), 5.92-5.95 (m, 2H), 5.81 (brs, 1H), 5.43 (m, 1H), 5.28-5.30 (m, 1H), 5.11-5.19 (m, 1H), 4.87 (m, 1H), 4.55-4.64 (m, 3H), 4.25-4.51 (m, 3H), 4.19 (m, 1H), 3.92-4.04 (m, 2H), 2.83 (m, 1H), 2.28-2.39 (m, 2H), 2.20 (m, 1H), 1.98 (m, 1H), 1.67-1.81 (m, 3H), 1.41-1.62 (m, 5H), 1.30 (s, 9H), 1.12-1.26 (m, 3H), 1.07-1.09 (m, 3H), 1.03 (s, 9H), 0.86-0.99 (m, 3H). ESI-MS [(M+H)$^+$]: m/z calculated 884.4, founded 884.5

Example 100

Synthesis of Compound 30ac

The synthetic procedure was carried out as the same as in Example 76 for preparation of compound 30ac. After purification, 42 mg of product 30ac was obtained.

$^1$H-NMR for the product 30ac (CDCl$_3$, 500 MHz): δ 7.35 (brs, 1H), 6.63-6.68 (m, 2H), 5.93-5.95 (m, 2H), 5.39 (m, 1H), 4.89 (m, 1H), 4.33-4.59 (m, 6H), 4.16 (m, 1H), 3.92-4.00 (m, 2H), 2.85 (m, 1H), 2.32-2.39 (m, 3H), 1.67-1.80 (m, 5H), 1.52-1.62 (m, 5H), 1.40-1.48 (m, 3H), 1.30 (s, 9H), 1.13-1.26

(m, 4H), 1.05-1.10 (m, 3H), 1.04 (s, 9H), 0.89-0.99 (m, 3H). ESI-MS [(M+H)$^+$]: m/z calculated 886.4, founded 886.5.

Example 101

Synthesis of Compound 30ad

The synthetic procedure was carried out as the same as in Example 76 for preparation of compound 30ad. After purification, 31 mg of product 30ad was obtained.

$^1$H-NMR for the product 30ad (CDCl$_3$, 500 MHz): δ 10.03 (m, 1H), 7.20 (s, 1H), 6.88 (s, 1H), 6.81 (s, 1H), 6.72 (m, 1H), 5.38 (m, 1H), 4.85 (m, 1H), 4.59-4.68 (m, 2H), 4.43-4.51 (m, 4H), 4.18-4.20 (m, 5H), 3.85 (m, 2H), 2.86-2.96 (m, 2H), 2.42 (m, 1H), 2.34 (m, 1H), 2.19 (m, 2H), 1.60-1.70 (m, 5H), 1.51-1.58 (m, 5H), 1.44 (s, 9H), 1.36-1.39 (m, 3H), 1.13-1.21 (m, 2H), 1.04-1.07 (m, 4H), 1.01 (s, 9H), 0.97-0.99 (m, 3H). ESI-MS [(M+H)$^+$]: m/z calculated 915.5, founded 915.6.

Example 102

Synthesis of Compound 30ae

The synthetic procedure was carried out as the same as in Example 76 for preparation of compound 30ae. After purification, 31 mg of product 30ae was obtained.

$^1$H-NMR for the product 30ae (CDCl$_3$, 500 MHz): δ 10.03 (m, 1H), 7.19 (s, 1H), 6.88 (s, 1H), 6.80 (s, 1H), 6.64 (m, 1H), 5.38 (m, 1H), 5.07 (m, 1H), 4.89 (m, 1H), 4.60-4.69 (m, 2H), 4.45-4.54 (m, 4H), 4.20 (m, 5H), 3.86 (m, 2H), 2.91-2.96 (m, 1H), 2.44-2.49 (m, 1H), 2.32-2.34 (m, 1H), 2.17-2.21 (m, 2H), 1.81-1.90 (m, 4H), 1.64-1.71 (m, 8H), 1.52-1.57 (m, 7H), 1.33-1.36 (m, 2H), 1.05-1.28 (m, 7H), 1.01 (s, 9H), 0.93-0.99 (m, 3H). ESI-MS [(M+H)$^+$]: m/z calculated 927.5, founded 927.6

Example 103

Synthesis of Compound 30af

The synthetic procedure was carried out as the same as in Example 76 for preparation of compound 30af. After purification, 31 mg of product 30af was obtained.

$^1$H-NMR for the product 30af (CDCl$_3$, 500 MHz): δ 10.03 (s, 1H), 7.20 (s, 1H), 6.70 (s, 1H), 6.58 (s, 1H), 5.97 (s, 2H), 5.74 (m, 1H), 5.40 (br, 1H), 5.21-5.28 (m, 2H), 5.14-5.16 (m, 1H), 4.66 (m, 2H), 4.44-4.55 (m, 3H), 4.21-4.23 (m, 2H), 3.87 (m, 1H), 2.89 (m, 1H), 2.37 (m, 2H), 2.08 (m, 1H), 1.94 (m, 1H), 1.78 (m, 1H), 1.40-1.48 (m, 2H), 1.34 (s, 9H), 1.07 (m, 2H), 1.02 (s, 9H). ESI-MS [(M+H)$^+$]: m/z calculated 746.3, founded 746.4

Example 104

Synthesis of Compound 30ag

The synthetic procedure was carried out as the same as in Example 76 for preparation of compound 30ag. After purification, 31 mg of product 30ag was obtained.

Confirmed by ESI-MS [(M+H)$^+$]: m/z calculated 748.3, founded 748.4.

Example 105

Synthesis of Compound 30ah

The synthetic procedure was carried out as the same as in Example 76 for preparation of compound 30ah. After purification, 31 mg of product 30ah was obtained.

$^1$H-NMR for the product 30ah (CDCl$_3$, 500 MHz): δ 10.02 (s, 1H), 7.16-7.18 (m, 1H), 6.76 (m, 1H), 6.62-6.72 (m, 1H), 5.98 (s, 1H), 5.97 (m, 1H), 5.76 (m, 1H), 5.41 (s, 1H), 5.29 (m, 1H), 5.21 (m, 1H), 5.14-5.16 (m, 1H), 4.66-4.69 (m, 2H), 4.53-4.58 (m, 2H), 4.46 (m, 1H), 4.20-4.25 (m, 2H), 3.85 (m, 1H), 2.92 (m, 1H), 2.37-2.43 (m, 2H), 2.08 (m, 1H), 1.96 (m, 1H), 1.71 (m, 1H), 1.44-1.48 (m, 2H), 1.30-1.33 (m, 9H), 1.04-1.05 (m, 2H), 1.02 (s, 9H). ESI-MS [(M+H)$^+$]: m/z calculated 746.3, founded 746.4

Example 106

Synthesis of Compound 30aj

The synthetic procedure was carried out as the same as in Example 76 for preparation of compound 30aj. After purification, 23 mg of product 30aj was obtained.

Confirmed by ESI-MS [(M+H)$^+$]: m/z calculated 720.3, founded 720.4.

Example 107

Synthesis of Compound 30ak

The synthetic procedure was carried out as the same as in Example 76 for preparation of compound 30ak. After purification, 39 mg of product 30ak was obtained.

$^1$H-NMR for the product 30ak (CDCl$_3$, 500 MHz): δ 10.01 (s, 1H), 7.21 (s, 1H), 6.71 (s, 1H), 6.68 (s, 1H), 5.96 (m, 2H), 5.76 (m, 1H), 5.40 (s, 1H), 5.26-5.30 (m, 2H), 5.15-5.17 (m, 1H), 4.73 (br, 1H), 4.60-4.69 (m, 2H), 4.47-4.52 (m, 2H), 4.23 (m, 2H), 3.83 (m, 1H), 2.93 (m, 1H), 2.42 (m, 1H), 2.36 (m, 1H), 2.09 (m, 1H), 1.98 (m, 1H), 1.63-1.68 (m, 7H), 1.44-1.47 (m, 4H), 1.36 (m, 3H), 1.02 (s, 9H). ESI-MS [(M+H)$^+$]: m/z calculated 758.3, founded 758.4

Example 108

Synthesis of Compound 30am

The synthetic procedure was carried out as the same as in Example 76 for preparation of compound 30am. After purification, 40 mg of product 30am was obtained.

Confirmed by ESI-MS [(M+H)$^+$]: m/z calculated 760.3,

Example 109

Synthesis of Compound 30an

The synthetic procedure was carried out as the same as in Example 76 for preparation of compound 30an. After purification, 31 mg of product 30an was obtained.

$^1$H-NMR for the product 30an (CDCl$_3$, 500 MHz): δ 9.98 (s, 1H), 7.25 (s, 1H), 6.77 (m, 1H), 6.62-6.75 (m, 1H), 5.95 (m, 2H), 5.75 (m, 1H), 5.40 (s, 1H), 5.25-5.32 (m, 2H), 5.14-5.16 (m, 1H), 4.65-4.75 (m, 3H), 4.47-4.62 (m, 3H), 4.22-4.27 (m, 2H), 3.85 (m, 1H), 2.90 (m, 1H), 2.42 (m, 1H), 2.37 (m, 1H), 2.08 (m, 1H), 1.96 (m, 1H), 1.73 (m, 1H), 1.54-1.62 (m, 6H), 1.44 (m, 3H), 1.34 (m, 2H), 1.01-1.05 (m, 11H). ESI-MS [(M+H)$^+$]: m/z calculated 758.3, founded 758.4.

Example 110

Synthesis of Compound 30ap

The synthetic procedure was carried out as the same as in Example 76 for preparation of compound 30ap. After purification, 23 mg of product 30ap was obtained.

Confirmed by ESI-MS [(M+H)+]: m/z calculated 762.3, founded 762.4.

Example 111

Synthesis of Compound 30aq

The synthetic procedure was carried out as the same as in Example 76 for preparation of compound 30aq. After purification, 39 mg of product 30aq was obtained.

1H-NMR for the product 30aq (CDCl3, 500 MHz): δ 10.08 (s, 1H), 7.18 (brs, 1H), 6.69 (s, 1H), 6.58 (s, 1H), 5.96 (s, 2H), 5.40 (m, 1H), 4.47-4.64 (m, 4H), 4.3-4.44 (m, 2H), 4.29-4.31 (m, 1H), 3.89 (m, 1H), 2.92 (m, 1H), 2.34 (m, 2H), 1.58-1.68 (m, 3H), 1.36-1.43 (m, 2H), 1.28-1.33 (m, 1H), 1.26 (s, 9H), 1.05-1.07 (m, 3H), 1.01 (s, 9H), 0.95-0.98 (t, J=7.5 Hz, 1H). ESI-MS [(M+H)+]: m/z calculated 747.4, founded 747.5

Example 112

Synthesis of Compound 30ar

The synthetic procedure was carried out as the same as in Example 76 for preparation of compound 30ar. After purification, 33 mg of product 30ar was obtained.

1H-NMR for the product 30ar (CDCl3, 500 MHz): δ 10.18 (s, 1H), 7.11 (brs, 1H), 6.71 (s, 1H), 6.60 (s, 1H), 5.97 (s, 2H), 5.80-5.88 (m, 1H), 5.25-5.27 (d, J=9.5 Hz, 1H), 5.14-5.16 (d, J=10.5 Hz, 1H), 4.57-4.67 (m, 3H), 4.45-4.50 (m, 1H), 4.36-4.37 (m, 2H), 4.25-4.29 (m, 1H), 3.89 (m, 1H), 2.92 (m, 1H), 2.34-2.41 (m, 2H), 2.08-2.13 (m, 1H), 1.96-1.98 (m, 1H), 1.51-1.54 (m, 1H), 1.30-1.39 (m, 3H), 1.26 (s, 9H), 1.14-1.23 (m, 2H), 1.05 (m, 1H), 1.02 (s, 9H). ESI-MS [(M+H)+]: m/z calculated 745.4, founded 745.5.

Example 113

Synthesis of Compound 30-Ref

The synthetic procedure was carried out as the same as in Example 76 for preparation of compound 30-Ref. After purification, 37 mg of product 30-Ref was obtained.

1H-NMR for the product 30-Ref (CDCl3, 500 MHz): δ 9.99 (s, 1H), 7.28 (s, 1H), 7.07 (m, 1H), 6.96 (m, 2H), 5.75 (m, 1H), 5.41 (s, 1H), 5.26-5.31 (m, 2H), 5.15-5.17 (m, 1H), 4.63-4.85 (m, 5H), 4.50-4.53 (m, 1H), 4.29-4.32 (m, 1H), 4.22-4.24 (m, 1H), 3.83 (m, 1H), 2.91 (m, 1H), 2.42 (m, 1H), 2.38 (m, 1H), 2.09 (m, 1H), 1.94 (m, 1H), 1.60 (m, 4H), 1.51 (m, 3H), 1.44 (m, 3H), 1.35 (m, 2H), 1.01-1.05 (m, 11H). ESI-MS [(M+H)+]: m/z calculated 732.3, founded 732.4.

Example 114

Synthesis of Compound 33a

Chemical SM-15a (5.4 g, 10 mmol), SM-16 (1.1 eq) and DMF (80 mL) were added into 250 mL flask reactor, followed by adding coupling reagent EDCI (1.3 eq) to keep the amidation at 55° C. until completed. The reaction mixture was worked out to obtain crude product 31a, followed by removing Boc group with HCl-THF solution to obtain 32a (3.9 g, yield: 86%), which was purified by precipitation in hexane-EtOAc and dried directly for next step. ESI-MS (M+H+): m/z calculated 487.2, founded 487.2.

In the presence of coupling reagent HATU (1.3 eq) in DMF (1.0 mL), compound 32a (60 mg, 0.1 mmol) was reacted with another acid derivative SM-14a to obtain product 33a. After purification by flash column, 41 mg of 33a was obtained.

1H-NMR for the product 33a (CDCl3, 500 MHz): δ 9.40 (s, 1H), 8.77 (s, 1H), 8.55 (s, 1H), 8.16-8.17 (m, 1H), 7.32-7.33 (m, 1H), 7.04 (m, 1H), 6.72 (s, 1H), 6.68 (s, 1H), 5.94-5.95 (m, 2H), 5.36 (m, 1H), 4.77-4.80 (m, 1H), 4.69-4.72 (m, 1H), 4.59-4.64 (m, 2H), 4.51-4.53 (m, 2H), 4.44-4.47 (m, 2H), 4.18-4.20 (m, 1H), 3.80-3.83 (m, 1H), 2.78 (m, 1H), 2.64 (m, 1H), 2.26 (m, 1H), 1.88-1.92 (m, 1H), 1.77-1.79 (m, 1H), 1.66-1.69 (m, 3H), 1.59-1.61 (m, 4H), 1.38-1.42 (m, 2H), 1.10-1.19 (m, 3H), 1.00-1.07 (m, 3H), 0.97-0.99 (m, 9H), 0.89-0.93 (m, 3H), 0.85-0.86 (m, 2H), 0.61 (m, 2H), ESI-MS [(M+H)+]: m/z calculated 845.4, founded 845.4

Example 115

Synthesis of Compound 33b

The synthetic procedure was carried out as the same as in Example 114 for preparation of compound 33b. After purification, 41 mg of product 33b was obtained.

1H-NMR for the product 33b (CDCl3, 500 MHz): δ 9.39 (m, 1H), 8.77 (m, 1H), 8.57 (m, 1H), 8.33 (m, 1H), 7.75 (m, 1H), 6.76 (s, 2H), 6.69 (s, 1H), 6.62 (m, 1H), 6.06 (br, 1H), 5.70 (br, 1H), 4.86 (m, 1H), 4.54-4.66 (m, 3H), 4.44-4.51 (m, 2H), 4.25-4.41 (m, 1H), 4.25 (m, 4H), 4.09 (m, 1H), 2.82 (m, 1H), 2.58 (m, 1H), 2.22 (m, 1H), 1.97 (m, 2H), 2.19 (m, 2H), 1.78 (m, 4H), 1.68 (m, 2H), 1.25-1.29 (m, 6H), 1.05-1.16 (m, 4H), 1.05 (s, 9H), 0.84-0.85 (m, 2H), 0.76-0.79 (m, 3H). ESI-MS [(M+H)+]: m/z calculated 859.4, founded 859.5

Example 116

Synthesis of Compound 33c

The synthetic procedure was carried out as the same as in Example 114 for preparation of compound 33c. After purification, 21 mg of product 33c was obtained.

1H-NMR for the product 33c (CDCl3, 500 MHz): δ 9.28 (s, 1H), 8.75 (s, 1H), 8.56 (m, 2H), 7.72 (m, 1H), 6.76-6.78 (m, 1H), 6.65-6.67 (m, 1H), 6.68 (s, 1H), 5.99 (m, 2H), 5.32 (s, 1H), 4.86 (m, 1H), 4.44-4.67 (m, 6H), 4.09 (m, 2H), 2.82 (m, 1H), 2.61 (m, 1H), 2.24 (m, 1H), 2.03 (m, 2H), 1.84-1.87 (m, 2H, 1.65-1.78 (m, 5H), 1.21-1.34 (m, 5H), 1.09-1.25 (m, 4H), 1.05-1.09 (m, 9H), 0.84-0.85 (m, 2H), 0.76 (m, 4H). ESI-MS [(M+H)+]: m/z calculated 845.4, founded 845.4.

Example 117

Synthesis of Compound 33d

The synthetic procedure was carried out as the same as in Example 114 for preparation of compound 33d. After purification, 22mg of product 33d was obtained.

1H-NMR for the product 33d (CDCl3, 500 MHz): δ 9.28 (m, 1H), 8.76 (m, 1H), 8.56 (m, 2H), 7.77 (m, 1H), 6.80 (m, 1H), 6.76 (m, 1H), 6.65 (m, 1H), 6.60 (br, 1H), 4.47-4.69 (m, 6H), 4.26 (m, 4H), 4.09 (m, 1H), 2.83 (m, 1H), 2.59 (m, 1H), 2.22 (m, 1H), 1.85-1.87 (m, 2H), 1.62-1.72 (m, 8H), 1.26 (m, 6H), 1.05-1.19 (m, 4H), 1.01-1.05 (m, 9H), 0.85-0.86 (m, 2H), 0.76-0.79 (m, 3H). ESI-MS [(M+H)+]: m/z calculated 859.4, founded 859.5.

Example 118

Synthesis of Compound 33-Ref

The synthetic procedure was carried out as the same as in Example 114 for preparation of compound 33-Ref. After purification, 28 mg of product 33-Ref was obtained.

$^1$H-NMR for the product 33-Ref (CDCl$_3$, 500 MHz): δ 9.28 (m, 1H), 8.75 (s, 1H), 8.57 (m, 2H), 7.71 (m, 1H), 7.07 (m, 1H), 6.97-7.00 (m, 2H), 6.63 (m, 1H), 5.92 (m, 1H), 5.41 (s, 1H), 5.30-5.33 (m, 1H), 5.13-5.15 (m, 2H), 4.75 (m, 3H), 4.65-4.68 (m, 1H), 4.59 (m, 1H), 4.47-4.51 (m, 1H), 4.38-4.42 (m, 1H), 2.87 (m, 1H), 2.49 (m, 1H), 2.37 (m, 1H), 2.23-2.26 (m, 1H), 2.03 (m, 2H), 1.84-1.87 (m, 2H), 1.65-1.78 (m, 5H), 1.21-1.34 (m, 5H), 1.09-1.25 (m, 4H), 1.05-1.09 (m, 9H), 0.84-0.85 (m, 2H), 0.76 (m, 4H), ESI-MS [(M+H)$^+$]: m/z calculated 819.4, founded 819.4

This application claims priority to Chinese application No. CN 201010101403.7, filed on Jan. 27, 2010, and incorporated herein by reference.

What is claimed is:
1. A compound represented by the formula Ia:

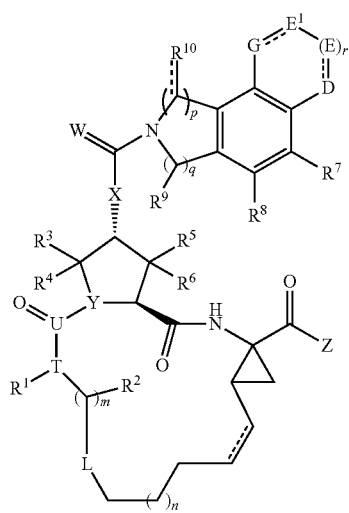

and/or stereoisomers, solvates, hydrates, tautomers pharmaceutically acceptable salts, or mixtures thereof, wherein:
m=0, 1 or 2;
n=0, 1 or 2;
p=0, 1 or 2;
q=0, 1 or 2;
r=0, 1, 2 or 3;
each dashed line "═" is, independently, a single bond or double bond;
wherein when D and E are connected by a single bond, D and E are each, independently, selected from the group consisting of 0, S, amino, and —C(Ra)(Rb)—; and R$^{10}$ is hydrogen, oxygen, halogen atom, cyano, trifluoromethyl, C$_1$-C$_{20}$ alkyl, C$_1$-C$_{20}$ alkoxy, C$_1$-C$_{20}$ alkylthio, C$_1$-C$_{20}$ alkoxycarbonyl, C$_1$-C$_{20}$ aminocarbonyl, C$_1$-C$_{20}$ carbonylamino, C$_6$-C$_{20}$ aryl, C$_6$-C$_{20}$ aryloxy, C$_6$-C$_{20}$ aryloxycarbonyl, or C$_2$-C$_{20}$ heterocyclic group;
wherein when D and E are connected by a double bond, D and E each, independently, selected from the group consisting of N or —C(Rc)-;
wherein when E$^1$ and G are connected by a single bond, E$^1$ and G are each, independently, selected from the group consisting of O, S, amino, and —C(Ra)(Rb)—; and R$^{10}$ is hydrogen, oxygen, halogen atom, cyano, trifluoromethyl, C$_1$-C$_{20}$ alkyl, C$_1$-C$_{20}$ alkoxy, C$_1$-C$_{20}$ alkylthio, C$_1$-C$_{20}$ alkoxycarbonyl, C$_1$-C$_{20}$ aminocarbonyl, C$_1$-C$_{20}$ carbonylamino, C$_6$-C$_{20}$ aryl, C$_6$-C$_{20}$ aryloxy, C$_6$-C$_{20}$ aryloxycarbonyl, or C$_2$-C$_{20}$ heterocyclic group;
wherein when E$^1$ and G are connected by a double bond, E$^1$ and G are each, independently, selected from the group consisting of N or —C(Rc)-;
wherein when the dashed line connecting R$^{10}$ to the macrocycle is a double bond, R$^{10}$ is O or S;
wherein when the dashed line connecting R$^{10}$ to the macrocycle is a single bond, R$^{10}$ is hydrogen, halogen atom, cyano, trifluoromethyl, C$_1$-C$_{20}$ alkyl, C$_1$-C$_{20}$ alkoxy, C$_1$-C$_{20}$ alkylthio, C$_1$-C$_{20}$ alkoxycarbonyl, C$_1$-C$_{20}$ aminocarbonyl, C$_1$-C$_{20}$ carbonylamino, C$_6$-C$_{20}$ aryl, C$_6$-C$_{20}$ aryloxy, C$_6$-C$_{20}$ aryloxycarbonyl, or C$_2$-C$_{20}$ heterocyclic group;
Ra, Rb and Rc are each, independently, selected from the group consisting of hydrogen, halogen atom, cyano, nitro, C$_1$-C$_{20}$ alkyl, C$_3$-C$_{20}$ cycloalkyl, C$_6$-C$_{20}$ aryl, C$_1$-C$_{20}$ alkoxy, C$_1$-C$_{20}$ alkylthio, C$_1$-C$_{20}$ alkoxycarbonyl, C$_6$-C$_{20}$ aryloxy, C$_6$-C$_{20}$ aryloxycarbonyl, C$_2$-C$_{20}$ heterocyclic alkoxycarbonyl, C$_2$-C$_{20}$ heterocyclic aryl, C$_1$-C$_{20}$ alkylamino, C$_2$-C$_{20}$ heterocyclic amino, C$_6$-C$_{20}$ aryl amino, C$_1$-C$_{20}$ aminocarbonyl, C$_1$-C$_{20}$ amido, C$_1$-C$_{20}$ amidocarbonyl, C$_1$-C$_{20}$ carbonylamino, C$_1$-C$_{20}$ alkylsulfonamido, C$_2$-C$_{20}$ heterocyclic sulfonamido, C$_6$-C$_{20}$ arylsulfonamido, and C$_1$-C$_{20}$ aminosulfonamido group;
wherein when r=0, E is nothing, and the D group is directly linked to the E$^1$ group;
L is oxygen, sulfur, —S(O)—, —S(O)$_2$—, carbonyl, —C(Rb)(Rc)-, —C(Rb)═C(Rc)-, C$_1$-C$_{20}$ alkoxy, C$_2$-C$_{20}$ heterocyclyl, C$_2$-C$_{20}$ heterocyclic alkoxy, —N(Ra)—, C$_1$-C$_{20}$ aminocarbonyl, C$_1$-C$_{20}$ alkoxycarbonyl, C$_6$-C$_{20}$ aryl, C$_6$-C$_{20}$ aryloxy, or C$_6$-C$_{20}$ aryloxycarbonyl group, wherein Ra, Rb and Rc are as defined above;
T is N, O or CH, wherein when T is O, R$^1$ is not present;
U is C;
W is O or S;
X is O, S or —NRa—, wherein Ra is defined above;
Y is N or CH;
Z is hydroxyl, C$_1$-C$_{20}$ alkyl, C$_3$-C$_{20}$ cycloalkyl, C$_1$-C$_{20}$ alkoxy, C$_3$-C$_{20}$ cycloalkoxy, C$_1$-C$_{20}$ alkylamino, C$_3$-C$_{20}$ cycloalkylamino, C$_2$-C$_{20}$ heterocyclic amino, C$_6$-C$_{20}$ aryl, C$_6$-C$_{20}$ arylamino, C$_4$-C$_{20}$ heteroarylamino, C$_1$-C$_{20}$ alkyl sulfonamido, C$_3$-C$_{20}$ cycloalkylsulfonamido, C$_6$-C$_{20}$ arylsulfonamido, C$_1$-C$_{20}$ alkoxy sulfonamido, C$_3$-C$_{20}$ cycloalkoxy sulfonamido, C$_1$-C$_{20}$ alkylamino sulfonamido, C$_3$-C$_{20}$ cycloalkylamino sulfonamido, C$_6$-C$_{20}$ arylamino sulfonamido, C$_1$-C$_{20}$ uramido, C$_1$-C$_{20}$ thioureido, C$_1$-C$_{20}$ phosphate, or C$_1$-C$_{20}$ borate;
R$^1$ and R$^2$ are each, independently, selected from the group consisting of hydrogen, hydroxyl, amino, C$_1$-C$_2$ alkyl, C$_3$-C$_{20}$ cycloalkyl, C$_1$-C$_{20}$ alkoxy, C$_3$-C$_{20}$ cycloalkoxy, C$_1$-C$_{20}$ alkoxycarbonyl, C$_1$-C$_{20}$ alkylamino, C$_3$-C$_{20}$ cycloalkylamino, C$_2$-C$_{20}$ heterocyclic amino, C$_6$-C$_{20}$ arylamino, C$_1$-C$_{20}$ alkoxycarbonylamino, C$_6$-C$_{20}$ aryloxycarbonylamino, C$_1$-C$_{20}$ alkylsulfonamido, C$_3$-C$_{20}$ cycloalkylsulfonamido, C$_2$-C$_{20}$ heterocyclic sulfonamido, C$_6$-C$_{20}$ arylsulfonamido, and C$_1$-C$_{20}$ aminosulfonamido group;
R$^3$, R$^4$, R$^5$ and R$^6$ are each, independently, selected from the group consisting of hydrogen, halogen, hydroxyl, cyano, nitro, C$_1$-C$_{20}$ alkyl, C$_3$-C$_{20}$ cycloalkyl, C$_1$-C$_{20}$ alkoxy, C$_1$-C$_{20}$ alkylamino, C$_2$-C$_{20}$ heterocyclicamino, C$_6$-C$_{20}$ aryl, C$_6$-C$_{20}$ arylamino, C$_1$-C$_{20}$ alkylsulfonamido, $C_2$-$C_{20}$ heterocyclic sulfonamido, and $C_6$-$C_{20}$ arylsulfonamido group; and $R^7$, $R^8$ and $R^9$ are each, independently, selected from the group consisting of hydrogen, cyano, nitro, trifluoromethyl, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, and $C_2$-$C_{20}$ heterocyclic group.

2. The compound according to claim 1, wherein m=1 or 2, n=1 or 2, p=1, q=1 and r=0, 1 or 2.

3. The compound according to claim 1, wherein the dashed line "═" is a single bond in the tricyclic ring containing D, E, $E^1$, and G.

4. The compound according to claim 3, wherein D and G each is 0 or an amino group; and
when r=0, $E^1$ is amino or —C(Ra)(Rb)— group directly linked with the D group;
when r=1 or 2, E and $E^1$ each is amino or —C(Ra)(Rb)—.

5. The compound according to claim 4, wherein D and G each is 0; and
when r=0, $E^1$ is a —$CH_2$— group directly linked with the D group;
when r=1 or 2, E and $E^1$ each is a —$CH_2$— group.

6. The compound according to claim 1, wherein Ra, Rb and Rc each is independently selected from the group consisting of hydrogen, halogen atom, cyano, nitro, $C_1$-$C_{12}$ alkyl, $C_3$-$C_{12}$ cycloalkyl, $C_6$-$C_{12}$ aryl, $C_1$-$C_{12}$ alkoxy, $C_1$-$C_{12}$ alkylthio, $C_1$-$C_{12}$ alkoxycarbonyl, $C_6$-$C_{12}$ aryloxy, $C_6$-$C_{12}$ aryloxycarbonyl, $C_2$-$C_{12}$ heterocyclic alkoxycarbonyl, $C_2$-$C_{12}$ heterocyclic aryl, $C_1$-$C_{12}$ alkylamino, $C_2$-$C_{12}$ heterocyclic amino, $C_6$-$C_{12}$ aryl amino, $C_1$-$C_{12}$ aminocarbonyl, $C_1$-$C_{12}$ amido, $C_1$-$C_{12}$ amidocarbonyl, $C_1$-$C_{12}$ carbonylamino, $C_1$-$C_{12}$ alkylsulfonamido, $C_2$-$C_{12}$ heterocyclic sulfonamido, $C_6$-$C_{12}$ arylsulfonamido, $C_1$-$C_{12}$ aminosulfonamido.

7. The compound according to claim 6, wherein Ra, Rb and Rc are each is hydrogen.

8. The compound according to claim 1, wherein L is oxygen, sulfur, —S(O)—, —S(O)$_2$—, carbonyl, —C(Rb)(Rc)-, —C(Rb)═C(Rc)-, $C_1$-$C_{12}$ alkoxy, $C_2$-$C_{12}$ heterocyclyl, $C_2$-$C_{12}$ heterocyclic alkoxy, $C_1$-$C_{12}$ amino [—N(Ra)—], $C_1$-$C_{12}$ aminocarbonyl, $C_1$-$C_{12}$ alkoxycarbonyl, $C_6$-$C_{12}$ aryl, $C_6$-$C_{12}$ aryloxy, or a $C_6$-$C_{12}$ aryloxycarbonyl group.

9. The compound according to claim 8, wherein L is —$CH_2$—.

10. The compound according to claim 1, wherein T is N or CH.

11. The compound according to claim 1, wherein U is C.

12. The compound according to claim 1, wherein W is O.

13. The compound according to claim 1, wherein X is O.

14. The compound according to claim 1, wherein Y is N or a CH group.

15. The compound according to claim 2, wherein Y is N or a CH group.

16. The compound according to claim 1, wherein Z is hydrogen, hydroxyl, $C_1$-$C_{12}$ alkyl, $C_3$-$C_{12}$ cycloalkyl, $C_1$-$C_{12}$ alkoxy, $C_3$-$C_{12}$ cycloalkoxy, $C_1$-$C_{12}$ alkylamino, $C_3$-$C_{12}$ cycloalkylamino, $C_2$-$C_{12}$ heterocyclic amino, $C_6$-$C_{12}$ aryl, $C_6$-$C_{12}$ arylamino, $C_4$-$C_{12}$ heteroarylamino, $C_1$-$C_{12}$ alkyl sulfonamido, $C_3$-$C_{12}$ cycloalkylsulfonamido, $C_6$-$C_{12}$ arylsulfonamido, $C_1$-$C_{12}$ alkylaminosulfonamido, $C_3$-$C_{12}$ cycloalkylamino sulfonamido, $C_6$-$C_{12}$ arylamino sulfonamido, $C_1$-$C_{12}$ uramido, $C_1$-$C_{12}$ thioureido, $C_1$-$C_{12}$ phosphate, or $C_1$-$C_{12}$ borate.

17. The compound according to claim 16, wherein Z is $C_1$-$C_6$ alkylsulfonamido, $C_6$-$C_{10}$ arylsulfonamido or $C_3$-$C_6$ cycloalkylsulfonamido group.

18. The compound according to claim 1, wherein $R^1$ and $R^2$ each is independently selected from the group consisting of hydrogen, hydroxyl, amino, $C_1$-$C_2$ alkyl, $C_3$-$C_{12}$ cycloalkyl, $C_1$-$C_{12}$ alkoxy, $C_3$-$C_{12}$ cycloalkoxy, $C_1$-$C_{12}$ alkoxycarbonyl, $C_1$-$C_{12}$ alkylamino, $C_3$-$C_{12}$ cycloalkylamino, $C_2$-$C_{12}$ heterocyclic amino, $C_6$-$C_{12}$ arylamino, $C_1$-$C_{12}$ alkoxycarbonylamino, $C_6$-$C_{12}$ aryloxycarbonylamino, $C_1$-$C_{12}$ alkylsulfonamido, $C_3$-$C_{12}$ cycloalkylsulfonamido, $C_2$-$C_{12}$ heterocyclic sulfonamido, $C_6$-$C_{12}$ arylsulfonamido, $C_1$-$C_{12}$ aminosulfonamido group.

19. The compound according to claim 18, wherein $R^1$ is hydrogen, $C_6$-$C_{10}$ arylamino, $C_1$-$C_6$ alkoxycarbonylamino, $C_2$-$C_6$ heterocyclic amino, $C_1$-$C_6$ alkylsulfonamido, or $C_6$-$C_{10}$ arylsulfonamido; and $R^2$ is hydrogen.

20. The compound according to claim 1, wherein $R^3$, $R^4$, $R^5$ and $R^6$ are each, independently, selected from the group consisting of hydrogen, halogen, hydroxyl, cyano, nitro, $C_1$-$C_{20}$ alkyl, $C_3$-$C_{20}$ cycloalkyl, $C_1$-$C_{20}$ alkoxy, $C_1$-$C_{20}$ alkylamino, $C_2$-$C_{20}$ heterocyclicamino, $C_6$-$C_{20}$ aryl, $C_6$-$C_{20}$ arylamino, $C_1$-$C_{20}$ alkylsulfonamido, $C_2$-$C_{20}$ heterocyclic sulfonamido, or $C_6$-$C_{20}$ arylsulfonamido group.

21. The compound according to claim 20, wherein $R^3$, $R^4$, $R^5$ and $R^6$ each is hydrogen (H).

22. The compound according to claim 1, wherein $R^7$, $R^8$ and $R^9$ are each, independently, selected from the group consisting of hydrogen, cyano, nitro, trifluoromethano, $C_1$-$C_{20}$ alkyl, $C_1$-$C_{20}$ alkoxy, $C_1$-$C_{20}$ alkylthio, $C_1$-$C_{20}$ alkoxycarbonyl, $C_1$-$C_{20}$ aminocarbonyl, $C_1$-$C_{20}$ carbonylamino, $C_6$-$C_{20}$ aryl, $C_6$-$C_{20}$ aryloxy, $C_6$-$C_{20}$ aryloxycarbonyl, $C_2$-$C_{20}$ heterocyclic group.

23. The compound according to claim 22, wherein $R^7$, $R^8$ and $R^9$ each is hydrogen (H).

24. The compound according to claim 1, wherein $R^{10}$ is hydrogen (H), and the dashed line "═" linked to $R^{10}$ group is single bond.

25. The compound according to claim 1, wherein the dashed line "═" linked to the cyclopropylaminocarbonyl group of macrocyclic ring is double bond.

26. A pharmaceutical composition comprising at least one compound of claim 1.

27. A pharmaceutical composition, comprising at least one compound of claim 1 in a therapeutically effective dose and at least one additional medicament in a therapeutically effective dose.

28. A pharmaceutical composition, comprising at least one compound of claim 1 in a therapeutically effective dose and at least one HIV inhibitor in a therapeutically effective dose.

29. A pharmaceutical composition, comprising at least one compound of claim 1 in a therapeutically effective dose and at least one hepatitis B virus (HBV) inhibitor in a therapeutically effective dose.

30. A method of inbibiting HCV, comprising administering an effect amount of the compound of claim 1 to a subject in need thereof.

31. The method of claim 30, further comprising administering at least one medicament selected from the group consisting of (1) immune modulators, (2) HCV protease inhibitors, (3) HCV polymerase inhibitors, (4) nucleosides and its derivatives, (5) cyclophilin inhibitors, (6) glucosidase I inhibitors, (7) IMPDH inhibitors, (8) caspase inhibitors, (9) TLR agonists, (10) HIV inhibitors, (11) anti-inflammatory drugs, and (12) anti-cancer drugs.

32. The compound according to claim 1, wherein m is 0.

33. The compound according to claim 1, wherein m is 1.

\* \* \* \* \*